US008420887B2

(12) United States Patent
Frankard et al.

(10) Patent No.: US 8,420,887 B2

(45) Date of Patent: *Apr. 16, 2013

(54) PLANTS HAVING IMPROVED GROWTH CHARACTERISTICS AND METHOD FOR MAKING THE SAME

(75) Inventors: Valerie Frankard, Waterloo (BE); Ana Isabel Sanz Molinero, Gentbrugge (BE); Vladimir Mironov, Ghent (BE)

(73) Assignee: CropDesign N.V. (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/169,556

(22) Filed: Jun. 27, 2011

(65) Prior Publication Data

US 2012/0005785 A1 Jan. 5, 2012

Related U.S. Application Data

(62) Division of application No. 11/632,570, filed as application No. PCT/EP2005/053397 on Jul. 14, 2005, now Pat. No. 7,968, 765.

(60) Provisional application No. 60/589,235, filed on Jul. 20, 2004.

(30) Foreign Application Priority Data

Jul. 15, 2004 (EP) .................................... 04103393

(51) Int. Cl.

| | |
|---|---|
| ***C12N 15/82*** | (2006.01) |
| ***C12N 15/63*** | (2006.01) |
| ***A01H 1/06*** | (2006.01) |
| ***A01H 5/00*** | (2006.01) |
| ***C07H 21/04*** | (2006.01) |

(52) U.S. Cl.

USPC ........... 800/278; 800/290; 800/298; 435/410; 435/468; 435/91.4; 435/440; 536/23.6

(58) Field of Classification Search ........................ None

See application file for complete search history.

(56) References Cited

U.S. PATENT DOCUMENTS

| | | | | |
|---|---|---|---|---|
| 5,859,338 | A | 1/1999 | Meyerowitz et al. | |
| 6,730,634 | B1 * | 5/2004 | Houtz et al. ............... | 504/116.1 |
| 2006/0150283 | A1 * | 7/2006 | Alexandrov et al. ......... | 800/288 |

FOREIGN PATENT DOCUMENTS

| | | | |
|---|---|---|---|
| WO | WO-98/59039 | A1 | 12/1998 |
| WO | WO-00/04761 | A1 | 2/2000 |
| WO | WO-03/072763 | A1 | 9/2003 |
| WO | WO-2004/035798 | A2 | 4/2004 |

OTHER PUBLICATIONS

P. Becraft, Annu. Rev. Cell Dev. Biol., 2002, 18:163-92.*

NCBI Database Accession No. NP-175594, Feb. 17, 2004 (protein) and NCBI Accession No. FJ708652, Locus Tag GENE ID: 841609 AT1G51820 (DNA).*

BLAST results with SEQ ID Nos. 6 and 7, NCBI Database Accession No. NP-175597.1, Jan. 10, 2002 (protein) and NCBI Accession No. NM 104065.2 (DNA).*

Clark, S., et al. "The *CLAVATA1* Gene Encodes a Putative Receptor Kinase That Controls Shoot and Floral Meristem Size in *Arabidopsis*", Cell, vol. 89, (1997), pp. 575-585.

Gomez-Gomez, L., et al., "Flagellin Perception: a Paradigm for Innare Immunity", Trends in Plant Science, vol. 7, No. 6, (2002), pp. 251-256.

Dievart, A., et al., "LRR-containing Receptors Regulating Plant Development and Defense", Development, vol. 131, (2004), pp. 251-261.

De Veylder, L., et al., "Control of Proliferation, Endoreduplication and Eifferentiation by the *Arabidopsis* E2Fa-DPa Transcription Factor". EMBO Journal, vol. 21, (2002), pp. 1360-1368.

Hatakeyama, K. et al., "The S Receptor Kinase Gene Determines Dominance Relationships in Stigma Expression of Self-Incompatibility in *Brassica*", Plant Journal, vol. 26, (2001), pp. 69-76.

Matsubayashi, Y. et al., "An LRR Receptor Kinase Involved in Perception of a Peptide Plant Hormone, Phytosulfokine", Science, 2002, vol. 296, No. 5572, pp. 1470-1472.

Li, J. et al., "BAK1, an *Arabidopsis* LRR Receptor-like Protein Kinase, INteracts with BRI1 and Modulates Brassinosteroid Signaling", Cell, 2002, vol. 110, pp. 213-222.

Shiu, S. H. et al., "Receptor-like Kinases from *Arabidopsis*Form a Monophyletic Gene Family Related to Animal Receptor Kinases", Proceedings of National Academy of Science, 2001, vol. 98, No. 19, pp. 10763-10768.

Sylvia de Pater, B. et al., "The Promoter of the Rice Gene *GOS2*is Active in Various Different Monocot Tissues and Binds Rice Nuclear Factor ASF-1", The Plant Journal, 1992, vol. 2, No. 6, pp. 837-844.

Federspiel, N.A., et al., "Putative protein kinase [*Arabidopsis thaliana*]", NCBI Database, Accession No. AAF99853, Aug. 15, 2000.

Becraft, P. W., "Receptor Kinase Signaling in Plant Development", Annu. Rev. Cell Dev. Biol., vol. 18, (2002), pp. 163-192.

Diévart, A., et al., "Using Mutant Alleles to Determine the Structure and Function of Leucine-rich Repeat Receptor-like Kinases", Current Opinion in Plant Biology, vol. 6, (2003), pp. 507-516.

Kobe, B., et al., "The Leucine-rich Repeat as a Protein Recognition Motif", Current Opinion in Structural Biology, vol. 11, (2001), pp. 725-732.

* cited by examiner

*Primary Examiner* — Eileen B O Hara

(74) *Attorney, Agent, or Firm* — Novak Druce Connolly Bove + Quigg LLP

(57) ABSTRACT

The present invention concerns a method for improving growth characteristics of plants by increasing expression and/or activity in a plant of an LRR receptor kinase or a homologue thereof. One such method comprises introducing into a plant an RLK827 nucleic acid molecule or functional variant thereof. The invention also relates to transgenic plants having improved growth characteristics, which plants have modulated expression of a nucleic acid encoding an LRR receptor kinase. The present invention also concerns constructs useful in the methods of the invention.

19 Claims, 25 Drawing Sheets

SEQ ID NO 1: RLK827 DNA sequence

ATGGAGAGACATTTTGTGTTTATTGCCACCTATTTGCTGATATTTCATCTTGTTCAAGCTC
AAAATCAAACAGGATTCATTAGTGTGGATTGTGGTTTATCCCTTCTTGAGTCTCCTTACGA
TGCACCCACAAACGAGTTTAACATATACATCAGATGCCGATTTAGTAGCTAGTGGCAAAACC
GGTAGACTCGCCAAAGAATTTGAACCACTCGTTGATAAGCCGACTTTGACACTGAGATACT
TTCCAGAGGGAGTACGAAACTGCTACAATCTAAATGTCACCAGCGACACCAACTATTTAAT
CAAGGCCACATTTGTATATGGGAATTACGATGGTCTTAATGTTGGGCCAAACTTCAACCTT
TATCTCGGTCCGAATTTGTGGACAACGGTGAGTAGCAATGACACTATAGAGGAAATAATCC
TTGTGACCAGATCCAACTCTTTACAGGTGTGTCTTGTTAAGACGGGAATAAGTATACCTTT
TATAAATATGTTGGAGCTACGACCGATGAAGAAAAATATGTACGTTACTCAAAGCGGTTCA
CTGAAGTATTTATTCAGAGGGTATATTAGCAATTCAAGTACTCGTATAAGGTTCCCGGATG
ATGTCTATGACCGTAAATGGTACCCGCTCTTCGACGACTCATGGACACAAGTAACTACAAA
TCTCAAAGTGAACACAAGTATTACTTATGAACTACCACAAAGTGTAATGGCAAAAGCCGCA
ACGCCAATTAAGGCTAACGACACCTTGAACATTACATGGACGGTAGAGCCCCCTACTACAC
AGTTTTACTCTTACGTACACATTGCAGAGATTCAGGCTCTAAGGGCAAACGAGACAAGGGA
GTTCAATGTGACACTGAATGGAGAATATACTTTTGGACCTTTTAGTCCTATACCGCTAAAA
ACCGCATCCATAGTCGACTTAAGCCCAGGGCAATGCGATGGAGGGAGATGCATTTTGCAGG
TTGTGAAGACGCTGAAATCTACGCTTCCTCCTTTACTTAATGCTATCGAAGCTTTCACCGT
GATTGATTTCCCGCAAATGGAGACAAATGAAAATGATGTTGCTGGGATCAAGAATGTTCAA
GGTACTTATGGATTGAGTAGAATTAGTTGGCAAGGAGATCCATGTGTCCCCAAACAGTTAT
TGTGGGATGGTCTAAACTGCAAAAACTCGGATATTTCTACGCCACCGATAATCACTTCCTT
AGACTTATCTTCAAGTGGATTAACTGGGATCATCACGCAAGCCATTAAGAATCTTACTCAC
CTGCAAATATTGGACTTGTCAGATAATAATTTGACTGGAGAAGTACCTGAGTTTTTAGCTG
ACATAAAATCACTCTTGGTCATAAACTTAAGTGGTAATAATCTAAGTGGCTCAGTTCCTCC
CTCACTTCTTCAGAAGAAAGGAATGAAGTTAAATGTCGAAGGCAATCCTCATATTCTTTGC
ACAACGGGTTCTTGTGTCAAGAAAAAAGAGGATGGACATAAGAAAAAGAGTGTCATAGTGC
CAGTTGTTGCATCAATTGCTTCAATAGCTGTTCTTATAGGTGCATTGGTTCTGTTTCTAAT
TCTTAGAAAGAAAAGGTCACCAAAAGTTGAAGGGCCACCACCATCTTATATGCAAGCATCA
GATGGTAGATTGCCTAGATCATCTGAACCGGCAATCGTAACGAAAAATAGAAGGTTTTCTT
ATTCACAAGTTGTGATAATGACAAATAACTTCCAAAGAATCCTTGGGAAAGGAGGGTTTGG
AATGGTTTATCATGGTTTCGTGAACGGTACAGAGCAAGTAGCTGTTAAGATACTCTCCCAT
TCATCGTCTCAAGGATATAAACAATTCAAAGCTGAGGTAGAACTTCTTCTTAGAGTTCATC
ACAAGAACTTGGTTGGTCTTGTTGGGTACTGCGACGAAGGAGATAACTTGGCTCTTATCTA
TGAATACATGGCCAATGGAGATCTAAAAGAACATATGTCAGGAACACGTAACCGCTTTATT
TTGAATTGGGGAACTAGACTAAAAATAGTCATCGAGTCTGCACAAGGACTCGAGTACTTGC
ATAATGGTTGCAAACCACCAATGGTACATAGGGACGTCAAAACTACAAATATATTGTTGAA
CGAACACTTTGAGGCCAAACTTGCGGATTTTGGGCTTTCGAGATCATTCCTGATCGAAGGT
GAAACTCATGTATCAACAGTTGTTGCTGGAACTCCTGGATATCTCGATCCTGAATACCATA
GAACAAATTGGTTGACAGAAAAGAGTGATGTTTATAGTTTTGGGATTCTATTGTTGGAGAT
TATCACAAACCGACATGTGATCGACCAAAGCCGTGAAAAGCCACACATAGGAGAATGGGTA
GGAGTAATGCTTACAAAAGGAGACATCCAAAGCATTATGGATCCAAGTCTCAATGAAGATT
ATGATTCCGGTTCTGTTTGGAAAGCTGTTGAACTAGCAATGAGTTGTCTAAATCATTCTTC
AGCGAGAAGACCGACCATGTCCCAAGTTGTTATTGAATTGAACGAGTGTCTGGCTTCTGAA
AATGCAAGGGGAGGAGCAAGTCGGGACATGGAATCAAAGAGTTCTATAGAAGTGAGCTTGA
CGTTTGGTACTGAAGTGAGCCCAAACGCTCGA

FIGURE 4A

SEQ ID NO 2: RLK827 deduced protein sequence

MERHFVFIATYLLIFHLVQAQNQTGFISVDCGLSLLESPYDAPQTSLTYTSDADLVASGKT
GRLAKEFEPLVDKPTLTLRYFPEGVRNCYNLNVTSDTNYLIKATFVYGNYDGLNVGPNFNL
YLGPNLWTTVSSNDTIEEIILVTRSNSLQVCLVKTGISIPFINMLELRPMKKNMYVTQSGS
LKYLFRGYISNSSTRIRFPDDVYDRKWYPLFDDSWTQVTTNLKVNTSITYELPQSVMAKAA
TPIKANDTLNITWTVEPPTTQFYSYVHIAEIQALRANETREFNVTLNGEYTFGPFSPIPLK
TASIVDLSPGQCDGGRCILQVVKTLKSTLPPLLNAIEAFTVIDFPQMETNENDVAGIKNVQ
GTYGLSRISWQGDPCVPKQLLWDGLNCKNSDISTPPIITSLDLSSSGLTGIITQAIKNLTH
LQILDLSDNNLTGEVPEFLADIKSLLVINLSGNNLSGSVPPSLLQKKGMKLNVEGNPHILC
TTGSCVKKKEDGHKKKSVIVPVVASIASIAVLIGALVLFLILRKKRSPKVEGPPPSYMQAS
DGRLPRSSEPAIVTKNRRFSYSQVVIMTNNFQRILGKGGFGMVYHGFVNGTEQVAVKILSH
SSSQGYKQFKAEVELLLRVHHKNLVGLVGYCDEGDNLALIYEYMANGDLKEHMSGTRNRFI
LNWGTRLKIVIESAQGLEYLHNGCKPPMVHRDVKTTNILLNEHFEAKLADFGLSRSFLIEG
ETHVSTVVAGTPGYLDPEYHRTNWLTEKSDVYSFGILLLEIITNRHVIDQSREKPHIGEWV
GVMLTKGDIQSIMDPSLNEDYDSGSVWKAVELAMSCLNHSSARRPTMSQVVIELNECLASE
NARGGASRDMESKSSIEVSLTFGTEVSPNAR

SEQ ID NO 3: expression cassette

AATCCGAAAAGTTTCTGCACCGTTTTCACCCCCTAACTAACAATATAGGGAACGTGTGCTA
AATATAAAATGAGACCTTATATATGTAGCGCTGATAACTAGAACTATGCAAGAAAAACTCA
TCCACCTACTTTAGTGGCAATCGGGCTAAATAAAAAAGAGTCGCTACACTAGTTTCGTTTT
CCTTAGTAATTAAGTGGGAAAATGAAATCATTATTGCTTAGAATATACGTTCACATCTCTG
TCATGAAGTTAAATTATTCGAGGTAGCCATAATTGTCATCAAACTCTTCTTGAATAAAAAA
ATCTTTCTAGCTGAACTCAATGGGTAAAGAGAGAGATTTTTTTTAAAAAAATAGAATGAAG
ATATTCTGAACGTATTGGCAAAGATTTAAACATATAATTATATAATTTTATAGTTTGTGCA
TTCGTCATATCGCACATCATTAAGGACATGTCTTACTCCATCCCAATTTTTATTTAGTAAT
TAAAGACAATTGACTTATTTTTATTATTTATCTTTTTTCGATTAGATGCAAGGTACTTACG
CACACACTTTGTGCTCATGTGCATGTGTGAGTGCACCTCCTCAATACACGTTCAACTAGCA
ACACATCTCTAATATCACTCGCCTATTTAATACATTTAGGTAGCAATATCTGAATTCAAGC
ACTCCACCATCACCAGACCACTTTTAATAATATCTAAAATACAAAAAAATAATTTTACAGAA
TAGCATGAAAAGTATGAAACGAACTATTTAGGTTTTTCACATACAAAAAAAAAAAGAATTT
TGCTCGTGCGCGAGCGCCAATCTCCCATATTGGGCACACAGGCAACAACAGAGTGGCTGCC
CACAGAACAACCCACAAAAAACGATGATCTAACGGAGGACAGCAAGTCCGCAACAACCTTT
TAACAGCAGGCTTTGCGGCCAGGAGAGAGGAGGAGAGGCAAAGAAAACCAAGCATCCTCCT
CCTCCCATCTATAAATTCCTCCCCCCTTTTCCCCTCTCTATATAGGAGGCATCCAAGCCAA
GAAGAGGGAGAGCACCAAGGACACGCGACTAGCAGAAGCCGAGCGACCGCCTTCTTCGATC
CATATCTTCCGGTCGAGTTCTTGGTCGATCTCTTCCCTCCTCCACCTCCTCCTCACAGGGT
ATGTGCCCTTCGGTTGTTCTTGGATTTATTGTTCTAGGTTGTGTAGTACGGGCGTTGATGT
TAGGAAAGGGGATCTGTATCTGTGATGATTCCTGTTCTTGGATTTGGGATAGAGGGGTTCT
TGATGTTGCATGTTATCGGTTCGGTTTGATTAGTAGTATGGTTTTCAATCGTCTGGAGAGC
TCTATGGAAATGAAATGGTTTAGGGTACGGAATCTTGCGATTTTGTGAGTACCTTTTGTTT
GAGGTAAAATCAGAGCACCGGTGATTTTGCTTGGTGTAATAAAAGTACGGTTGTTTGGTCC
TCGATTCTGGTAGTGATGCTTCTCGATTTGACGAAGCTATCCTTTGTTTATTCCCTATTGA
ACAAAAATAATCCAACTTTGAAGACGGTCCCGTTGATGAGATTGAATGATTGATTCTTAAG
CCTGTCCAAAATTTCGCAGCTGGCTTGTTTAGATACAGTAGTCCCCATCACGAAATTCATG

FIGURE 4B

GAAACAGTTATAATCCTCAGGAACAGGGGATTCCCTGTTCTTCCGATTTGCTTTAGTCCCA
GAATTTTTTTTCCCAAATATCTTAAAAAGTCACTTTCTGGTTCAGTTCAATGAATTGATTG
CTACAAATAATGCTTTTATAGCGTTATCCTAGCTGTAGTTCAGTTAATAGGTAATACCCCT
ATAGTTTAGTCAGGAGAAGAACTTATCCGATTTCTGATCTCCATTTTTAATTATATGAAAT
GAACTGTAGCATAAGCAGTATTCATTTGGATTATTTTTTTATTAGCTCTCACCCCTTCAT
TATTCTGAGCTGAAAGTCTGGCATGAACTGTCCTCAATTTTGTTTTCAAATTCACATCGAT
TATCTATGCATTATCCTCTTGTATCTACCTGTAGAAGTTTCTTTTTGGTTATTCCTTGACT
GCTTGATTACAGAAAGAAATTTATGAAGCTGTAATCGGGATAGTTATACTGCTTGTTCTTA
TGATTCATTTCCTTTGTGCAGTTCTTGGTGTAGCTTGCCACTTTCACCAGCAAAGTTCATT
TAAATCAACTAGGGATATCACAAGTTTGTACAAAAAAGCAGGCTTCACAATGGAGAGACAT
TTTGTGTTTATTGCCACCTATTTGCTGATATTTCATCTTGTTCAAGCTCAAAATCAAACAG
GATTCATTAGTGTGGATTGTGGTTTATCCCTTCTTGAGTCTCCTTACGATGCACCACAAAC
GGGTTTAACATATACATCAGATGCCGATTTAGTAGCTAGTGGCAAAACCGGTAGACTCGCC
AAAGAATTTGAACCACTCGTTGATAAGCCGACTTTGACACTGAGATACTTTCCAGAGGGAG
TACGAAACTGCTACAATCTAAATGTCACCAGCGACACCAACTATTTAATCAAGGCCACATT
TGTATATGGGAATTACGATGGTCTTAATGTTGGGCCAAACTTCAACCTTTATCTCGGTCCG
AATTTGTGGACAACGGTGAGTAGCAATGACACTATAGAGGAAATAATCCTTGTGACCAGAT
CCAACTCTTTACAGGTGTGTCTTGTTAAGACGGGAATAAGTATACCTTTTATAAATATGTT
GGAGCTACGACCGATGAAGAAAAATATGTACGTTACTCAAAGCGGTTCACTGAAGTATTTA
TTCAGAGGGTATATTAGCAATTCAAGTACTCGTATAAGGTTCCCGGATGATGTCTATGACC
GTAAATGGTACCCGCTCTTCGACGACTCATGGACACAAGTAACTACAAATCTCAAAGTGAA
CACAAGTATTACTTATGAACTACCACAAAGTGTAATGGCAAAAGCCGCAACGCCAATTAAG
GCTAACGACACCTTGAACATTACATGGACGGTAGAGCCCCCTACTACACAGTTTTACTCTT
ACGTACACATTGCAGAGATTCAGGCTCTAAGGGCAAACGAGACAAGGGAGTTCAATGTGAC
ACTGAATGGAGAATATACTTTTGGACCTTTTAGTCCTATACCGCTAAAAACCGCATCCATA
GTCGACTTAAGCCCAGGGCAATGCGATGGAGGGAGATGCATTTTGCAGGTTGTGAAGACGC
TGAAATCTACGCTTCCTCCTTTACTTAATGCTATCGAAGCTTTCACCGTGATTGATTTCCC
GCAAATGGAGACAAATGAAAATGATGTTGCTGGGATCAAGAATGTTCAAGGTACTTATGGA
TTGAGTAGAATTAGTTGGCAAGGAGATCCATGTGTCCCCAAACAGTTATTGTGGATGGTC
TAAACTGCAAAAACTCGGATATTTCTACGCCACCGATAATCACTTCCTTAGACTTATCTTC
AAGTGGATTAACTGGGATCATCACGCAAGCCATTAAGAATCTTACTCACCTGCAAATATTG
GACTTGTCAGATAATAATTTGACTGGAGAAGTACCTGAGTTTTTAGCTGACATAAAATCAC
TCTTGGTCATAAACTTAAGTGGTAATAATCTAAGTGGCTCAGTTCCTCCCTCACTTCTTCA
GAAGAAAGGAATGAATGTCGAAGGCAATCCTCATATTCTTTGCACAACGGGTTCTTGTGTC
AAGAAAAAAGAGGATGGACATAAGAAAAAGAGTGTCATAGTGCCAGTTGTTGCATCAATTG
CTTCAATAGCTGTTCTTATAGGTGCATTGGTTCTGTTTCTAATTCTTAGAAAGAAAAGGTC
ACCAAAAGTTGAAGGGCCACCACCATCTTATATGCAAGCATCAGATGGTAGATTGCCTAGA
TCATCTGAACCGGCAATCGTAACGAAAAATAGAAGGTTTTCTTATTCACAAGTTGTGATAA
TGACAAATAACTTCCAAAGAATCCTTGGGAAAGGAGGGTTTGGAATGGTTTATCATGGTTT
CGTGAACGGTACAGAGCAAGTAGCTGTTAAGATACTCTCCCATTCATCGTCTCAAGGATAT
AAACAATTCAAAGCTGAGGTAGAACTTCTTCTTAGAGTTCATCACAAGAACTTGGTTGGTC
TTGTTGGGTACTGCGACGAAGGAGATAACTTGGCTCTTATCTATGAATACATGGCCAATGG
AGATCTAAAAGAACATATGTCAGGAACACGTAACCGCTTTATTTTGAATTGGGGAACTAGA
CTAAAAATAGTCATCGAGTCTGCACAAGGACTCGAGTACTTGCATAATGGTTGCAAACCAC

FIGURE 4C

AATGGTACATAGGGACGTCAAAACTACAAATATATTGTTGAACGAACACTTTGAGGCCAA
ACTTGCGGATTTTGGGCTTTCGAGATCATTCCTGATCGAAGGTGAAACTCATGTATCAACA
GTTGTTGCTGGAACTCCTGGATATCTCGATCCTGAATACCATAGAACAAATTGGTTGACAG
AAAAGAGTGATGTTTATAGTTTTGGGATTCTATTGTTGGAGATTATCACAAACCGACATGT
GATCGACCAAAGCCGTGAAAAGCCACACATAGGAGAATGGGTAGGAGTAATGCTTACAAAA
GGAGACATCCAAAGCATTATGGATCCAAGTCTCAATGAAGATTATGATTCCGGTTCTGTTT
GGAAAGCTGTTGAACTAGCAATGAGTTGTCTAAATCATTCTTCAGCGAGAAGACCGACCAT
GTCCCAAGTTGTTATTGAATTGAACGAGTGTCTGGCTTCTGAAAATGCAAGGGGAGGAGCA
AGTCGGGACATGGAATCAAAGAGTTCTATAGAAGTGAGCTTGACGTTTGGTACTGAAGTGA
GCCCAAACGCTCGATAGT

SEQ ID NO 4: forward primer
GGGGACAAGTTTGTACAAAAAAGCAGGCTTCACAATGGAGAGACATTTTGTGTTTATTG

SEQ ID NO 5: reverse primer
GGGGACCACTTTGTACAAGAAAGCTGGGTGATGCAAACTATCGAGCGTTT

SEQ ID NO 6: At1g51850 DNA sequence
ATGGAGAGACATTGTGTGTTAGTTGCCACTTTTTTGCTGATGCTTCATATCGTTCATGCTC
AGGATCAAATTGGATTCATTAGTGTGGATTGTGGTTTGGCACCTCGTGAGTCTCCTTACAA
TGAAGCCAAAACTGGTTTAACATATACATCAGATGACGGTCTAGTCAACGTTGGGAAACCC
GGTAGAATCGCCAAGGAATTCGAACCGCTCGCCGATAAGCCGACTTTGACACTGAGATATT
TTCCAGAGGGAGTACGAAACTGCTACAATCTAAATGTCACCAGCGACACCAACTATCTGAT
CAAGGCCACATTCGTATATGGAAATTACGATGGTCTTAATGTTGGGCCAAACTTCGACCTT
TACTTCGGTCCGAATTTGTGGACTACGGTATGTCTTATTAAGACTGGAATAAGTATACCTT
TTATAAATGTTTTGGAGCTACGACCGATGAAGAAAAACATGTACGTTACTCAAGGCGAATC
ACTGAATTACTTATTCAGGGTGTATATTAGCAATTCAAGTACTCGTATAAGGTTCCCGGAT
GATGTCTATGATCGTAAATGGTACCCGTACTTCGACAACTCATGGACACAAGTAACTACGA
CTCTCGATGTAAACACAAGTCTTACTTATGAACTACCACAAAGTGTAATGGCAAAAGCCGC
AACGCCAATTAAGGCTAACGACACCTTGAACATTACATGGACAGTAGAGCCTCCTACTACA
AAGTTTTACTCCTACATGCACTTTGCAGAGCTTCAGACTTTAAGAGCCAACGATGCAAGGG
AATTCAATGTGACGATGAATGGAATATATACATATGGACCTTATAGTCCTAAACCACTAAA
AACCGAAACCATATACGACAAAATCCCTGAGCAATGCGATGGAGGTGCATGCCTTTTGCAG
GTTGTGAAGACACTTAAATCTACCCTTCCACCTTTACTTAATGCTATCGAGGCTTTCACCG
TGATTGATTTCCCGCAGATGGAGACTAATGGAGATGACGTTGATGCAATCAAGAATGTTCA
AGATACGTATGGAATTAGTAGAATTAGTTGGCAAGGAGATCCATGTGTCCCCAAACTGTTT
TTGTGGGATGGTCTAAATTGCAACAACTCCGATAATTCGACATCACCAATCATCACTTCCT
TAGACTTATCTTCAAGTGGACTAACTGGGAGCATCACCCAAGCCATTCAGAATCTAACTAA
CCTGCAAGAACTGGACTTGTCAGATAACAATTTGACTGGAGAAATACCTGATTTCTTAGGG
GACATTAAATCACTCTTGGTCATAAACTTAAGTGGTAATAATCTAAGTGGCTCAGTTCCTC
CCTCACTTCTTCAGAAGAAAGGAATGAAGTTAAATGTCGAAGGAAACCCTCATCTTCTTTG
CACAGCTGATTCATGTGTGAAAAAAGGAGAGGATGGACACAAGAAAAAGAGTGTCATAGTG
CCAGTTGTTGCATCAATTGCTTCAATAGCTGTTCTTATAGGTGCATTGGTTCTGTTTTTCA
TTCTTAGAAAGAAAAAGTCACCAAAAGTTGAAGGACCACCACCATCTTATATGCAAGCATC

FIGURE 4D

AGATGGTAGATCGCCAAGATCATCTGAACCGGCAATAGTGACAAAGAATAGAAGGTTTACT
TACTCACAAGTTGCGATAATGACAAATAACTTCCAAAGAATCCTTGGAAAAGGAGGGTTTG
GAATGGTTTATCATGGTTTTGTGAACGGTACAGAACAAGTAGCTGTTAAGATACTCTCCCA
TTCATCGTCTCAAGGATATAAAGAATTTAAAGCGGAGGTAGAACTTCTTCTTAGAGTTCAT
CACAAGAACTTGGTCGGTCTTGTTGGGTACTGCGACGAAGGAGAGAACATGGCTCTTATCT
ATGAATACATGGCCAATGGAGATCTAAAAGAACATATGTCAGGAACACGTAACCGGTTTAC
TTTGAATTGGGGAACTAGACTGAAAATAGTCGTCGAGTCTGCACAAGGACTTGAGTACTTG
CATAATGGATGCAAACCACCAATGGTTCATAGAGATGTCAAAACCACAAATATATTGCTGA
ACGAACACTTCCAAGCCAAACTAGCTGATTTTGGGCTTTCAAGGTCATTTCCAATTGAAGG
TGAAACTCATGTGTCAACAGTTGTTGCTGGAACGCCTGGATATCTTGATCCCGAATACTAT
AAAACAAATTGGTTGACAGAAAAGAGTGATGTTTATAGTTTTGGGATTGTATTGTTGGAGC
TTATCACAAATCGACCCGTGATCGACAAAAGCCGTGAAAAGCCACATATAGCAGAATGGGT
AGGAGTAATGCTTACAAAAGGAGACATCAACAGTATCATGGATCCTAATTTAAATGAAGAT
TATGATTCTGGTTCTGTTTGGAAAGCTGTTGAGCTAGCCATGAGTTGTCTCAATCCTTCTT
CAGCAAGAAGACCGACCATGTCCCAAGTTGTTATTGAACTAAACGAGTGTATAGCATCAGA
AAATTCAAGGGGAGGAGCGAGTCGGGATATGGACTCGAAGAGTTCCATAGAAGTGAGCTTG
ACCTTTGATACCGAACTGAGCCCAACGGCTCGGTAGTTTACATAAATTCATATTTCGCCA
TATGTAACGTGGATTTTTATTTATTTTCTATTTCATGTAATGAAATTTGTCTATGTGATAT
ATATCTTTGTTAATGAGCAATGAACTTCTTT

SEQ ID NO 7: At1g51850 deduced protein sequence

MERHCVLVATFLLMLHIVHAQDQIGFISVDCGLAPRESPYNEAKTGLTYTSDDGLVNVGKP
GRIAKEFEPLADKPTLTLRYFPEGVRNCYNLNVTSDTNYLIKATFVYGNYDGLNVGPNFDL
YFGPNLWTTVCLIKTGISIPFINVLELRPMKKNMYVTQGESLNYLFRVYISNSSTRIRFPD
DVYDRKWYPYFDNSWTQVTTTLDVNTSLTYELPQSVMAKAATPIKANDTLNITWTVEPPTT
KFYSYMHFAELQTLRANDAREFNVTMNGIYTYGPYSPKPLKTETIYDKIPEQCDGGACLLQ
VVKTLKSTLPPLLNAIEAFTVIDFPQMETNGDDVDAIKNVQDTYGISRISWQGDPCVPKLF
LWDGLNCNNSDNSTSPIITSLDLSSSGLTGSITQAIQNLTNLQELDLSDNNLTGEIPDFLG
DIKSLLVINLSGNNLSGSVPPSLLQKKGMKLNVEGNPHLLCTADSCVKKGEDGHKKKSVIV
PVVASIASIAVLIGALVLFFILRKKKSPKVEGPPPSYMQASDGRSPRSSEPAIVTKNRRFT
YSQVAIMTNNFQRILGKGGFGMVYHGFVNGTEQVAVKILSHSSSQGYKEFKAEVELLLRVH
HKNLVGLVGYCDEGENMALIYEYMANGDLKEHMSGTRNRFTLNWGTRLKIVVESAQGLEYL
HNGCKPPMVHRDVKTTNILLNEHFQAKLADFGLSRSFPIEGETHVSTVVAGTPGYLDPEYY
KTNWLTEKSDVYSFGIVLLELITNRPVIDKSREKPHIAEWVGVMLTKGDINSIMDPNLNED
YDSGSVWKAVELAMSCLNPSSARRPTMSQVVIELNECIASENSRGGASRDMDSKSSIEVSL
TFDTELSPTAR

SEQ ID NO 8: At1g51830 DNA sequence

ATGACAGTTTTTTTTATAAACGATTGTGTCAGGTTCCCGGATGATGTGTATGACCGAAAAT
GGTACCCGATCTTCCAGAACTCATGGACGCAAGTAACTACGAATCTCAATGTAAATATTAG
CACTATTTATGAACTACCACAAAGCGTAATGTCAACAGCCGCGACGCCGCTAAATGCTAAT
GCGACCTTGAACATTACATGGACAATAGAGCCTCCTACTACACCATTTTACTCCTACATTC
ACTTTGCAGAGCTTCAATCTCTAAGGGCCAATGATACAAGAGAATTCAATGTGACGTTGAA
TGGGGAGTATACAATTGGACCTTATAGTCCTAAACCGCTAAAAACCGAAACCATACAAGAC

FIGURE 4E

TTAAGCCCCGAGCAATGTAATGGAGGGGCGTGTATTTTGCAGCTTGTGGAGACGCTGAAAT
CAACTCTTCCGCCTTTACTTAATGCTATTGAGGCTTTCACTGTGATTGATTTCCCGCAAAT
GGAGACAAATGAAGATGATGTTACTGGTATCAACGATGTTCAAAACACTTATGGATTGAAT
AGAATCAGTTGGCAAGGAGATCCATGTGTCCCCAAACAGTATTCGTGGACGGTCTAAATT
GCAACAACTCAGATATCTCTATACCACCAATAATCATTTCCTTAGATTTATCTTCAAGTGG
TTTAAATGGGGTCATTACACAAGGCATTCAAAATCTAACCCATCTTCAATACTTGGACTTG
TCAGATAATAATTTAACTGGTGATATACCTAAATTTCTAGCTGACATACAATCACTCTTGG
TTATAAACTTAAGTGGTAATAATCTCACTGGATCGGTGCCTCTCTCACTTCTTCAGAAGAA
AGGATTGAAATTAAATGTCGAAGGCAACCCTCATCTTCTTTGCACAGATGGTTTATGTGTT
AACAAAGGAGATGGACATAAGAAAAAGAGCATCATAGCACCAGTGGTCGCATCAATTGCTT
CAATAGCTATTCTTATAGGTGCATTGGTTCTGTTTTTTGTTCTTAAAAAGAAAACGCAATC
AAAAGAACCAGCAATAGTGACGAAGAATAAACGGTTTACTTACTCTGAAGTTATGCAAATG
ACAAATAACTTCCAAAGAGTGCTTGGGAAAGGAGGGTTTGGAATTGTTTATCATGGTTTGG
TGAATGGTACTGAACAAGTAGCTATTAAGATACTCTCCCATTCTTCATCTCAAGGATATAA
ACAATTCAAAGCTGAGGTAGAACTTCTTCTTAGAGTTCATCACAAGAATTTGGTAGGCCTT
GTTGGATACTGTGACGAAGGAGAGAACTTGGCTCTTATATATGAATACATGGCCAATGGAG
ATTTAAAAGAACACATGTCAGGAACACGAAACCACTTCATTTTAAATTGGGGAACTAGACT
AAAAATAGTCGTTGAATCTGCCCAAGGACTTGAGTATTTGCACAATGGATGCAAACCACTA
ATGGTGCATAGAGACATCAAAACAACAAATATATTGTTGAATGAACAATTTGATGCCAAAC
TTGCTGATTTTGGGCTCTCGAGATCATTCCCGATTGAAGGTGAAACTCATGTTTCAACAGC
TGTTGCTGGAACTCCTGGATATCTCGATCCCGAATACTACAGAACAAATTGGTTGACTGAA
AAGAGTGATGTTTATAGTTTCGGAGTCGTATTGTTAGAGATCATCACAAACCAACCCGTGA
TAGACCCAAGACGTGAAAAGCCACATATAGCAGAATGGGTTGGGGAAGTGCTTACAAAAGG
AGACATAAAAAATATAATGGATCCAAGTCTAAATGGAGATTATGATTCCACTTCTGTTTGG
AAAGCTGTTGAGCTAGCGATGTGTTGTCTTAATCCTTCATCAGCTAGAAGACCGAACATGT
CTCAAGTTGTTATTGAATTAAACGAGTGTTTGACATCTGAAAATTCAAGGGGAGGAGCGAT
TCGAGACATGGACTCAGAAGGTTCTATAGAAGTAAGCTTGACCTTTGGTACCGAAGTGACC
CCATTGGCTCGGTAG

SEQ ID NO 9: At1g51830 deduced protein sequence

MTVFFINDCVRFPDDVYDRKWYPIFQNSWTQVTTNLNVNISTIYELPQSVMSTAATPLNAN
ATLNITWTIEPPTTPFYSYIHFAELQSLRANDTREFNVTLNGEYTIGPYSPKPLKTETIQD
LSPEQCNGGACILQLVETLKSTLPPLLNAIEAFTVIDFPQMETNEDDVTGINDVQNTYGLN
RISWQGDPCVPKQYSWDGLNCNNSDISIPPIIISLDLSSSGLNGVITQGIQNLTHLQYLDL
SDNNLTGDIPKFLADIQSLLVINLSGNNLTGSVPLSLLQKKGLKLNVEGNPHLLCTDGLCV
NKGDGHKKKSIIAPVVASIASIAILIGALVLFFVLKKKTQSKEPAIVTKNKRFTYSEVMQM
TNNFQRVLGKGGFGIVYHGLVNGTEQVAIKILSHSSSQGYKQFKAEVELLLRVHHKNLVGL
VGYCDEGENLALIYEYMANGDLKEHMSGTRNHFILNWGTRLKIVVESAQGLEYLHNGCKPL
MVHRDIKTTNILLNEQFDAKLADFGLSRSFPIEGETHVSTAVAGTPGYLDPEYYRTNWLTE
KSDVYSFGVVLLEIITNQPVIDPRREKPHIAEWVGEVLTKGDIKNIMDPSLNGDYDSTSVW
KAVELAMCCLNPSSARRPNMSQVVIELNECLTSENSRGGAIRDMDSEGSIEVSLTFGTEVT
PLAR

FIGURE 4F

SEQ ID NO 10: At1g51805 DNA sequence

GAGAAATACCTCATATACATAATCATAAACTTATATGCATAGCTTTGCTAACTCAAAAAAA
AAAACAGATCCCTTCTTTGCATAGTAAGGAAGATATTAATGGAGAGTCATCGTGTGTTCGT
TGCCACTTTTATGCTGATACTTCATCTTGTTCAAGCTCAAGATCAACCCGGATTCATCAAT
GTGGATTGCGGTTTACTCCCTCGTGATTCTCCTTACAACGCACTCGGAACCGGTTTAGTAT
ATACATCAGATGTCGGTTTAGTTAGCAGTGGGAAAACTGGTAAAATCGCCAAGGAATTCGA
AGAGAACAACAGTACACCGAATTTGACATTGAGATACTTTCCAGACGGAGCACGAAACTGC
TACAACTTAAACGTGAGCCGTGACACCAACTATATGATCAAGGCTACATTCGTGTATGGAA
ATTACGATGGTCATAAAGATGAGCCGAACTTCGACCTTTACTTGGGTCCAAATTTATGGGC
AACGGTAAGCCGCAGTGAAACTGTTGAGGAGATCATCCATGTGACGAAATCCGATTCGTTA
CAGGTTTGTCTTGCTAAGACGGGAGATTTTATACCTTTTATTAATATCTTGGAGCTACGAC
CATTGAAGAAAAATGTGTACGTTACAGAAAGTGGCTCACTCAAGCTCTTATTTAGGAAGTA
TTTTAGTGACTCAGGTCAAACGATAAGGTATCCAGATGATATCTATGACCGTGTATGGCAT
GCATCCTTCCTGGAAAATAATTGGGCACAAGTATCGACGACTTTGGGTGTAAACGTTACTG
ATAATTATGATTTATCACAAGATGTAATGGCAACGGGCGCAACACCTCTAAACGATAGTGA
GACATTGAACATTACATGGAACGTAGAGCCTCCTACTACAAAGGTTTACTCCTACATGCAC
TTTGCAGAGCTTGAGACACTAAGGGCCAACGATACAAGGGAATTCAATGTGATGCTGAATG
GAAATGACTTGTTTGGACCTTACAGTCCAATACCGCTAAAGACCGAAACAGAAACCAACTT
AAAACCAGAGGAATGCGAAGATGGGGCATGTATTTTGCAGCTTGTGAAGACGTCAAAATCA
ACTCTTCCGCCTTTACTTAATGCTATAGAGGCTTTCACCGTGATTGATTTCCTACAAGTGG
AGACAGATGAAGATGACGCTGCTGCTATCAAGAATGTTCAAAATGCTTATGGATTGATTAA
TAGAAGCAGTTGGCAAGGAGATCCATGTGTCCCCAAACAGTATTCGTGGGACGGTCTAAAG
TGCAGTTACTCAGATAGTACTCCACCAATAATTAATTTCTTAGACTTATCTGCAAGTGGAC
TAACCGGGATCATCGCGCCTGCCATTCAAAATCTTACTCACCTAGAAATATTGGCCTTGTC
AAATAACAATTTGACCGGAGAAGTACCTGAATTTCTAGCTGACTTAAAATCAATCATGGTC
ATAGACTTAAGAGGCAATAACCTCAGTGGCCCGGTTCCTGCCTCACTTCTTCAGAAGAAAG
GATTGATGCTACATCTTGATGACAATCCCCATATTCTTTGCACAACTGGTTCATGTATGCA
CAAAGGAGAAGGCGAAAAAAAGAGTATCATTGTACCAGTGGTTGCATCAATTGTTTCATTG
GCTGTTATTATAGGTGCACTCATTCTGTTCCTTGTTTTCCGAAAGAAAAAGGCATCAAAAG
TTGAAGGGACACTACCATCTTACATGCAAGCATCAGATGGTAGATCGCCGAGATCCTCTGA
ACCAGCAATAGTGACGAAAAACAAAAGGTTTACTTACTCACAAGTTGTGATAATGACAAAT
AACTTCCAAAGAATCCTTGGGAAAGGAGGGTTTGGAATCGTTTATCATGGCTTTGTGAACG
GTGTTGAACAAGTAGCTGTTAAGATACTCTCTCATTCATCATCTCAAGGGTATAAACAATT
CAAAGCTGAGGTAGAACTTCTTCTTAGAGTTCATCACAAGAATTTGGTTGGTCTTGTTGGG
TATTGCGACGAAGGAGAGAACATGGCTCTTATCTATGAATACATGGCCAATGGAGATTTAA
AAGAACATATGTCAGGAACAAGAAACCGATTTATTTTAAATTGGGAAACTAGACTAAAAAT
AGTCATTGACTCTGCGCAAGGGCTTGAGTATTTGCATAATGGATGCAAACCACTAATGGTA
CACAGGGACGTCAAAACTACAAATATATTGTTAAATGAACACTTTGAAGCCAAACTTGCTG
ATTTTGGGCTTTCAAGGTCTTTTCCGATTGGAGGTGAAACTCATGTGTCAACAGTTGTTGC
TGGAACTCCTGGATATCTCGATCCTGAATATTACAAAACAAATCGGTTGACAGAGAAGAGT
GATGTATATAGTTTTGGGATTGTATTGTTGGAGATGATCACAAATCGGCCAGTGATAGACC
AAAGCCGTGAAAAGCCATATATTTCAGAATGGGTGGGGATAATGCTTACGAAAGGAGACAT
CATTAGCATTATGGATCCAAGTCTAAATGGAGACTATGATTCTGGTTCTGTGTGGAAAGCT
GTTGAACTAGCAATGTCTTGTCTGAATCCTTCTTCAACAAGAAGACCTACCATGTCTCAAG

FIGURE 4G

TTCTTATTGCATTAAACGAATGTTTGGTATCTGAAAATTCAAGGGGAGGAGCGAGTAGGGA
CATGGACTCAAAGAGTTCCCTAGAGGTAAGCTTGACATTTGATACTGATGTGAGCCCAATG
GCTAGGTAGATTACATGAAATATTATCATGCGGTATCACATAAATTTGTTTATATGTTTTT
ATTTACAGAACTATCCTCAAATTAGTATCTCTCTTATAGGCCACCTTTGTTAATGAACTCT
GAACTTTTTGTCATTGATACATGTGTGAATAACAGTCCAAAGTCTATTATTGTTCCGCCGT
AATGTATCAGTTTCAAATCAGTGCATTTTTTGTTTG

SEQ ID NO 11: At1g51805 deduced protein sequence

MESHRVFVATFMLILHLVQAQDQPGFINVDCGLLPRDSPYNALGTGLVYTSDVGLVSSGKT
GKIAKEFEENNSTPNLTLRYFPDGARNCYNLNVSRDTNYMIKATFVYGNYDGHKDEPNFDL
YLGPNLWATVSRSETVEEIIHVTKSDSLQVCLAKTGDFIPFINILELRPLKKNVYVTESGS
LKLLFRKYFSDSGQTIRYPDDIYDRVWHASFLENNWAQVSTTLGVNVTDNYDLSQDVMATG
ATPLNDSETLNITWNVEPPTTKVYSYMHFAELETLRANDTREFNVMLNGNDLFGPYSPIPL
KTETETNLKPEECEDGACILQLVKTSKSTLPPLLNAIEAFTVIDFLQVETDEDDAAAIKNV
QNAYGLINRSSWQGDPCVPKQYSWDGLKCSYSDSTPPIINFLDLSASGLTGIIAPAIQNLT
HLEILALSNNNLTGEVPEFLADLKSIMVIDLRGNNLSGPVPASLLQKKGLMLHLDDNPHIL
CTTGSCMHKGEGEKKSIIVPVVASIVSLAVIIGALILFLVFRKKKASKVEGTLPSYMQASD
GRSPRSSEPAIVTKNKRFTYSQVVIMTNNFQRILGKGGFGIVYHGFVNGVEQVAVKILSHS
SSQGYKQFKAEVELLLRVHHKNLVGLVGYCDEGENMALIYEYMANGDLKEHMSGTRNRFIL
NWETRLKIVIDSAQGLEYLHNGCKPLMVHRDVKTTNILLNEHFEAKLADFGLSRSFPIGGE
THVSTVVAGTPGYLDPEYYKTNRLTEKSDVYSFGIVLLEMITNRPVIDQSREKPYISEWVG
IMLTKGDIISIMDPSLNGDYDSGSVWKAVELAMSCLNPSSTRRPTMSQVLIALNECLVSEN
SRGGASRDMDSKSSLEVSLTFDTDVSPMAR

SEQ ID NO 12: At1g51810 DNA sequence

ATGGAGAGACATTGTTTGTTCTTTGTGATTTTTTCCCTTATACTACATCTTGTTCAAGCTC
AGGACCCAATAGGCTCTCCTTACAAAGAATCCTCGACCGGTCTAACATATACGTCAGACGA
TGGTTTCGTCCAGAGCGGGAAAATTGGTAAAATCACCAAGGAACTCGAGTCATTATACAAG
AAACCGGAGCGGACGCTAAGATACTTTCCTGATGGAGTAAGAAATTGTTTCAGTCTGAATG
TCACAAGGGGAACAAAGTATCTAATCAAGCCAACCTTTCTCTATGGAAACTATGATGGTCG
TAATGTCATCCCGGATTTTGATCTTTACATCGGCCCAAATATGTGGATCACGGTGAATACT
GATAACACTATCAAGGAGATCCTCCACGTATCGAAATCAAACACTTTGCAAGTGTGTCTTG
TTAAGACAGGTACAAGTATACCTTATATAAATACATTGGAACTACGACCATTGGCCGACGA
TATATACACCAACGAAAGTGGCTCCCTCAACTATCTTTTTCGGGTTTATTATAGCAATTTA
AAGGGCTATATAGAGTACCCCGATGATGTCCACGATCGCATATGGAAACAAATCCTACCTT
ACCAGGATTGGCAGATTTTAACTACGAATCTCCAAATAAACGTTTCTAATGATTATGATCT
ACCCCAACGTGTAATGAAAACAGCTGTAACACCCATTAAAGCTAGCACAACGACGATGGAA
TTTCCCTGGAACTTAGAGCCTCCAACTTCACAGTTTTACTTATTCCTTCACTTTGCAGAGC
TTCAAAGTCTACAAGCCAACGAGACGAGGGAATTCAATGTGGTGTTGAACGGAAATGTTAC
ATTTAAATCTTATAGTCCTAAGTTTTTAGAAATGCAAACAGTATATAGCACAGCACCAAAG
CAATGCGATGGAGGGAAATGCTTGTTGCAGTTAGTGAAAACGTCAAGGTCCACTTTGCCGC
CTCTAATTAATGCTATGGAGGCTTACACTGTGCTTGATTTCCCACAGATAGAAACAAATGT
AGATGAAGTGATTGCTATCAAGAATATACAATCTACTTATGGATTGAGTAAAACAACCTGG
CAAGGAGATCCATGTGTACCCAAAAAGTTCTTGTGGGATGGTTTAAACTGCAACAACTCGG

FIGURE 4H

ATGATTCTACGCCACCAATTATCACTTCCTTTGGATTGACTGGAATTATCGTGCTGACCAT
TCAGAATCTCGCCAATTTACAAGAACTGGACTTGTCAAATAACAACTTGTCTGGAGGTGTT
CCTGAATTTCTAGCGGATATGAAGTCGCTCTTGGTCATAAACTTAAGTGGGAACAATCTCA
GTGGTGTAGTTCCTCAAAAGCTTATAGAGAAGAAAATGTTGAAATTGAACATTGAAGGCAA
TCCGAAGCTTAATTGCACAGTGGAGTCATGTGTAAACAAAGATGAAGAGGGTGGACGACAG
ATAAAGAGCATGACAATCCCAATTGTGGCATCAATTGGTTCTGTTGTTGCCTTCACAGTTG
CATTGATGATATTTTGTGTTGTTCGAAAGAATAACCCGTCAAACGATGAAGCTCCAACATC
ATGTATGCTACCCGCGGATAGTAGATCATCTGAACCGACAATAGTGACGAAGAATAAAAAA
TTTACGTATGCGGAGGTTTTAACCATGACAAACAATTTCCAAAAAATCCTTGGAAAAGGAG
GATTTGGAATTGTATATTATGGTTCAGTAAACGGTACAGAGCAGGTTGCTGTGAAAATGCT
TTCCCATTCATCAGCTCAAGGATATAAGCAATTTAAAGCTGAGGTTGAACTTCTTCTTAGA
GTACATCACAAGAATTTGGTAGGCCTTGTCGGGTATTGCGAAGAAGGAGATAAATTGGCTC
TCATCTACGAATACATGGCCAATGGAGACTTAGATGAGCATATGTCAGGAAAACGAGGTGG
TTCTATATTAAATTGGGGAACAAGGCTAAAGATAGCTCTCGAGGCTGCACAAGGATTAGAG
TACTTGCATAATGGATGCAAACCCTTAATGGTTCATAGAGATGTTAAAACCACAAATATAT
TGTTGAATGAACATTTCGATACCAAACTTGCTGATTTTGGGCTTTCGAGATCATTCCCGAT
AGAAGGGGAAACTCATGTATCAACTGTTGTTGCTGGAACTATTGGTTACCTCGATCCCGAT
GATGTGTATAGTTTTGGAGTTGTATTATTGGTGATGATTACAAACCAACCCGTGATAGACC
AAAACCGCGAAAAGAGACATATAGCAGAATGGGTGGGAGGAATGCTTACGAAAGGAGACAT
CAAAAGTATTACTGATCCAAATCTCCTTGGAGATTATAATTCTGGTTCTGTTTGGAAAGCT
GTTGAACTAGCAATGTCATGTATGAATCCTTCTTCGATGACAAGACCGACAATGTCTCAAG
TTGTTTTTGAACTGAAAGAGTGTTTGGCCTCTGAAAGCTCCAGGGAAGTGAGCATGACCTT
CGGAACTGAAGTGGCCCCTATGGCTCGGTAG

SEQ ID NO 13: At1g51810 deduced protein sequence

MERHCLFFVIFSLILHLVQAQDPIGSPYKESSTGLTYTSDDGFVQSGKIGKITKELESLYK
KPERTLRYFPDGVRNCFSLNVTRGTKYLIKPTFLYGNYDGRNVIPDFDLYIGPNMWITVNT
DNTIKEILHVSKSNTLQVCLVKTGTSIPYINTLELRPLADDIYTNESGSLNYLFRVYYSNL
KGYIEYPDDVHDRIWKQILPYQDWQILTTNLQINVSNDYDLPQRVMKTAVTPIKASTTTME
FPWNLEPPTSQFYLFLHFAELQSLQANETREFNVVLNGNVTFKSYSPKFLEMQTVYSTAPK
QCDGGKCLLQLVKTSRSTLPPLINAMEAYTVLDFPQIETNVDEVIAIKNIQSTYGLSKTTW
QGDPCVPKKFLWDGLNCNNSDDSTPPIITSFGLTGIIVLTIQNLANLQELDLSNNNLSGGV
PEFLADMKSLLVINLSGNNLSGVVPQKLIEKKMLKLNIEGNPKLNCTVESCVNKDEEGGRQ
IKSMTIPIVASIGSVVAFTVALMIFCVVRKNNPSNDEAPTSCMLPADSRSSEPTIVTKNKK
FTYAEVLTMTNNFQKILGKGGFGIVYYGSVNGTEQVAVKMLSHSSAQGYKQFKAEVELLLR
VHHKNLVGLVGYCEEGDKLALIYEYMANGDLDEHMSGKRGGSILNWGTRLKIALEAAQGLE
YLHNGCKPLMVHRDVKTTNILLNEHFDTKLADFGLSRSFPIEGETHVSTVVAGTIGYLDPD
DVYSFGVVLLVMITNQPVIDQNREKRHIAEWVGGMLTKGDIKSITDPNLLGDYNSGSVWKA
VELAMSCMNPSSMTRPTMSQVVFELKECLASESSREVSMTFGTEVAPMAR

FIGURE 4I

SEQ ID NO 14: At2g04300 DNA sequence

ATGAAAACACATCCTCAAGCAATTCTCTTATGTGTGTTATTCTTCATCACGTTTGGTCTTT
TACATGTCGTTGAAGCTGGAAATCAAGAAGGATTCATCAGTTTAGATTGTGGGTTATCCCC
CAATGAACCTCCTTACGTCGATGCTGCAACCGACTTAACATACACAACGGACAATGATTTC
GTGCAGAGCGGTAAAACTGGTACAATCGATAAGGAATTGGAGTCAACCTACAACAAACCAA
TTTTACAGCTTAGGTACTTCCCCGAAGGAGTCCGAAACTGTTATACCTTGAACGTCACGCT
CGGCACAAACTACCTGATCAGAGCCAGTTTCGTGTATGGTAACTACGATGGTCTTAATAAA
GAACTCGAGTTTGACCTTTACCTTGGTCCTAATCTATGGGCAAACGTGAACACAGCTGTAT
ATTTAATGAACGGAGTGACCACAGAAGAAATCATCCACAGTACCAAATCTAAGGTACTCCA
GGTTTGTCTTATTAAGACAGGCGAGAGTATACCTATTATTAATAGCTTAGAGCTGCGACCA
CTTATAAACGATACTTACAATACTCAAAGTGGCTCGCTGAAATACTTATTTCGGAATTATT
TCAGCACTTCAAGGAGAATAATACGGTACCCGAATGATGTCAACGATCGTCATTGGTATCC
GTTCTTTGATGAGGATGCGTGGACAGAATTGACTACAAATCTCAATGTTAACAGTTCAAAT
GGTTATGATCCACCAAAATTTGTAATGGCTTCAGCCTCAACACCCATAAGTAAAAATGCGC
CCTTCAACTTCACCTGGTCATTGATTCCTTCTACGGCCAAATTTTATAGTTACATGCACTT
CGCCGATATTCAGACTCTACAGGCCAATGAAACCCGAGAATTCGACATGATGTTGAATGGA
AACCTTGCCTTGGAACGTGCCCTCGAGGTTTTCACCGTGATCGATTTCCCCGAATTGGAAA
CAAATCAAGATGATGTTATTGCTATCAAGAATATCCAAAATACTTATGGAGTGAGTAAAAC
TAGCTGGCAAGGAGATCCATGTGTTCCTAAACGGTTTATGTGGGATGGCTTAAACTGCAAC
AACTCGTATATTTCCACACCACCTACAATAACTTTTTTAAACCTATCATCAAGTCATTTAA
CGGGGATCATTGCATCTGCCATTCAAAACCTAACCCACCTGCAAAATTTGGACTTGTCAAA
TAACAATTTGACAGGAGGAGTACCCGAGTTTCTTGCTGGCTTAAAATCACTCTTAGTCATA
AACTTAAGTGGGAATAATCTTAGTGGTTCTGTTCCTCAAACCCTTCTCCAGAAGAAAGGAC
TTAAGTTAAATCTTGAAGGAAATATTTATCTTAATTGTCCGGATGGATCATGTGTAAGCAA
AGACGGAAATGGAGGTGCCAAGAAAAAGAATGTTGTAGTATTGGTTGTGGTATCAATTGCA
CTTGTAGTAGTTCTTGGATCTGCATTAGCTCTTTTTTTGGTGTTTAGAAAAAGAAAAACAC
CACGCAATGAAGTTTCTAGAACATCTAGATCATTAGACCCGACAATAACGACGAAAAACAG
AAGATTTACTTATTCGGAAGTTGTAAAGATGACAAATAATTTTGAGAAAATCCTTGGTAAA
GGAGGGTTTGGAATGGTCTATCATGGAACTGTGAATGATGCTGAACAAGTAGCCGTTAAAA
TGTTATCACCCTCATCATCTCAAGGGTATAAAGAATTCAAAGCAGAGGTAGAACTCCTTCT
CAGAGTTCACCATAAAAATTTGGTTGGCCTCGTTGGATATTGTGATGAAGGAGAAAATTTA
TCTCTCATCTACGAGTACATGGCTAAAGGAGATCTTAAAGAACATATGTTAGGAAACCAAG
GTGTATCTATTTTGGACTGGAAAACTAGACTAAAGATAGTGGCCGAGTCCGCGCAAGGGCT
GGAATACTTGCATAATGGATGCAAACCACCAATGGTACATAGAGATGTCAAAACCACAAAT
ATATTGTTGGATGAACATTTTCAGGCCAAGCTTGCTGATTTCGGTCTTTCGAGATCTTTTC
CTCTTGAAGGAGAAACCCGTGTGGACACAGTTGTTGCTGGAACTCCTGGGTACCTTGATCC
AGAATATTATCGAACAAATTGGTTGAACGAGAAAAGTGATGTTTATAGCTTTGGAATCGTA
CTATTAGAGATCATCACAAACCAACATGTGATCAACCAAAGTCGTGAAAAACCACATATAG
CTGAATGGGTTGGGGTGATGCTTACAAAAGGAGACATCAAAAGCATTATAGATCCAAAATT
TAGTGGAGATTATGATGCTGGTTCTGTCTGGAGAGCAGTTGAACTAGCAATGTCGTGTGTA
AATCCTTCTTCAACTGGAAGACCAACCATGTCTCAAGTTGTAATCGAATTAAATGAATGTT
TGGCATCAGAAAACTCAAGGAGAGGAATGAGTCAAAACATGGAGTCAAAGGGATCTATCCA
ATATACAGAAGTCAGCACGAACTTTGGTACTGAATATACCCCTGAAGCTCGCTAGGCTGCA
TGAGCCATCTATCTTTTGTTTTATTTGTGTGTGTTTTTTTAATAAATAAATTGAATGTTT
GTAATGAGTTTTTGTAATTAATAAATGTGATTTTT

FIGURE 4J

SEQ ID NO 15: At2g04300 deduced protein sequence

MKTHPQAILLCVLFFITFGLLHVVEAGNQEGFISLDCGLSPNEPPYVDAATDLTYTTDNDF
VQSGKTGTIDKELESTYNKPILQLRYFPEGVRNCYTLNVTLGTNYLIRASFVYGNYDGLNK
ELEFDLYLGPNLWANVNTAVYLMNGVTTEEIIHSTKSKVLQVCLIKTGESIPIINSLELRP
LINDTYNTQSGSLKYLFRNYFSTSRRIIRYPNDVNDRHWYPFFDEDAWTELTTNLNVNSSN
GYDPPKFVMASASTPISKNAPFNFTWSLIPSTAKFYSYMHFADIQTLQANETREFDMMLNG
NLALERALEVFTVIDFPELETNQDDVIAIKNIQNTYGVSKTSWQGDPCVPKRFMWDGLNCN
NSYISTPPTITFLNLSSSHLTGIIASAIQNLTHLQNLDLSNNNLTGGVPEFLAGLKSLLVI
NLSGNNLSGSVPQTLLQKKGLKLNLEGNIYLNCPDGSCVSKDGNGGAKKKNVVVLVVVSIA
LVVVLGSALALFLVFRKRKTPRNEVSRTSRSLDPTITTKNRRFTYSEVVKMTNNFEKILGK
GGFGMVYHGTVNDAEQVAVKMLSPSSSQGYKEFKAEVELLLRVHHKNLVGLVGYCDEGENL
SLIYEYMAKGDLKEHMLGNQGVSILDWKTRLKIVAESAQGLEYLHNGCKPPMVHRDVKTTN
ILLDEHFQAKLADFGLSRSFPLEGETRVDTVVAGTPGYLDPEYYRTNWLNEKSDVYSFGIV
LLEIITNQHVINQSREKPHIAEWVGVMLTKGDIKSIIDPKFSGDYDAGSVWRAVELAMSCV
NPSSTGRPTMSQVVIELNECLASENSRRGMSQNMESKGSIQYTEVSTNFGTEYTPEAR

SEQ ID NO 16: At3g21340 DNA sequence

ATGGAGTACCATCCTCAAGCAATTAGGTTATGTGCGTTGATCTTCATCTCTTTCTATGCTC
TTTTACACCTCGTTGAAGCACAAGACCAAAAAGGATTCATTAGTTTGGATTGCGGGTCATT
GCCAAATGAGCCTCCTTACAACGATCCTTCAACCGGATTAACATACTCGACGGACGATGGT
TTCGTGCAGAGTGGCAAAACTGGAAGAATCCAGAAAGCGTTCGAGTCGATCTTCAGTAAAC
CGTCTTTGAAGCTTAGATACTTCCCGGACGGATTCCGAAACTGCTATACCTTGAATGTCAC
GCAAGACACAAACTATCTGATCAAAGCTGTATTTGTGTATGGTAACTACGATGGTCTTAAC
AATCCCCCGAGTTTCGATCTTTACCTTGGTCCGAATCTATGGGTAACGGTTGATATGAATG
GACGGACCAATGGTACTATCCAGGAGATTATCCACAAGACCATATCTAAGTCTCTCCAGGT
CTGTCTTGTTAAGACAGGAACAAGCTCACCTATGATTAATACGTTAGAGCTACGACCACTT
AAAAACAATACTTACAATACTCAGAGTGGCTCTCTGAAGTATTTCTTCCGATATTATTTCA
GCGGTTCAGGCCAAAACATACGGTACCCTGATGATGTCAATGATCGTAAATGGTATCCATT
CTTTGATGCAAAAGAGTGGACAGAGTTAACAACCAATCTGAATATAAACAGTTCTAATGGT
TATGCACCACCAGAAGTTGTGATGGCGTCAGCCTCAACGCCTATAAGTACTTTTGGAACAT
GGAACTTCTCATGGTTATTGCCATCTTCCACAACCCAATTTTATGTGTACATGCATTTTGC
CGAGATTCAAACTCTACGGTCCCTCGATACCCGAGAATTCAAAGTGACGTTGAATGGAAAA
CTTGCTTATGAACGCTACAGCCCTAAAACGTTAGCCACCGAAACCATTTTCTATTCGACAC
CACAACAATGTGAAGATGGGACATGCCTCTTGGAGTTGACGAAAACACCTAAGTCTACTCT
TCCTCCTCTCATGAACGCTCTTGAGGTTTTCACCGTGATCGATTTTCCACAGATGGAAACA
AATCCAGATGATGTTGCTGCTATCAAGAGTATCCAAAGCACTTATGGATTAAGTAAAATCA
GCTGGCAAGGAGATCCATGCGTTCCTAAACAGTTTTTGTGGGAGGGTTTAAACTGCAATAA
TCTAGATAACTCCACGCCGCCTATTGTCACTTCCTTAAACTTATCGTCAAGTCATTTAACG
GGGATCATCGCGCAAGGCATTCAGAATCTGACACACCTACAAGAACTAGACTTGTCAAATA
ACAATTTGACGGGAGGAATACCCGAATTTCTTGCTGACATAAAATCACTCTTAGTAATAAA
TTTAAGTGGGAACAATTTTAATGGCTCTATTCCTCAAATCCTTTTACAGAAGAAAGGACTA
AAGCTAATTCTTGAAGGAAACGCCAATCTGATTTGTCCGGATGGATTATGTGTAAACAAAG
CTGGCAATGGTGGTGCCAAGAAAATGAATGTTGTAATACCGATTGTTGCATCAGTTGCGTT
TGTGGTTGTTCTTGGATCTGCATTGGCGTTCTTTTTTATTTTCAAAAAGAAAAAGACATCA

FIGURE 4K

AACAGTCAAGAGTCGGCAATAATGACTAAGAACAGAAGATTTACATATTCGGAGGTTGTAA
CAATGACAAATAACTTTGAAAGAGTTCTTGGTAAAGGAGGATTTGGAATGGTTTATCATGG
AACTGTAAATAATACTGAACAAGTAGCCGTTAAAATGCTTTCACACTCATCTTCTCAAGGA
TATAAAGAATTCAAAGCAGAGGTGGAACTTCTTCTCAGAGTTCACCACAAAAATTTGGTTG
GCCTCGTTGGATATTGTGATGAAGGAGAAAACTTGGCTCTTATCTACGAGTACATGGCTAA
CGGAGACTTGAGAGAACATATGTCAGGAAAGCGAGGTGGATCTATTCTAAATTGGGAAACT
AGACTAAAAATAGTTGTCGAGTCTGCCCAAGGTTTGGAATACTTGCATAATGGATGCAAAC
CACCAATGGTTCATAGGGATGTTAAAACCACAAATATATTGTTGAATGAACACCTCCATGC
TAAGCTAGCTGATTTTGGGCTTTCGAGATCTTTTCCAATTGAAGGAGAAACTCATGTGTCA
ACAGTTGTTGCTGGAACTCCTGGATACCTTGATCCAGAATATTACCGAACAAATTGGTTGA
ACGAGAAAAGTGATGTTTATAGCTTTGGAATTGTACTATTAGAGATCATCACAAACCAACT
TGTGATCAATCAAAGTCGTGAAAAACCACATATAGCAGAATGGGTGGGGTTAATGCTTACA
AAAGGAGACATTCAAAACATTATGGATCCAAAACTTTATGGTGATTATGACTCTGGTTCTG
TCTGGAGAGCAGTTGAACTAGCAATGTCATGTCTAAATCCTTCTTCAGCTAGAAGACCAAC
AATGTCTCAAGTTGTTATCGAATTAAACGAATGTTTGTCATATGAAAACGCAAGAGGAGGA
ACGAGTCAAAACATGAACTCAGAGAGTTCAATAGAAGTCAGCATGAACTTTGATATTGGAG
CTACCCCTGATGCTCGTTAGACTGCAAGAGTCATTTTATCTTTGTTTTCTTGAGTGGATTT
TTGTTATTTTCAAAGGAAAA

SEQ ID NO 17: At3g21340 deduced protein sequence
MEYHPQAIRLCALIFISFYALLHLVEAQDQKGFISLDCGSLPNEPPYNDPSTGLTYSTDDG
FVQSGKTGRIQKAFESIFSKPSLKLRYFPDGFRNCYTLNVTQDTNYLIKAVFVYGNYDGLN
NPPSFDLYLGPNLWVTVDMNGRTNGTIQEIIHKTISKSLQVCLVKTGTSSPMINTLELRPL
KNNTYNTQSGSLKYFFRYYFSGSGQNIRYPDDVNDRKWYPFFDAKEWTELTTNLNINSSNG
YAPPEVVMASASTPISTFGTWNFSWLLPSSTTQFYVYMHFAEIQTLRSLDTREFKVTLNGK
LAYERYSPKTLATETIFYSTPQQCEDGTCLLELTKTPKSTLPPLMNALEVFTVIDFPQMET
NPDDVAAIKSIQSTYGLSKISWQGDPCVPKQFLWEGLNCNNLDNSTPPIVTSLNLSSSHLT
GIIAQGIQNLTHLQELDLSNNNLTGGIPEFLADIKSLLVINLSGNNFNGSIPQILLQKKGL
KLILEGNANLICPDGLCVNKAGNGGAKKMNVVIPIVASVAFVVVLGSALAFFFIFKKKKTS
NSQESAIMTKNRRFTYSEVVTMTNNFERVLGKGGFGMVYHGTVNNTEQVAVKMLSHSSSQG
YKEFKAEVELLLRVHHKNLVGLVGYCDEGENLALIYEYMANGDLREHMSGKRGGSILNWET
RLKIVVESAQGLEYLHNGCKPPMVHRDVKTTNILLNEHLHAKLADFGLSRSFPIEGETHVS
TVVAGTPGYLDPEYYRTNWLNEKSDVYSFGIVLLEIITNQLVINQSREKPHIAEWVGLMLT
KGDIQNIMDPKLYGDYDSGSVWRAVELAMSCLNPSSARRPTMSQVVIELNECLSYENARGG
TSQNMNSESSIEVSMNFDIGATPDAR

SEQ ID NO 18: At1g49100 DNA sequence
ATGGAGAAGTATTTTCATGGAGTTTTATGTGTGTTCATCATCACAGTTGCTTTTATACATG
TTGTTCAGGCTCAAGATCCAAACGGATTCATCACTTTGGATTGTGGTCTGTTACCTGATGG
ATCTCCATATACCAATCCATCTACTGGATTAACATTCACTTCGGATTCTAGTTTCATCGAG
AGTGGAAAGAATGGCCGAGTCAGTAAGGACTCTGAGCGAAACTTCGAAAAAGCTTTTGTAA
CTCTAAGATACTTTCCAGATGGAGAGCGGAACTGTTATAACCTGAATGTCACACAAGGAAC
AAATTACTTGATTAGAGCAGCTTTCTTATATGGAAATTACGATGGTCTTAATACTGTCCCA
AACTTTGATCTATTTATTGGCCCTAATAAGGTGACAACAGTGAATTTTAATGCAACCGGAG

FIGURE 4L

GTGGTGTGTTCGTGGAGATAATTCACATGTCAAGGTCAACCCCTTTGGATATTTGTCTTGT
TAAGACAGGAACAACTACACCGATGATATCAACCTTGGAGCTACGACCTTTGAGAAGTGAT
ACTTACATTAGTGCCATTGGGAGCTCCTTGCTCCTCTATTTTAGAGGTTATCTTAATGATT
CAGGTGTCGTTTTACGGTACCCCGATGATGTCAACGACCGTAGATGGTTCCCATTCTCATA
TAAGGAGTGGAAAATTGTAACCACAACTCTCAATGTAAACACTTCAAATGGTTTTGATCTA
CCACAAGGTGCAATGGCATCGGCTGCAACCCGTGTTAATGATAATGGGACATGGGAATTTC
CATGGAGCTTAGAGGATTCTACCACACGGTTTCACATTTACCTTCACTTCGCAGAGCTTCA
AACTTTGTTAGCCAACGAGACTAGAGAATTCAATGTTTTGCTGAATGGAAAAGTTTATTAT
GGACCTTATAGTCCTAAAATGTTAAGTATAGATACTATGAGCCCCCAACCCGATTCGACAT
TGACATGTAAAGGAGGAAGTTGCCTCTTGCAGCTAGTGAAGACAACAAAGTCAACTCTTCC
TCCTCTCATCAATGCTATTGAACTTTTTACTGTTGTTGAGTTTCCTCAATCAGAAACAAAC
CAAGATGAAGTGATTGCTATCAAGAAGATCCAACTTACTTATGGATTGAGTAGAATTAACT
GGCAAGGAGATCCATGTGTCCCCGAGCAGTTTTTGTGGGCTGGTTTGAAGTGCAGCAATAT
TAATAGTTCCACTCCACCAACAATCACTTTCTTAAACTTGTCTTCAAGTGGACTAACCGGG
ATCATTTCACCTTCCATCCAGAATTTGACCCATTTACAAGAGTTGGATTTGTCAAATAACG
ACTTGACCGGGGATGTGCCTGAGTTTCTAGCTGACATAAAATCGCTCTTGATCATAAACTT
AAGTGGAAACAATTTTAGCGGTCAACTTCCTCAAAAGCTTATAGATAAGAAAAGACTGAAG
CTGAATGTTGAAGGAAACCCTAAGCTTCTTTGCACAAAAGGACCATGTGGAAATAAACCTG
GAGAAGGTGGACATCCCAAAAAGAGTATAATTGTACCGGTTGTCTCATCAGTTGCTTTAAT
AGCTATTCTTATAGCTGCATTGGTTTTGTTTTTGGTTCTTAGAAAGAAAAATCCATCAAGG
AGTAAAGAAAATGGTAGAACTTCAAGATCATCCGAGCCACCAAGAATAACAAAAAAGAAAA
AGTTTACTTACGTGGAAGTTACTGAAATGACAAATAACTTTAGAAGTGTTCTTGGGAAAGG
AGGGTTCGGTATGGTTTATCATGGATATGTAAATGGTAGAGAGCAAGTTGCTGTTAAAGTA
CTCTCACACGCTTCAAAACATGGCCATAAACAATTCAAAGCAGAGGTTGAACTTCTTTTGA
GAGTTCATCACAAGAATTTGGTAAGCCTAGTTGGATACTGCGAAAAAGGGAAGGAATTGGC
TCTTGTCTACGAATACATGGCTAATGGAGACTTAAAAGAGTTTTTCTCAGGGAAGCGTGGT
GATGATGTTTTAAGGTGGGAAACTAGATTACAAATAGCAGTGGAGGCCGCACAAGGTTTGG
AGTACTTGCATAAAGGATGTAGACCACCAATTGTTCATAGAGATGTCAAAACCGCAAACAT
ATTATTGGATGAACACTTCCAAGCCAAACTTGCTGACTTTGGGCTTTCGAGATCATTTCTA
AACGAAGGAGAAAGTCATGTCTCGACAGTTGTTGCAGGAACTATTGGTTACCTTGATCCAG
AATATTACAGAACAAATTGGTTGACAGAGAAGAGTGATGTGTATAGTTTTGGGGTCGTTTT
ATTGGAGATCATAACAAATCAGCGCGTGATTGAGCGGACTCGAGAAAAGCCACACATAGCA
GAATGGGTGAATTTAATGATTACCAAAGGAGATATTAGAAAAATTGTAGATCCAAATCTCA
AGGGAGATTACCATTCTGATTCTGTTTGGAAGTTTGTGGAGCTAGCAATGACTTGTGTAAA
TGATTCTTCAGCGACAAGACCGACCATGACTCAAGTTGTTACCGAACTAACCGAATGTGTA
ACTTTAGAAAACTCAAGGGGAGGGAAAAGTCAGAACATGGGTTCAACGAGTTCAAGCGAAG
TGACCATGACCTTTGATACCGAAGTGAACCCTGTGGCTCGCTAG

SEQ ID NO 19: At1g49100 deduced protein sequence

MEKYFHGVLCVFIITVAFIHVVQAQDPNGFITLDCGLLPDGSPYTNPSTGLTFTSDSSFIE
SGKNGRVSKDSERNFEKAFVTLRYFPDGERNCYNLNVTQGTNYLIRAAFLYGNYDGLNTVP
NFDLFIGPNKVTTVNFNATGGGVFVEIIHMSRSTPLDICLVKTGTTTPMISTLELRPLRSD
TYISAIGSSLLLYFRGYLNDSGVVLRYPDDVNDRRWFPFSYKEWKIVTTTLNVNTSNGFDL
PQGAMASAATRVNDNGTWEFPWSLEDSTTRFHIYLHFAELQTLLANETREFNVLLNGKVYY

FIGURE 4M

GPYSPKMLSIDTMSPQPDSTLTCKGGSCLLQLVKTTKSTLPPLINAIELFTVVEFPQSETN
QDEVIAIKKIQLTYGLSRINWQGDPCVPEQFLWAGLKCSNINSSTPPTITFLNLSSSGLTG
IISPSIQNLTHLQELDLSNNDLTGDVPEFLADIKSLLIINLSGNNFSGQLPQKLIDKKRLK
LNVEGNPKLLCTKGPCGNKPGEGGHPKKSIIVPVVSSVALIAILIAALVLFLVLRKKNPSR
SKENGRTSRSSEPPRITKKKKFTYVEVTEMTNNFRSVLGKGGFGMVYHGYVNGREQVAVKV
LSHASKHGHKQFKAEVELLLRVHHKNLVSLVGYCEKGKELALVYEYMANGDLKEFFSGKRG
DDVLRWETRLQIAVEAAQGLEYLHKGCRPPIVHRDVKTANILLDEHFQAKLADFGLSRSFL
NEGESHVSTVVAGTIGYLDPEYYRTNWLTEKSDVYSFGVVLLEIITNQRVIERTREKPHIA
EWVNLMITKGDIRKIVDPNLKGDYHSDSVWKFVELAMTCVNDSSATRPTMTQVVTELTECV
TLENSRGGKSQNMGSTSSSEVTMTFDTEVNPVAR

SEQ ID NO 20: CB631540.1

TGCACACCTATCCTTCATCTGATCCTCCCATGCATGGTATATAGTACCAGAACGCATGAAT
GCCCCAGAAAGTGTGAAAAATCGCTGGAACCATCTGCCAAAAACTGAAAATCGCCGATTTA
CATATGAGGAGCTTGAGAAGTATACTGATAACTTCAAACGCCTCATTGGACACGGAGGCTT
TGGACATGTTTACTATGGTTGTCTAGAAGAAAATATTGAGGTTGCTGTCAAGATACGATCT
GAATCATCATCACACGGGCTTGATGAGTTTTTGGCTGAGGTTCAGAGTTTGACAAAGGTGC
ATCACAGAAATCTGGTGTCTTTGGTTGGCTACTGTTGGGAGAATGATCATTTAGCACTTGT
TTACGAGTACATGTCTGGAGGCAATCTTTGTGACCATCTGAGAGGTAAAATTGGTGCTGAT
AAATCCTTAAATTGGGCAACACGTCTACGTATTCTAGTTGATGCTGGACAAGGCCTGGATT
ATCTACATAAGGGTTGTAACCTGCCAATTATTCATGGAGATGTTAAGACCAATAACATTCT
ATTGGGTCAAAATCTAAAAGCAAAAATAGGAGATTTTGGGCTTTCCAAAACATACCATAGC
GACACGCAGACTCACATATCAGCTACAGCAGCTGGATCCGTGGGATACATCGATCCAGAGT
ACTACAGCACTGGAAGGCTCACGGAGAGCAGTGATGTTTACAGCTTTGGTGTTGTTTTGCT
AGAGGTAGCCACAGGTGAGTCTCCCATAATACCTGGACATGGTCACATTGTTCAGCGTGTG
AAACAGAAGATTGTCACTGGCAATATC

SEQ ID NO 21: CB628137.1

CTTTTTTTAACATTGTACCAGAACAGTTTCTCACATAAACATCTTATTGTTGTGTTCCACA
CATTGAAGCAAACTATATATTGCAAGGAATTAAGCACTCCTATTTTGGTTCTGTCGAACCA
TCTTTGTTTATGAATACCTGTTGTATAAATTACTGCGTTTGTCATATCATTTTACACTTAT
AGCAGAGAATTGACGTGGCAAAGCCAGGCGCACGTACACTTTCTTCATCTTGGTGAAGGAC
CAAATTTTGACATGGAAGACGCGGTATCACTTGCTATGTTTTCGTGGTCGACCCTTTCCTC
ATGAGCGTCCTCCAAAGCTAGGCCTTCCTTAAGTTGTGCAACCACAGTGGCCATCACTGGT
CTTTGAGTAGCAACATCAGCAGTGCACCTCATGGCAGTGTCAACAACCTTCCACATAGAGC
TGACATTGTAGGCATCAAGACGCGAATCGGCAACTGAGCTGATATTGCCAGTGACAATCTT
CTGTTTCACACGCTGAACAATGTGACCATGTCCAGGTATTATTGGAGACTCACCTGTGGCT
ACCTCTAGCAAAACAACACCAAAGCTGTAAACATCACTGCTCTCCGTGAGCCTTCCAGTGC
TGTAGTACTCTGGATCGATGTATCCCACGGATCCAGCTGCTGTAGCTGATATGTGAGTCTG
CGTGTCGCTATGGTATGTTTTGGAAAGCCCAAAATCTCCTATTTTTGCTTTTAGATTTTGA
CCCAATAGAATGTTATTGGTCTTAACATCTCCATGAATAATTGGCAGGTTACAACCCTTAT
GTAGATAATCCAGGCCTTGTCCAGCATCAAC

FIGURE 4N

SEQ ID NO 22: CB631541.1 cttttttattttaaggtcttaccacatatcaattgtaacattgtaccagaacagtttctca
cataaacatattattgttgtgttccacacattgaagcaaactatatattgcaaggaattaa
gcactcctattttggttctgtcgaaccatctttgtttatgaatacctgttgtataaattac
tgcgtttgtcatatcattttacacttatagcagagaattgacgtggcaaagccaggcgcac
gtacactttcttcatcttggtgaaggaccaaattttgacatggaagacgcggtatcacttg
ctatgttttcgtggtcgaccctttcctcatgagcgtcctccaaagctaggccttccttaag
ttgtgcaaccacagtggccatcactggtctttgagtagcaacatcagcagtgcacctcatg
gcagtgtcaacaaccttccacatagagctgacattgtaggcatcaagacgcgaatcggcaa
ctgagctgatattgccagtgacaatcttctgtttcacacgctgaacaatgtgaccatgtcc
aggtattattggagactcacctgtggctacctctagcaaaacaacaccaaagctgtaaaca
tcactgctctccgtgagccttccagtgctgtagtactctggatcgatgtatcccacggatc
cagctgctgtagctgatatgtgagtctgcgtgtcgctatggtatgttttggaaagcccaaa
atctcctattttttgcttttagattttgacccaatagaatgttattggtcttaacatctcca
tgaataattggcag

**SEQ ID NO 23: NM_184176, *Oryza sativa* (japonica cultivar-group) putative serine/threonine-specific receptor protein kinase, mRNA**

ATGGAGCGTTCACTGCTGCCGTGGTTGCTTCTTCTTCTCTGCTTCGCCGACGGCGTATTCC
AATCTCGTGCACAGCCAGACAGCAAAGGTTTCATTAGCATAGACTGTGGTATCCAGCCGAA
CACGAGCTACGTGCACAACACGACCAAGATATCCTACGTCGCCGACGACGACTTCACCGAC
GGCGGCTCCAACTACAACGTTTCGCCGGAGTACATCAAACCGCAGCTCTCGCAGCGGTACT
ACAACTTGCGTGCCTTCCCCGACGGTGCGCGCAACTGCTACACGGCCCGGTCGCTGGCGCC
TGGGATCAAGTACCTCATCCGCGCCTCTTTCTTGTATGGCAACTACGACGGCCTCAACAAG
CTGCCGGTGTTTCATCTCTACATTGGCGTCAACTTCTGGACCATGGTGAACATCACGAGCC
TCGGCCTCGGCGGCTCTCGTTATGAGGAGGCCATCGTGGTGGTGCCCGATGACTTTGTGCA
GGTCTGCCTGATCAACACTGGCACCGGCACGCCCTTCATCTCCTCGCTGGAGCTGAGGCCT
CTGGACAAAAGGCTCTATCCGCAGGTGAACGCCACGCTGGGCCTCCTCCAGCTCAACCGCC
TCAACTTTGGCCCGACTGATAACAGCCTCGTCAGGTACCCAGATGACCCACATGACAGATT
TTGGGGAAACTGGGACAGCTATACATCGAGCTTATGGAAGGAGATATCCACGGCGTCGAGG
GTAGATAACTTAGACGGAGACATATTCGATGCGCCGACGGCGGTGATGCAGACGGCAGTGA
CGCCGCGCAACGCGTCAGGTAACATCTACTTCTTTTGGGAGCCTTGGCCGCAGCCAAACGA
CCCGACGCCGCCGTACACTGTCATCTTCCACTTCTCCGAGCTGGAGATCCTCACCAACAAC
GCCTCGCGCCAGTTCTACATCAATCTCAACGGCGAACCGTTGATCGATACTGCTTACGAGC
CGACATACCTTACAGCGAGATACTTATATGGCTTGGAGCCCCTTGAAAGAACCTCCAGGTA
CAATATCACCATCAACGCTACCGCCAACTCGACGCTGCCGCCGCTCATCAACGCCGCCGAG
ATTTTCTCGATCATCTCCACCGCAGTCATCGGCACGGACTCGCAGGATGCATCTTCCATGA
TGGCGATCAAGGACAAGTACCAAGTCAAGAAGAATTGGATGGGTGACCCGTGTATGCCAAA
GACATTTGCGTGGGACAAGCTGACCTGCAGCTATCCCAATTCGAGCGGTGCAAGAATCATA
AGCTTAAATCTGTCCTCCAGTGGTTTGAGTGCTGACATATCATCCGCTTTTGGGAATCTCA
AGGCTCTTCAATACTTGGATCTATCAAACAACAGTTTGACCGGCTCAATTCCGGATGTCCT
CTCACAATTACCTTCCTTGAGAGTTTTAGATCTGACAGGAAATCAACTCAGTGGATCAATT
CCATCTGGAATTCTCAAGAGGATTCAAGATGGCTCCTTAAATGTAAGATATGGAAATAATC

FIGURE 4O

CAAACCTATGCATCAACGGCAATTCATGCAAGGCAGCTAAAAAGAAGAGCAAGCTAGCCAT
CTACACAGTTATTCCTGCAGTTCTGGTTGTATTGATAGCATCAGTTACAACACTCTTTTGC
CTGCTGAGACGAAAAAAGCAAGGACCAATGAACAATTCTCTAGAGCAGCAAAACGAGATGT
CGACATCAACAAGCCACGTGCTGATAAATAGTGGATATGGTGACAATGTATCGCTGCGGCT
TGAGAACCGTCGGTTTACATATAAAGAACTAGAGAAGATAACCAACAAATTCAAACGAGTG
CTCGGACGGGGAGGGTTCGGATATGTCTACCATGGCTTCTTGGAGGATGGCACAGAAGTGG
CGGTCAAGTTGCGATCTGAATCCTCAAGCCAAGGTGCTAAGGAGTTCCTCATAGAGGCTCA
AATTTTGACCCGGATTCACCATAAGAATCTTGTATCTATGATCAGTTACTGCAAGGATGGG
ATATACATGGCTCTTGTCTACGAGTACATGCCAGAAGGAACCCTAGAAGAACATATTGTAG
GGGAAAACAAAAAAGGGAAAATACTTAACATGGAGAGAGAGGCTCAATATCGCATTGGAAT
CTGCACAAGGGATGTGAAGGCGACCAACATCCTACTAAACACAAGGTTGGAGGCAAAGATT
GCCGATTTTGGCTTGTCCAAGGCATCCAGCTATGACAACATCACCCATGTATCCACGAACG
CTCTCGTTGGCACACTTGGATATGTCGATCCAGAGTACCAGATGACAATGCAAGCAACAAC
AAAGAGCGATGTCTATAGCTTTGGCGTCGTCTTATTGGAGCTGGTCACTGGGAAGCCGGCT
ATCTTGCATGAACCAAACCCCATCAGCGTCATCCACTGGACACGACAACGTCTAGCACGGG
GTAACATCGAGGATGTTGTGGACACATGCATGCCTAGTGATTATGATGTAAATGGTGTGTG
GAAGGCTATGGACATTGCGTTCACGTGCACTGCACAAGCATCGACACAACGACTCACTATG
ACTGAAGTGGTGATGCAGTTGCAAGAGTGTCTCGAGCTTGAGGATGCACGTTGTGCTATTG
GCGATGCACACAACGAGTTCTACCCTGACCCTCGGAGCGACCACAATTTAAGTTATAACAC
GTATGTCTCGGACCGGTCCAACGATGTTTTAGAATGA

**SEQ ID NO 24 putative serine/threonine-specific receptor protein kinase [*Oryza sativa* (japonica cultivar-group)], deduced protein sequence of SEQ ID NO 23**

MERSLLPWLLLLLCFADGVFQSRAQPDSKGFISIDCGIQPNTSYVHNTTKISYVADDDFTD
GGSNYNVSPEYIKPQLSQRYYNLRAFPDGARNCYTARSLAPGIKYLIRASFLYGNYDGLNK
LPVFHLYIGVNFWTMVNITSLGLGGSRYEEAIVVVPDDFVQVCLINTGTGTPFISSLELRP
LDKRLYPQVNATLGLLQLNRLNFGPTDNSLVRYPDDPHDRFWGNWDSYTSSLWKEISTASR
VDNLDGDIFDAPTAVMQTAVTPRNASGNIYFFWEPWPQPNDPTPPYTVIFHFSELEILTNN
ASRQFYINLNGEPLIDTAYEPTYLTARYLYGLEPLERTSRYNITINATANSTLPPLINAAE
IFSIISTAVIGTDSQDASSMMAIKDKYQVKKNWMGDPCMPKTFAWDKLTCSYPNSSGARII
SLNLSSSGLSADISSAFGNLKALQYLDLSNNSLTGSIPDVLSQLPSLRVLDLTGNQLSGSI
PSGILKRIQDGSLNVRYGNNPNLCINGNSCKAAKKKSKLAIYTVIPAVLVVLIASVTTLFC
LLRRKKQGPMNNSLEQQNEMSTSTSHVLINSGYGDNVSLRLENRRFTYKELEKITNKFKRV
LGRGGFGYVYHGFLEDGTEVAVKLRSESSSQGAKEFLIEAQILTRIHHKNLVSMISYCKDG
IYMALVYEYMPEGTLEEHIVGENKKGKILNMEREAQYRIGICTRDVKATNILLNTRLEAKI
ADFGLSKASSYDNITHVSTNALVGTLGYVDPEYQMTMQATTKSDVYSFGVVLLELVTGKPA
ILHEPNPISVIHWTRQRLARGNIEDVVDTCMPSDYDVNGVWKAMDIAFTCTAQASTQRLTM
TEVVMQLQECLELEDARCAIGDAHNEFYPDPRSDHNLSYNTYVSDRSNDVLE

FIGURE 4P

**SEQ ID NO 25 NM_191038 *Oryza sativa* (japonica cultivar-group) receptor protein kinase-like, mRNA**

ATGGTGATCAGCTACAGCTGCTCGGCTGGTACCAAGCTGACATGGATATTGTCGTTGCTGC
TCATCCTGGTCGCGGCGACACAAGTCCATGGCGTGTCTCCTCCTGGGTTTTAAACGTCGA
CTGCGGATTGACAAATCGTAGTACTTACAATGACACCGACACAACTTTGACGTACGTTTCT
GACAGAGAATTTGTCGAGAGCGGCAAGAGCTACGATATTATGGCACAATACATGGCAGATG
CTACAAATGAACAAGAAAAAACGTTGAGAAGCTTCCCTGATGGCCAACGGAACTGTTATAC
ATTACCAACCAACAGTAGCAAGAAGTATCTCATCAGAGCCACCTTCACTTATGGAAACTAC
GATGGGCTCAACTCGTCAGAGAAGGGTTCTTTGTTTATCTTTGGACTCCATATCGGTGTCA
ACTTCTGGACGACGGTAAACTTGACAAAGTGGGATCCATCGAGCACGGTATGGAAAGAGGT
GATCACGGTTGCTCCGGACAAGTCCGTATCTGTCTGTCTGATAAACATGGGATCAGGAACT
CCCTTCATATCTACACTAGATCTTAGGCCCTTGCAAGACACAATGTATCCCTTCGTGAATG
CCTCAACGTCCGTCAGCTATTTTTCTCGGATAAGATTTGGATCGGTTGATGAATACATCAC
AAGATTCCCAACGGATCAGTATGATCGCTTCTGGGAGGGCTGGGTCTTTACCATGCACACC
TTTCCATGGGTTAATAAGAGTAGCAACGGCAAGGTGGCTGAACTTCCTAATATTGACACCT
TTGGGCTTCCTCCAGCCATTCTGGGAAGCGCTTCAACCATAAACGGAAACTTCTCTTGGCT
CAACATCAGCGTTAGTGCCAGTAACTCTCTCGCAACAGACCTAGAGCTTCTTCCAGTCTTT
CACTTTGTTGAACTCGGCAATAATGGTTCAAAGAGAATTTTTGACATCTACAATGTCGATG
AACCGCAAGCACTGTTCTCCAACTTCAGCCCACCGTCATTCCTGAGCTCCATGTTCCACAA
CTGGTTCTTGCGCAAAGGCAGAAGGGCATATTTTCAGCTTCGCAAGACCCCAGACTCACAG
CTACCACCTCTTATTAACGCATATGAGGTGTACTCCCGTGTCCAGGTGGAGAACTTCACCA
CTGCTTCAAGTGATGGGAAGTCAAGAAAATCAGAAGAAGAAGATTATGATATGTATGAAGA
GGAGACTCCCCTACATATCGACATCAGAAGGTTCACATATGCAGAGCTGAAGCTCATAACT
AACAATTTCCAATCAATCATTGGAAAAGGAGGTTTTGGTACTGTTTATCATGGCATACTGG
AAAATAATGATGAAGTAGCTGTTAAGGTTCTTGTGGAGACATCCATAGCAGAGTCAAAAGA
CTTTCTCCCTGAGAAACAACCAAATCTTAATGGGTACCGACATATAAAATCAAATCAAGGT
ACAAACCTTGTCAAAAGTTCATCACAAGAATCTTGTCGCTTTGTGGTATTTGCACTACCAT
GCACATATCGAATGGATTTCTATAATGCCATTAATGTAGCACACTTTGATGCAGGATATGA
CAGTTTGAATTGGGAAGAGCGACTTCACATTGCACTTGATGCTGCACAAGTAGGTCTGGAA
TACCTTCATGAATCATGCACCCCATCAATAGTTCACAGAGATGTGAAGACACCCAACATCC
TTCTGGACAAGAATCTGGTGGCCAAGATATCTGATTTTGGGCTTTCACGGGCTTTTAATGC
TGCTCACACGCATATATCTACTGTTGCTGCTGGCACTCTTGGTTACCTTGACCCTGAGTAC
CATGCCACTTTCCAGCTTACTGTTAAGACAGACGTTTACAGTTTTGGAATCGTCCTCTTGG
AGATTGTGACTGGTCAACCCCCGGTATTCATGGACCCTCAAACCGTCCACCTGCCAAATTG
GGTGCGACAAAAGATTGCTAATGGGAGCGTTCACGATGTTGTGGACAAGAAGCTGTTGGAT
CAGTATGATGCCACGCACCTGCAGACTGTGATAGACCTCGCCATGAACTGCCTCGAAAACG
CATCGATTGACAGGCCAAGCATGACCGAGGTTGTTTCCGTGCTTAAGGTGTGCTTGCCGAT
TTCAAGCGAGAGACAATCGGCAACTTCAACCCCTCGAAAGAAGAACGTCATGGATGCAGAG
ATTCCAAGACAGTTCCAGTTGATGATTTCTGGAGCTTCAACAACAAGCTACGAGGGCAGCT
CCTTTCAGTCTGGATATACCGGTGGGGTATCAGAAATAAGCCACATTTCTGGGCGGTGA

FIGURE 4Q

**SEQ ID NO 26 NP_915927.1 receptor protein kinase-like [*Oryza sativa* (japonica cultivar-group)]**

MVISYSCSAGTKLTWILSLLLILVAATQVHGVSPPGFLNVDCGLTNRSTYNDTDTTLTYVS
DREFVESGKSYDIMAQYMADATNEQEKTLRSFPDGQRNCYTLPTNSSKKYLIRATFTYGNY
DGLNSSEKGSLFIFGLHIGVNFWTTVNLTKWDPSSTVWKEVITVAPDKSVSVCLINMGSGT
PFISTLDLRPLQDTMYPFVNASTSVSYFSRIRFGSVDEYITRFPTDQYDRFWEGWVFTMHT
FPWVNKSSNGKVAELPNIDTFGLPPAILGSASTINGNFSWLNISVSASNSLATDLELLPVF
HFVELGNNGSKRIFDIYNVDEPQALFSNFSPPSFLSSMFHNWFLRKGRRAYFQLRKTPDSQ
LPPLINAYEVYSRVQVENFTTASSDGKSRKSEEEDYDMYEEETPLHIDIRRFTYAELKLIT
NNFQSIIGKGGFGTVYHGILENNDEVAVKVLVETSIAESKDFLPEKQPNLNGYRHIKSNQG
TNLVKSSSQESCRFVVFALPCTYRMDFYNAINVAHFDAGYDSLNWEERLHIALDAAQVGLE
YLHESCTPSIVHRDVKTPNILLDKNLVAKISDFGLSRAFNAAHTHISTVAAGTLGYLDPEY
HATFQLTVKTDVYSFGIVLLEIVTGQPPVFMDPQTVHLPNWVRQKIANGSVHDVVDKKLLD
QYDATHLQTVIDLAMNCLENASIDRPSMTEVVSVLKVCLPISSERQSATSTPRKKNVMDAE
IPRQFQLMISGASTTSYEGSSFQSGYTGGVSEISHISGR

SEQ ID NO 27 NM_191035.1 Oryza sativa (japonica cultivar-group) receptor protein kinase-like, mRNA

ATGCAGGCTCACAGCAGCCAGCAGGACACAATACAAGATGCATGCTGTCTTCTGCTGGTCA
TCCCCATCGAAAGCCGGTGCAATTCCGAAGTGTTAACAGACCTGCGCCCCTATCTGAAGGG
AAAAGAGGCAGCCACCGAAAGAATGTTTGCAGGTCTCTTCTACTGTCTGACAAAGTGGGCA
GAAGGGTTCACAAACATTGACTGTGGCTTCGTAGACGGCGAGAGTTACACGGACAGCACAA
CAAATTTAACATACGTACCTGATCATGAATTCGTTGAAGGCGGCACACACCATGAAGTTGT
GCCAAAGCTAATTAGTGGATCCACCGATGAGCAAGAGAAAACCTTGAGAAGCTTCCCTGAT
GGCCAACGCAACTGTTACACAATACCGTCCACTAGTGGTAAGAAGTATCTCATCAGAACAA
CCTTCACTTACGGAAACTACGATGGACTCAGGTCGTCAGAGAACGGTTCCTTATTTCTGTT
TGGACTCCACATCGGCGTCAACTTCTGGACAACGGTGAACTTGACAAAACAGGACTCATCA
GACACTATCTGGAAAGAGGTGCTCACGGTTGCTCCGGACGAGTTCATATATGTGTGCCTGG
TAAACTTTGGATCAGGAACCCCTTTCATTTCTGCATTGGAGTTGCGGCAATTGGATGATCC
AATGTACCCATTCCTGAATCTTTTTGTGTCTGTAAGCTACTTTACTCGAATGAGATTTGGG
GCAGTCGATGATTTCATCACAAGATATCCAACTGATCTCTTTGATCGTTTCTGGGAAGCAG
CCCAATGCTACTCCTATCCCTGGCTCAACCTGACCACCAACCAAACAGTGAACAAGCTCCC
AGGAAATGACAACTTCCAGGTGCCAACACTCATCGTCCAGAAGGCATCCACCATCAACAGC
GGTTTTTCATGGCTCAACATCAGCATAACGGCCGGTGATAACCTGAATGGCCAGAGCCTGG
AGCTTCTCCCGATCTTCCACTTTGCTGAGATAGAAAAGAACCGCCCAAATCGGACGTTCCA
AATCTATAGTGATGGCAACGAGCTGCACCAGGCCTTCTCACCGTCCTACTTGCAGGTGGAC
AGCGTGTACCTGAGGGACCGGTACCTACATGAGTCAGGTACAACTTTCACCCTGTGCAAGA
CAAACAGCTCGGAGCTCCCACCACTCATCAACGCCTTTGAGGCTTACTCGCTTGTTCGGAT
GGAAAACCTCACCACTGACACCATCGATGTCAGTTCCATGAAACAAGTAAAGACGCAGTAC
AATGTGCAACGAAGAAGTTGGAATGGAGATCCATGTTCTCCAAAAGAGTATACCTGGGAAG
GTGTGAAATGCAACTACTATGATGGCAAACAGAATCCCAGGATCATCCTAGTATTAGAAGG
AAATCCCATGTGCTCAAATATAAGTGAAAGCTACTGTGCCATGCAAGCAGATAAGGCGAAG
AAGAATACAGCAACATTGCTCATTGCAGTGATAGTTCCTGTTGTAGCTATTACACTTATGT
TATTTCTATGGATGCTCTGCTGTAAAGGAAAACCAAAAGAACATGATGATTATGATATGTA

FIGURE 4R

TGAAGAGGAAAATCCCCTGCATAGCGACACCAGAAGATTCACATATACAGAGTTGAGGACT
ATAACGAACAACTTCCAGTCTATCATTGGAAATGGAGGATTTGGTACAGTTTATCATGGCA
TATTGGGGAATGGAGAGGAAGTCGCAGTCAAGGTGCTTCGGGAGACATCTAGAGCCCTATC
AAAGGACTTCCTCCCTGAGGTGCAAACATTGTCAAAAGTTCATCACAAGAATCTCGTCACA
TTTTTAGGATATTGCCTAAACAAGAAATGCCTTGCCCTTGTGTACGATTTCATGTCTAGAG
GAAACTTACAAGAAGTTTTAAGAGGAGGACTGGAGTATCTACATGAATCATGCACCCCAGC
AATTGTTCACAGAGATGTAAAAACGGCAAACATACTTCTCGATGAGAATCTTGTGGCCATG
ATATCTGACTTTGGTCTTTCACGATCTTACACTCCCGCACACACACACATATCAACTATTG
CTGCCGGTACTGTTGGCTACCTTGACCCAGAGTACCATGCTACTTTCCAACTCACTGTGAA
AGCAGATGTCTACAGTTTTGGCATTGTCCTTCTAGAGATCATTACCGGCCAACCTTCGGTT
TTAGTGGACCCAGAACCAGTGCATCTACCAAACTGGGTACGCCAAAAGATTGCTAGAGGAA
GCATTCATGATGCTGTGGACAGTAGACTGATGCATCAGTATGATGCCACTTCTGTACAGAG
TGTCATAGACCTTGCCATGAACTGTGTGGGAAATGTGTCCATTGATAGGCCGAGCATGACC
GAAATTGTTATCAAGCTCAAAGAGTGCTTACTGGCAGGTACAGGTAAAAAGCAACTGGTGT
CTGGCTCCTATAAACAGAAGGACGCCATGGACGCTGGCATTGCAAGGCAGTTCCAGCTGCT
GATTTCTGGAGTTCCAATAGTAAGTAACGAGTGTATATCAGGTGGCATCACAGAATTAAGT
TATTATTCAGGAAGCTCAACCGTGGAACAAGTTGGTGCCTGA

SEQ ID NO 28 NP_915924.1 receptor protein kinase-like [Oryza sativa (japonica cultivar-group)]

MQAHSSQQDTIQDACCLLLVIPIESRCNSEVLTDLRPYLKGKEAATERMFAGLFYCLTKWA
EGFTNIDCGFVDGESYTDSTTNLTYVPDHEFVEGGTHHEVVPKLISGSTDEQEKTLRSFPD
GQRNCYTIPSTSGKKYLIRTTFTYGNYDGLRSSENGSLFLFGLHIGVNFWTTVNLTKQDSS
DTIWKEVLTVAPDEFIYVCLVNFGSGTPFISALELRQLDDPMYPFLNLFVSVSYFTRMRFG
AVDDFITRYPTDLFDRFWEAAQCYSYPWLNLTTNQTVNKLPGNDNFQVPTLIVQKASTINS
GFSWLNISITAGDNLNGQSLELLPIFHFAEIEKNRPNRTFQIYSDGNELHQAFSPSYLQVD
SVYLRDRYLHESGTTFTLCKTNSSELPPLINAFEAYSLVRMENLTTDTIDVSSMKQVKTQY
NVQRRSWNGDPCSPKEYTWEGVKCNYYDGKQNPRIILVLEGNPMCSNISESYCAMQADKAK
KNTATLLIAVIVPVVAITLMLFLWMLCCKGKPKEHDDYDMYEEENPLHSDTRRFTYTELRT
ITNNFQSIIGNGGFGTVYHGILGNGEEVAVKVLRETSRALSKDFLPEVQTLSKVHHKNLVT
FLGYCLNKKCLALVYDFMSRGNLQEVLRGGLEYLHESCTPAIVHRDVKTANILLDENLVAM
ISDFGLSRSYTPAHTHISTIAAGTVGYLDPEYHATFQLTVKADVYSFGIVLLEIITGQPSV
LVDPEPVHLPNWVRQKIARGSIHDAVDSRLMHQYDATSVQSVIDLAMNCVGNVSIDRPSMT
EIVIKLKECLLAGTGKKQLVSGSYKQKDAMDAGIARQFQLLISGVPIVSNECISGGITELS
YYSGSSTVEQVGA

**SEQ ID NO 29 NM_191040.1 *Oryza sativa* (japonica cultivar-group) receptor protein kinase-like, mRNA**

ATGGTTGACGGACGGAGAGGGTACCGCCAAACGATTAATCGGAATACGGACGATTTATCGG
AATTTGACGGATATTTAACAAAACTGTTACTTACAGGGAAGTGTGTCTGTGCAGGGTTTTT
AAACATCGACTGCGGATTGACAAATCGTAGTACTTATAATGACACCGACACAACTTTGACG
TACGTTTCTGACAGAGAATTTGTTGAGGGCGGCAACGGCAAGAGCTACGATATTATGGCAC
AATACATCGCAGATGCTACAAATGAACAAGAAAAAACGTTGAGAAGCTTCCCTGATGGCCA
ACGGAACTGTTATACATTACCAACCAACAGTAGCAAGAAGTATCTCATCAGAGCCACCTTC

FIGURE 4S

ACTTATGGAAACTACGATGGGCTCAACTCGTCAGAGAAGGGTTCTCTGTTTCTCTTTGGAC
TCCACATCGGCGTCAACTTCTGGGCAACGGTGAACTTGACAAACTGGGGTTCATCAGATAC
GATGTATAAAGAGGTGATCACAGTTGCTCCAGACAAATTCATATCCGTCTGTCTGATAAAC
TTGGGATCAGGAACTCCCTTCGTATCTACATTAGACTTGAGGGAATTGGATGGTGCAATGT
TCCCATTTCTGAATCTTTCTGTTTCAATCAGCCATTTGGCTCGACAAAGATATGGCTCGGT
CGATGATTACATCACGAGATATCCAACTGATCCCTTCGATCGTTTCTGGGAGGCAGCCCTA
CGCTACAAATTTCCCTTCCTCAACATGACCACCAACCAAGACGTGACAAAGCTTCCTGGAA
ATGACGACTTTCAGGTGCCGATGCCCATCCTTCAGAAGGCCTCAACCATAAGCAGCAATTT
CTCAGAGTTTAACGTCAGCGTGATATTTCCGGACAACATGAAAAACATCGACAACATCAAC
AACATCGACTACAGGAGCTTGGAGCTGCTACCAATCTTCCACTTTGCCGATATTGGAGGCA
ACAACCAGAATAGAACGTTTGATATCTATAACGATGGAAACCTGATGTTTCCCAACTACAT
ACCACCCCTGTTCCGAGCGGAGAGCACATATCAGAGTGGTAAGTTCTTGCGCAAGAGGGGC
CTCAACTTCACCCTGCGCAAGACGCCCAGCTCGGAGCTCCAGCCGCTCATCAACGCATTCG
AGGTGTACTCGCTTGTTCATACAGACAACCTCACCACTTCTCCAGACGACGTTGATTACAT
GAAAGAAGTGAAGAAGTACTACAGTTACACAAGAAACTGGAATGGAGATCCATGCTCCCCA
AGAGAGTATTCCTGGCAAGGTCTGGCTTGCGACTACGCTAATGGAAACAAAAATCCAAGGA
TCACCCGAATGGATTTATCGCACAACAACTTGACAGGCGCAATTCCAGACTATCAACTCAA
TTCACTCAGAGTGCTTGATAGTTCCTGTGGTATCCCTCCTACTCCTTGTACTGGTTTGTAT
CCTCTGGAGGCTGTGCTGGAAAGGTTGGAGTTTGCAGGAAAATCAGCAGAACAAGAAGATT
ATTCTATTTATGAAGAGGAAGCTCCATTACATATCGACATCAAACGGTTCACATATGCAGA
GCTGAAGCTCATAACTAACAACTTCCAATCAATCATTGGAAAAGGAGGTTTTGGCACTGTT
TATCATGGCATACTGGAAAATAACGATGAAGTAGCTGTTAAGGTGCTTGTGGAGACATCTA
TAGCAGAGTCAAAAGACTTCCTCCCTGAGAGGAAATCTTCAGCTGTCATGGTCGGGATAAC
ATATCAACGCAGAAGCCGCACAGGGCTGCAGGATACGGCGTCAGGAGATGCAGCGCAGCGC
ACTACTAATTTCGCACACTTTGATGCAGGATATGATAGTAGTTTGAATTGGGAAGAACGAC
TTCACATTGCACTTGATGCTGCACAAGGACTGGAGTATCTACATGAATCATGCAGCCCGTC
AATAGTTCACAGAGATGTGAAGACACCCAACATCCTTCTGGACAAGAATCTGGTGGCCAAG
ATATCTGATTTTGGGCTTTCACGGGCTTTTAATGCAGCTCACACGCATATATCTACTGTTG
TTGCCGGCACCCTTGGTTACCTTGACCCTGAGTATCATGCTACTTTCCAACTTACCGTTAA
GACAGACGTTTACAGTTTTGGAATTGTCCTCTTGGAGATTGTCACTGGTCAACCCCCAGTA
TTTATGGATCCCCAAACCGTCCACTTGCCAAATTGGGTGCGGCAAAAGATTGATAAGGGAA
GCATCCACGATGTTGTGGACAAGAAACTGTTAGATCAATACGATGCCACTCACCTGCAAAC
TGTGATAGACCTTGCAATGAACTGCCTTGAAAACACATCAATTGACAGGCCAAGCATGACT
GAGGTTGTTTCTGTGCTTAAGGTGTTGTTTACGGTGGCTATTTCAAGTGAGAAACGATCGG
TTACATCAACCCCTCAAGAGAAGAACGTCATGGATGCAGACATTCCACGGCAGTTCCACTT
GATGATTTCTGGAGCTACAACAACAAGCTACGACAACGAGGGCAGTTCCTCACAGTCTGGT
CCTACCGGTGGGATGTCAGAAATAAGCTACATTTCTGGACGGTGA

**SEQ ID NO 30 NP_915926.1 receptor protein kinase-like [*Oryza sativa* (japonica cultivar-group)]**

MLHSRNPDTTTPPARRGKKTRSLASQGCTAFFSQTQLLVTRSRNTSFESKKLPSNYQKNNG
SSKRSSLKVFLYAGFLSIDCGYTDSAGYDDKNTMLPYVSDKGYIKGGKTFSILSQYMKEAA
NKQEETLRSFPDGQRNCYTLPTNRSKKYLIRATFTYGNYDGRNSSESGSPFLFGLHIGINF
WTMVNLTKLPSSNTIWKELIMVAPGNSVSVCLINNELGTPFISTLDLRPLQDTMYPFVNVS

FIGURE 4T

VAVSYFSRQRYGQVNDVITRYPEDVYDRFWEGAFHTRSYPWINLNTTQEVKRLPGDEKFMV
PNTILQKASTINITFSWLNITVRGANNLLGLGDLELLPVFHFAEIASNTTRLFDIYSDSEE
LFANFSPSPFQVDSMYQNGRFLPGVSSTFTLRKQPTSQPPLINAFEVYSLVRIATASDDGE
QNSGLNSDIFVYTLYSRAKWIEPFVNCDLAGKSKEHDDYDMYEEDTPLHTDTRRFTYTELK
TITNNFQSIIGKGGFGMVYHGILDNGEEVAVKVQILSKVQHKNLVTFLGYCHNKKCLALVY
DFMARGNLQEVLRGGLEYLHESCTPPIVHRDVKTANILLDKNLVAMISDFGLSRSYTPAHT
HISTVAAGTVGYLDPEYHATFHLTVKADVYSFGIVLLEIITGQPSVLVDSEPVHLPNWVRQ
KIAEGSIHDAVDSRLRHQYDATSIQSVIDLAMSCVENTSTDRPSMTDIVIKLKECLPAGTG
EMQLVSRSYKQKEAMDADIARQFQLLISGVSIESIEGNSSGTTELRYPSGR

**SEQ ID NO 31 NM_191037.1 *Oryza sativa* (japonica cultivar-group) receptor protein kinase-like, mRNA**

ATGTTGCATTCCAGAAATCCTGACACCACCACTCCACCAGCTCGAAGGGGAAAAAAAACTC
GCAGCCTCGCGTCGCAGGGCTGCACAGCTTTCTTCTCACAGACACAGTTACTAGTAACCCG
CAGTAGGAACACCAGCTTTGAATCTAAAAAACTTCCATCCAATTATCAGAAAAACAACGGA
AGCAGCAAACGGAGCTCTCTTAAAGTGTTTTTATATGCAGGGTTTTTAAGCATCGACTGCG
GATATACAGATAGTGCTGGCTATGACGACAAGAACACAATGTTGCCATATGTCTCTGACAA
AGGATATATAAAGGGCGGCAAGACCTTCAGTATTCTGTCACAGTACATGAAAGAAGCTGCA
AATAAGCAAGAAGAAACCCTGAGAAGTTTCCCTGATGGCCAACGGAACTGTTATACATTAC
CAACCAACCGTAGCAAGAAGTATCTCATCAGAGCCACCTTCACTTACGGGAACTACGATGG
CCGCAACTCATCAGAGAGTGGTTCACCGTTTCTCTTTGGACTCCATATCGGCATCAACTTC
TGGACAATGGTGAACCTGACAAAATTGCCTTCATCGAACACAATCTGGAAAGAGCTGATCA
TGGTTGCTCCAGGCAATTCCGTATCTGTTTGTCTGATAAACAACGAATTGGGGACTCCCTT
CATATCGACATTGGATTTGAGGCCCTTGCAAGATACAATGTACCCCTTTGTGAATGTTTCT
GTGGCCGTCAGTTATTTTTCTCGGCAAAGATATGGACAAGTCAATGATGTCATCACTAGAT
ATCCAGAGGATGTTTACGACCGGTTTTGGGAGGGAGCGTTCCACACCAGATCCTATCCCTG
GATCAACCTTAACACAACACAAGAAGTGAAAAGGCTCCCAGGTGATGAAAAGTTCATGGTG
CCGAATACCATCCTCCAGAAAGCTTCAACCATAAACATCACATTCAGTTGGCTCAACATCA
CTGTGAGGGGCGCCAACAACCTGCTTGGCTTGGGGGATCTGGAGCTGCTACCGGTCTTTCA
CTTTGCTGAGATAGCCAGCAACACGACCAGGTTGTTCGATATCTACAGCGACAGCGAGGAG
CTGTTCGCCAACTTCTCACCATCCCCCTTCCAGGTGGACAGCATGTACCAGAATGGCCGGT
TCTTGCCCGGTGTGAGCTCAACTTTCACGTTGCGCAAGCAGCCCACATCACAGCCACCGCT
CATCAACGCGTTCGAGGTGTATTCACTTGTCCGGATAGCTACTGCTTCTGATGATGGTGAA
CAAAACAGTGGGTTAAATTCAGATATTTTCGTGTATACACTATACAGTAGAGCAAAGTGGA
TTGAGCCATTTGTGAATTGTGACTTAGCAGGAAAATCAAAAGAACATGATGATTATGATAT
GTATGAAGAGGATACTCCCCTGCATACTGACACCAGAAGATTCACATATACAGAGTTGAAG
ACTATAACTAACAACTTCCAGTCTATCATTGGAAAAGGAGGATTTGGTATGGTTTATCATG
GCATATTGGACAATGGAGAGGAAGTGGCAGTCAAGGTGCAAATATTGTCAAAAGTTCAACA
CAAGAATCTCGTCACGTTTTTAGGATATTGCCACAACAAGAAATGCCTTGCCCTTGTGTAC
GATTTCATGGCTAGAGGAAACCTACAAGAAGTTTTAAGAGGAGGACTGGAGTATCTGCATG
AATCATGCACCCCGCCAATAGTTCACAGAGATGTGAAAACTGCAAACATTCTCCTGGATAA
GAATCTTGTGGCCATGATATCTGACTTTGGTCTTTCACGATCTTACACTCCAGCGCACACA
CACATATCAACTGTTGCTGCCGGTACTGTTGGCTACCTTGACCCTGAGTACCATGCTACTT
TCCACCTCACTGTGAAAGCAGATGTCTACAGCTTCGGCATTGTCCTCTTGGAGATCATTAC

FIGURE 4U

TGGCCAACCTTCAGTGTTAGTGGACTCAGAACCAGTGCACCTACCAAACTGGGTGCGCCAA
AAGATTGCTGAAGGGAGCATTCATGATGCTGTAGACAGTAGACTAAGGCATCAGTATGATG
CCACTTCCATACAGAGTGTCATAGATCTTGCCATGAGCTGTGTGGAAAACACATCCACTGA
TAGGCCAAGCATGACTGACATTGTTATCAAGCTCAAAGAATGCCTACCGGCAGGTACAGGT
GAAATGCAACTGGTGTCTAGGTCCTATAAACAGAAGGAAGCCATGGACGCTGACATAGCGA
GGCAATTCCAGCTGCTGATTTCTGGAGTTTCAATAGAAAGCATTGAGGGCAACTCAAGTGG
GACCACAGAATTAAGATATCCTTCGGGAAGGTGA

SEQ ID NO 32 NP_915929.1 receptor protein kinase-like [Oryza sativa (japonica cultivar-group)]

MVDGRRGYRQTINRNTDDLSEFDGYLTKLLLTGKCVCAGFLNIDCGLTNRSTYNDTDTTLT
YVSDREFVEGGNGKSYDIMAQYIADATNEQEKTLRSFPDGQRNCYTLPTNSSKKYLIRATF
TYGNYDGLNSSEKGSLFLFGLHIGVNFWATVNLTNWGSSDTMYKEVITVAPDKFISVCLIN
LGSGTPFVSTLDLRELDGAMFPFLNLSVSISHLARQRYGSVDDYITRYPTDPFDRFWEAAL
RYKFPFLNMTTNQDVTKLPGNDDFQVPMPILQKASTISSNFSEFNVSVIFPDNMKNIDNIN
NIDYRSLELLPIFHFADIGGNNQNRTFDIYNDGNLMFPNYIPPLFRAESTYQSGKFLRKRG
LNFTLRKTPSSELQPLINAFEVYSLVHTDNLTTSPDDVDYMKEVKKYYSYTRNWNGDPCSP
REYSWQGLACDYANGNKNPRITRMDLSHNNLTGAIPDYQLNSLRVLDSSCGIPPTPCTGLY
PLEAVLERLEFAGKSAEQEDYSIYEEEAPLHIDIKRFTYAELKLITNNFQSIIGKGGFGTV
YHGILENNDEVAVKVLVETSIAESKDFLPERKSSAVMVGITYQRRSRTGLQDTASGDAAQR
TTNFAHFDAGYDSSLNWEERLHIALDAAQGLEYLHESCSPSIVHRDVKTPNILLDKNLVAK
ISDFGLSRAFNAAHTHISTVVAGTLGYLDPEYHATFQLTVKTDVYSFGIVLLEIVTGQPPV
FMDPQTVHLPNWVRQKIDKGSIHDVVDKKLLDQYDATHLQTVIDLAMNCLENTSIDRPSMT
EVVSVLKVLFTVAISSEKRSVTSTPQEKNVMDADIPRQFHLMISGATTTSYDNEGSSSQSG
PTGGMSEISYISGR

SEQ ID NO: 33: consensus sequence, wherein x can be any amino acid and wherein up to 2 other amino acids may be replaced by a conserved substitution

LRxFP(E/D)GxRNC(Y/F)

FIGURE 4V

PLANTS HAVING IMPROVED GROWTH CHARACTERISTICS AND METHOD FOR MAKING THE SAME

RELATED APPLICATIONS

This application is a divisional application of U.S. application Ser. No. 11/632,570, filed May. 11, 2007 now U.S. Pat. No. 7,968,765, which is national stage application (under 35 U.S.C. 371) of PCT/EP2005/053397 filed Jul. 14, 2005, which claims benefit of European application 04103393.7 filed Jul. 15, 2004 and US Provisional application 60/589,235 filed Jul. 20, 2004. The entire content of each above-mentioned application is hereby incorporated by reference in its entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing__14546__00075_US. The size of the text file is 146 KB, and the text file was created on Jun. 27, 2011.

BACKGROUND OF INVENTION

The present invention relates generally to the field of molecular biology and concerns a method for improving plant growth characteristics. More specifically, the present invention concerns a method for increasing yield and/or biomass of a plant by increasing the expression and/or activity of an LRR receptor kinase (RLK827) or a homologue thereof in a plant. The present invention also concerns plants having increased expression of a nucleic acid encoding an LRR receptor kinase or a homologue thereof, which plants have improved growth characteristics relative to corresponding wild type plants. The invention also provides constructs useful in the methods of the invention.

Given the ever-increasing world population, and the dwindling area of land available for agriculture, it remains a major goal of agricultural research to improve the efficiency of agriculture and to increase the diversity of plants in horticulture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic complements that may not always result in the desirable trait being passed on from parent plants. Advances in molecular biology have allowed mankind to manipulate the germplasm of animals and plants. Genetic engineering of plants entails the isolation and manipulation of genetic material (typically in the form of DNA or RNA) and the subsequent introduction of that genetic material into a plant. Such technology has led to the development of plants having various improved economic, agronomic or horticultural traits. Traits of particular economic interest are growth characteristics such as high yield. Yield is normally defined as the measurable produce of economic value from a crop. This may be defined in terms of quantity and/or quality. Yield is directly, dependent on several factors, for example, the number and size of the organs, plant architecture (for example, the number of branches), seed production and more. Root development, nutrient uptake and stress tolerance may also be important factors in determining yield. Crop yield may therefore be increased by optimising one of the abovementioned factors.

Growth and development of plants is determined by environmental and internal signals, such as hormone mediated signalling, stress and nutrient signalling, cell cycle control or developmental signalling. Cells perceive these signals via cell surface receptors, which transduce the signal to the inside of the cell. Many of these receptors are protein kinases. Protein kinases comprise a large family of enzymes that mediate the response of eukaryotic cells to stimuli by phosphorylation of hydroxyamino acids. The enzymes fall into two broad classes with respect to their substrate specificity: serine/threonine specific or tyrosine specific enzymes. Kinases involved in signal transduction may be classified into different families which are mostly made up of tyrosine kinases. Receptor Tyrosine Kinases (RTK) in animals have a uniform structure and are composed of an extracellular ligand binding domain, a transmembrane domain and a cytoplasmic tyrosine kinase domain. Among the plant tyrosine kinases, the Receptor-Like Kinase (RLK) proteins take a prominent place. More than 600 different RLKs are known in plants. They have a similar structure as the animal RTKs, a classification is given in FIG. 1 (Shiu and Bleecker, Proc. Natl. Acad. Sci. USA 98, 10763-10768, 2001). Several plant RLK proteins have been characterised, for example BRH (brassinoid signalling), CLV1 (meristem differentiation), HAESA (abscission of floral organs), XA21 (fungal detection) CR4 (leaf and endosperm development), FLS2 (flagellin/pathogen detection), SRK (self-incompatibility), among others (Becraft, Annu. Rev. Cell Dev. Biol. 18, 163-192, 2002; Dievart and Clark, Curr. Opin. Plant Biol. 6, 507-516). About 200 of the plant RLKs possess a Leucine Rich Repeat (LRR). LRRs are sequence motifs of 23 to 25 residues, which comprise a consensus sequence LxxLxLxxN/CxL wherein x may be any amino acid. These LRRs are present in proteins with diverse functions, such as hormone receptor interactions, enzyme inhibition, cell adhesion and cellular trafficking and frequently the LRR domains are organised in tandem arrays. It was shown that LRRs may be critical for the morphology and dynamics of the cytoskeleton. The primary function of these motifs appears to be providing a versatile structural framework for the formation of protein-protein interactions (Kobe and Kajava, Curr. Opin. Struct. Biol. 11, 725-732, 2001).

The combination of Leucine Rich Repeats and kinase domains is characteristic for receptor proteins that mediate external signals into the cell. They are thought to act by a mechanism in which the LRR domain(s), mostly extracellular, act as a sensor for an extracellular signal whereas the kinase domain is usually internal and participates in the transduction of the signal by phosphorylating intracellular targets and thus initiating the signal transduction. RLKs have been implicated in plants in a variety of process like plant development, disease resistance or self-incompatibility. It is shown in this invention that plant growth characteristics, and in particular yield, may be improved by modulating expression in a plant of a nucleic acid encoding an RLK.

International patent application WO 03/072763 disclosed a receptor like kinase which, when overexpressed in plants, resulted in increased plant growth and seed production. However, the subject RLK protein did not comprise any LRR domains in its non-cytoplasmic domain, but instead this domain was Proline rich. Another disclosure (WO 00/04761) reported that upon overexpression of the RKN receptor kinase, root growth was enhanced. Similarly, it was suggested, but not shown, in WO 98/59039 that overexpression of the BRH receptor kinase would result in modulated yield.

However the RLK used in the latter two cases comprised 22 LRR domains in the non-cytoplasmic domain, typical for the LRR-X subfamily of receptor like kinases. So far there have been no reports to show or even suggest that receptor like kinases of the LRR-I subfamily may be useful for improving plant growth characteristics, and in particular in increasing yield.

It has now surprisingly been found that increasing expression and/or activity, relative to corresponding wild type plants, of an RLK827 protein in plants gives plants having improved growth characteristics, and in particular increased yield.

RLK827 is a receptor like kinase that is structurally related to LRRPK1 which is a member of the LRR-I subfamily of receptor like kinases (Shiu and Bleecker, 2001). The mature RLK827 protein has, starting from the N-terminus, a long putative non-cytoplasmic domain, a single transmembrane domain and a kinase domain in the C-terminal cytoplasmic part. The receptor like kinases are classified according to the composition of their non-cytoplasmic domain, which may comprise proline rich sequences, lectin domains, LRR domains, EGF repeats, TNFR repeats, thaumatin or agglutinin domains etc. A large group of receptor like kinases have Leucine Rich Repeats (LRR) in the non-cytoplasmic domain. The various LRR subfamilies differ from each other 0 in the number and position of these leucine rich repeats (for an overview, see Shiu and Bleecker, 2001). The putative non-cytoplasmic domain of RLK827 is characterised by the presence of one up to three tandem leucine rich repeat domains in its C-terminal part; RLK827 therefore belongs in the subfamily of LRR-I receptor kinases. The various LRR subfamilies of receptor kinases also differ from one other in their chromosomal distribution. Often they are arranged in tandem repeats. Tandem duplications, large-scale duplications and rearrangements of chromosomes are, at least in part, responsible for the evolution and expansion of the LRR receptor like kinases in plants. Accordingly, with a few exceptions, LRR-I receptor kinases are distributed on chromosome I, II and III in *Arabidopsis.*

According to one embodiment of the present invention there is provided a method for improving growth characteristics of a plant comprising increasing expression and/or activity of an RLK827 polypeptide or a homologue thereof and optionally selecting for plants having improved growth characteristics.

Advantageously, performance of the methods according to the present invention result in plants having a variety of improved growth characteristics, such as improved growth, improved yield, improved biomass, modified architecture or improved cell division, each relative to corresponding wild type plants. Preferably, the improved growth characteristics comprise at least increased yield relative to corresponding wild type plants. Preferably, the increased yield is increased seed yield, which includes increased number of (filled) seeds, increased total weight of seeds and increased harvest index.

The term "increased yield" as defined herein is taken to mean an increase in any one or more of the following, each relative to corresponding wild type plants: (i) increased biomass (weight) of one or more parts of a plant, particularly aboveground (harvestable) parts, increased root biomass or increased biomass of any other harvestable part; (ii) increased total seed yield, which includes an increase in seed biomass (seed weight) and which may be an increase in the seed weight per plant (total seed weight) or on an individual seed basis; (iii) increased number of (filled) seeds; (iv) increased seed size; (v) increased seed volume; (vi) increased individual seed area; (vii) increased individual seed length; (viii) increased harvest index, which is expressed as a ratio of the yield of harvestable parts, such as seeds, over the total biomass; (ix) increased number of florets per panicle which is extrapolated from the total number of seeds counted and the number of primary panicles; and (x) increased thousand kernel weight (TKW), which is extrapolated from the number of filled seeds counted and their total weight. An increased TKW may result from an increased seed size (length, width or both) and/or seed weight. An increased TKW may result from an increase in embryo size and/or endosperm size.

Taking corn as an example, a yield increase may be manifested as one or more of the following: increase in the number of plants per hectare or acre, an increase in the number of ears per plant, an increase in the number of rows, number of kernels per row, kernel weight, TKW, ear length/diameter, among others. Taking rice as an example, a yield increase may be manifested by an increase in one or more of the following: number of plants per hectare or acre, number of panicles per plant, number of spikelets per panicle, number of flowers per panicle, increase in the seed filling rate, increase in TKW, among others. An increase in yield may also result in modified architecture, or may occur as a result of modified architecture.

Preferably, performance of the methods of the present invention results in plants having increased yield and/or increased biomass. More particularly, performance of the methods according to the present invention results in plants having increased seed yield. Preferably, the increased seed yield comprises an increase in one or more of number of filled seeds, total seed weight, and harvest index, each relative to control plants. Therefore, according to the present invention, there is provided a method for increasing plant yield, which method comprises increasing expression and/or activity in a plant of an RLK827 polypeptide or a homologue thereof.

Since the modified plants according to the present invention have increased yield, it is likely that these plants exhibit an increased growth rate (during at least part of their life cycle), relative to the growth rate of corresponding wild type plants at a corresponding stage in their life cycle. The increased growth rate may be specific to one or more parts or cell types of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, flowering time and speed of seed maturation. An increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible. If the growth rate is sufficiently increased, it may allow for the sowing of further seeds of the same plant species (for example sowing and harvesting of rice plants followed by sowing and harvesting of further rice plants all within one conventional growing period). Similarly, if the growth rate is sufficiently increased, it may allow for the sowing of further seeds of different plants species (for example the sowing and harvesting of rice plants followed by, for example, the sowing and optional harvesting of soy bean, potatoes or any other suitable plant). Harvesting additional times from the same rootstock in the case of some plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves plotting growth experiments, such parameters may be: T-Mid (the time taken for plants to reach 50% of their maximal size) and T-90 (time taken for plants to reach 90% of their maximal size), amongst others.

Performance of the methods of the invention gives plants having an increased growth rate. Therefore, according to the present invention, there is provided a method for increasing the growth rate of plants, which method comprises increasing expression and/or activity in a plant of an RLK827 polypeptide or a homologue thereof.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the typical stresses to which a plant may be exposed. These stresses may be the everyday biotic and/or abiotic (environmental) stresses to which a plant is exposed. Typical abiotic or environmental stresses include temperature stresses caused by atypical hot or cold/freezing temperatures; salt stress; water stress (drought or excess water). Abiotic stresses may also be caused by chemicals. Biotic stresses are typically those stresses caused by pathogens, such as bacteria, viruses, fungi and insects.

The abovementioned growth characteristics may advantageously be modified in any plant.

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest or the specific modification in the gene/nucleic acid of interest. The term "plant" also encompasses plant cells, suspension cultures, callus tissue, embryos, meristematic regions, gametophytes, sporophytes, pollen, and microspores, again wherein each of the aforementioned comprise the gene/nucleic acid of interest.

Plants that are particularly useful in the methods of the invention include algae, ferns, and all plants which belong to the superfamily Viridiplantae, in particular monocotyledonous and dicotyledonous plants, including fodder or forage legumes, ornamental plants, food crops, trees, or shrubs selected from the list comprising *Abelmoschus* spp., *Acer* spp., *Actinidia* spp., *Agropyron* spp., *Allium* spp., *Amaranthus* spp., *Ananas comosus, Annona* spp., *Apium graveolens, Arabidopsis thaliana, Arachis* spp, *Artocarpus* spp., *Asparagus officinalis, Avena sativa, Averrhoa carambola, Benincasa hispida, Bertholletia excelsea, Beta vulgaris, Brassica* spp., *Cadaba farinosa, Camellia sinensis, Canna indica, Capsicum* spp., *Carica papaya, Carissa macrocarpa, Carthamus tinctorius, Carya* spp., *Castanea* spp., *Cichorium endivia, Cinnamomum* spp., *Citrullus lanatus, Citrus* spp., *Cocos* spp., *Coffea* spp., *Cola* spp., *Colocasia esculenta, Corylus* spp., *Crataegus* spp., *Cucumis* spp., *Cucurbita* spp., *Cynara* spp., *Daucus carota, Desmodium* spp., *Dimocarpus Iongan, Dioscorea* spp., *Diospyros* spp., *Echinochloa* spp., *Eleusine coracana, Eriobotrya japonica, Eugenia uniflora, Fagopyrom* spp., *Fagus* spp., *Ficus carica, Fortunella* spp., *Fragaria* spp., *Ginkgo biloba, Glycine* spp., *Gossypium hirsutum, Helianthus* spp., *Hibiscus* spp., *Hordeum* spp., *Ipomoea batatas, Juglans* spp., *Lactuca sativa, Lathyrus* spp., *Lemna* spp., *Lens culinaris, Linum usitatissimum, Litchi chinensis, Lotus* spp., *Luffa acutangula, Lupinus* spp., *Macrotyloma* spp., *Malpighia emarginata, Malus* spp., *Mammea americana, Mangifers indica, Manihot* spp., *Manilkara zapota, Medicago sativa, Melilotus* spp., *Mentha* spp., *Momordica* spp., *Morus nigra, Musa* spp., *Nicotiana* spp., *Olea* spp., *Opuntia* spp., *Ornithopus* spp., *Oryza* spp., *Panicum miliaceum, Passiflora edulis, Pastinaca sativa, Persea* spp., *Petroselinwn crispum, Phaseolus* spp., *Phoenix* spp., *Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Rubus* spp., *Saccharum* spp., *Sambucus* spp., *Secale cereale, Sesamum* spp., *Solanum* spp., *Sorghum bicolor, Spinacia* spp., *Syzygium* spp., *Tamarindus indica, Theobroma cacao, Trifolium* spp., *Triticosecale rimpaui, Triticum* spp., *Vaccinium* spp., *Vicia* spp., *Vigna* spp., *Vitis* spp., *Zea mays, Zizania palustris, Ziziphus* spp., amongst others.

According to a preferred feature of the present invention, the plant is a crop plant comprising soybean, sunflower, canola, alfalfa, rapeseed or cotton. Further preferably, the plant according to the present invention is a monocotyledonous plant such as sugarcane, most preferably a cereal, such as rice, maize, wheat, millet, barley, oats or sorghum.

The activity of an RLK827 protein may be increased by increasing levels of the RLK827 polypeptide. Alternatively, activity may also be increased when there is no change in levels of an RLK827, or even when there is a reduction in levels of an RLK827. This may occur when the intrinsic properties of the polypeptide are altered, for example, by making a mutant or selecting a variant that is more active that the wild type.

The term "RLK827 or homologue thereof" as defined herein refers to a Receptor Like Kinase (RLK) having kinase activity and comprising in its mature form a non-cytoplasmic domain (extracellular domain), a single transmembrane domain and a putative cytoplasmic kinase domain. The non-cytoplasmic domain or RLK827 comprises at least 1 but no more than 3 Leucine Rich Repeat (LRR) domains, preferably two LRR domains are present, more preferably three LRR domains. Further preferably, the length of the non-cytoplasmic domain ranges between 250 and 550 amino acids. The non-cytoplasmic domain preferably comprises the amino acid sequence motif LRxFP(E/D)GxRNC(Y/F) (SEQ ID NO: 33), wherein x may be any amino acid and where up to 2 other amino acids may be replaced by a conserved substitution as listed in Table 2. Preferably, the first x in this motif is Y or A, and the second x preferably is one of V, F, E and A.

The term "RLK827 or homologue thereof also refers to amino acid sequences having in increasing order of preference at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% overall sequence identity to the amino acid represented by SEQ ID NO: 2.

The term "RLK827 or homologue thereof comprises RLK827 (SEQ ID NO 2), its paralogues and orthologues. The overall sequence identity is determined using a global alignment algorithm, such as the Needleman Wunsch algorithm in the program GAP (GCG Wisconsin Package, Accelrys), using default parameter settings.

The various structural domains in an RLK827 protein may be identified using specialised databases e.g. SMART (Schultz et al. (1998) Proc. Natl. Acad. Sci. USA 95, 5857-5864; Letunic et al. (2002) Nucleic Acids Res 30, 242-244; smart.embl-heidelberg.de webpage) or Pfam (Bateman et al., Nucleic Acids Research 30(1):276-280 (2002), sanger.ac.uk/Software/Pfam/webpage).

The kinase domain is of a STYKc type (SMART accession number SM00221, Interpro accession number IPRO04040) and has possibly dual-specificity Ser/Thr/Tyr kinase activity. In the N-terminal extremity of the catalytic domain there is a glycine-rich stretch of residues in the vicinity of a lysine residue, which has been shown to be involved in ATP binding. In the central part of the catalytic domain there is a conserved aspartic acid residue, which is important for the catalytic activity of the enzyme.

Furthermore, LRR domains are well known in the art and are defined in Pfam (accession PF00560) as 20 to 29-residue sequence motifs present in tandem arrays in a number of proteins with diverse functions, such as hormone receptor interactions, enzyme inhibition, cell adhesion and cellular trafficking. Recent studies revealed the involvement of LRR proteins in early mammalian development, neural development, cell polarization, regulation of gene expression and apoptosis signalling. The primary function of these motifs appears to be to provide a versatile structural framework for the formation of protein-protein interactions. Sequence analyses of LRR proteins suggested the existence of several different subfamilies of LRRs. Apparently the repeats from different subfamilies never occur simultaneously and most probably evolved independently. However, all major classes of LRR seem to have curved horseshoe structures with a parallel beta sheet on the concave side and mostly helical elements on the convex side. At least six families of LRR proteins, characterised by different lengths and consensus sequences of the repeats, have been identified. Eleven-residue segments of the LRRs (LxxLxLxxN/CxL), corresponding to the β-strand and adjacent loop regions, are usually conserved in LRR proteins, whereas the remaining parts of the repeats may be very different. Despite the differences, each of these variable parts contains two half-turns at both ends and a "linear" segment (as the chain follows a linear path overall), usually formed by a helix, in the middle. The concave face and the adjacent loops are the most common protein interaction surfaces on LRR proteins. 3D structures of some LRR protein-ligand complexes show that the concave surface of LRR domain is ideal for interaction with alpha-helices, thus supporting earlier conclusions that the elongated and curved LRR structure provides an outstanding framework for achieving diverse protein-protein interactions. Molecular modelling suggests that the pattern LxxLxL, which is often conserved and which is shorter than the previously proposed LxxLxLxxN/CxL, is sufficient to impart the characteristic horseshoe curvature to proteins with 20- to 30-residue repeats. LRR domains of an LRK827 protein may differ from the canonical LRR domains known in the art but may be identified by suitable computer algorithms, preferably those used in the Pfam database.

Transmembrane domains are about 15 to 30 amino acids long and are usually composed of hydrophobic residues that form an alpha helix. They are usually predicted on the basis of hydrophobicity (for example Klein et al., Biochim. Biophys. Acta 815, 468, 1985; or Sonnhammer et al., In J. Glasgow, T. Littlejohn, F. Major, R. Lathrop, D. Sankoff, and C. Sensen, editors, Proceedings of the Sixth International Conference on Intelligent Systems for Molecular Biology, pages 175-182, Menlo Park, Calif., 1998. AAAI Press.).

Methods for the search and identification of RLK827 homologues would be well within the realm of persons skilled in the art. Such methods comprise comparison of the sequences represented by SEQ ID NO 1 or 2, in a computer readable format, with sequences that are available in public databases such as MIPS (mips.gsf.de/webpage), GenBank (ncbi.nlm.nih.gov/Genbank/index.html webpage) or EMBL Nucleotide Sequence Database (ebi.ac.uk/embl/index.html webpage), using algorithms well known in the art for the alignment or comparison of sequences, such as GAP (Needleman and Wunsch, J. Mol. Biol. 48; 443-453 (1970)), BESTFIT (using the local homology algorithm of Smith and Waterman (Advances in Applied Mathematics 2; 482-489 (1981))), BLAST (Altschul, S. F., Gish, W., Miller, W., Myers, E. W. & Lipman, D. J., J. Mol. Biol. 215:403-410 (1990)), FASTA and TFASTA (W. R. Pearson and D. J. Lipman Proc.Natl. Acad.Sci. USA 85:2444-2448 (1988)). The software for performing BLAST analysis is publicly available through the National Centre for Biotechnology Information (NCBI). The homologues mentioned below were identified using BLAST default parameters (BLOSUM62 matrix, gap opening penalty 11 and gap extension penalty 1) and preferably the full-length sequences are used for analysis.

Examples of proteins falling under the definition of "RLK827 polypeptide or a homologue thereof" include the *Arabidopsis* proteins At1g51850, At1g51805, At1g51810, At2g04300, At3g21340, At1g49100. It should be noted that a cluster of related putative receptor like kinases are located in tandem on chromosome 1 of *Arabidopsis thaliana*, including At1g51800, At1g51805, At1g51810, At1g51820, At1g51830, At1g51840, At1g51850, At1g51860, At1g51870, At1g51880 and At1g51890, of which at least four of them are highly related to RLK827.

It is to be understood that the term RLK827 polypeptide or a homologue thereof is not to be limited to the sequences represented by SEQ ID NO: 2, SEQ ID NO: 7, SEQ ID NO: 11, SEQ ID NO: 13, SEQ ID NO: 15 or SEQ ID NO: 17 and SEQ ID NO: 19, but that any polypeptide meeting the criteria of (i) having a cytoplasmic kinase domain and (ii) having at least one but no more than three LRR domains and preferably the consensus sequence of SEQ ID NO: 33 in the putative non-cytoplasmic part of the protein, separated from the kinase domain by a transmembrane region, and which kinase domain comprises the STYKc consensus sequence and/or (iii) being a paralogue or orthologue of RLK827 and having at least 25% sequence identity to the sequence of SEQ ID NO: 2, may be suitable for use in the methods of the invention. Preferably, the kinase domain is functional, meaning that the RLK827 polypeptide or its homologue has kinase activity.

To determine the kinase activity of RLK827, several assays are available and well known in the art (for example Current Protocols in Molecular Biology, Volumes 1 and 2, Ausubel et al. (1994), Current Protocols; or online such as at the protocol-online org webpage). In brief, the kinase assay generally involves (1) bringing the kinase protein into contact with a substrate polypeptide containing the target site to be phosphorylated; (2) allowing phosphorylation of the target site in an appropriate kinase buffer under appropriate conditions; (3) separating phosphorylated products from non-phosphorylated substrate after a suitable reaction period. The presence or absence of kinase activity is determined by the presence or absence of a phosphorylated target. In addition, quantitative measurements can be performed. Purified RLK827 protein, or cell extracts containing or enriched in the RLK827 protein could be used as source for the kinase protein. Alternatively, the approach of Zhao et al. (Plant Mol. Biol. 26, 791-603, 1994) could be used, where the cytoplasmic domain of a rice receptor like kinase was expressed in *Escherichia coli* and assayed for kinase activity. As a substrate, small peptides are particularly well suited. The peptide must comprise one or more serine, threonine or tyrosine residues in a phosphorylation site motif. A compilation of phosphorylation sites can be found in Biochimica et Biophysica Acta 1314, 191-225, (1996). In addition, the peptide substrates may advantageously have a net positive charge to facilitate binding to phosphocellulose filters, (allowing to separate the phosphorylated from non-phosphorylated peptides and to detect the phosphorylated peptides). If a phosphorylation site motif is not known, a general tyrosine kinase substrate can be used. For example, "Src-related peptide" (RRLIEDAEYAARG) is a substrate for many receptor and non-receptor tyrosine kinases). To determine the kinetic parameters for phosphorylation of the synthetic peptide, a range of peptide concentrations is required. For initial reactions, a peptide concentration of 0.7-1.5 mM could be used. For each kinase enzyme, it is important to determine the optimal buffer, ionic strength, and pH for activity. A standard 5× Kinase Buffer generally contains 5 mg/ml BSA (Bovine Serum Albumin preventing kinase adsorption to the assay tube), 150 mM Tris-Cl (pH 7.5), 100 mM $MgCl_2$. Divalent cations are required for most tyrosine kinases, although some tyrosine kinases (for example, insulin-, IGF-1-, and PDGF receptor kinases) require $MnCl_2$ instead of $MgCl_2$ (or in addition to $MgCl_2$). The optimal concentrations of divalent cations must be determined empirically for each protein kinase. A commonly used donor for the phosphoryl group is radio-labelled [gamma-$^{32}$P]ATP (normally at 0.2 mM final concentration). The amount of $^{32}$P incorporated in the peptides may be determined by measuring activity on the nitrocellulose dry pads in a scintillation counter.

Alternatively, the activity of an RLK827 polypeptide or of a homologue thereof may be assayed by expressing the RLK827 polypeptide or of a homologue thereof under control of a rice GOS2 promoter in rice plants, and in particular in the rice variety Nipponbare, which results in plants with increased yield compared to corresponding wild type plants. This increase in yield may for example be measured as one or more of an increase in number of filled seeds, in total weight of seeds and/or in harvest index.

The nucleic acid encoding an RLK827 polypeptide or a homologue thereof may be any natural or synthetic nucleic acid. An RLK827 polypeptide or a homologue thereof as defined herein is encoded by an RLK827 nucleic acid molecule. Therefore the term "RLK827 nucleic acid molecule" or "RLK827 gene" as defined herein is any nucleic acid molecule encoding an RLK827 polypeptide or a homologue thereof as defined above. Examples of RLK827 nucleic acid molecules include those represented by any one of SEQ ID NO: 1, SEQ ID NO: 6, SEQ ID NO: 10, SEQ ID NO: 12, SEQ ID NO: 14, SEQ ID NO: 16 and SEQ ID NO: 18, SEQ ID NO 23, SEQ ID NO 25, SEQ ID NO 27, SEQ ID NO 29, SEQ ID NO 31. RLK827 nucleic acids and functional variants thereof may be suitable in practising the methods of the invention. Functional variant RLK827 nucleic acids include portions of an RLK827 nucleic acid molecule and/or nucleic acids capable of hybridising with an RLK827 nucleic acid molecule or with a nucleic acid molecule encoding a homologue of RLK827. The term "functional" in the context of a functional variant refers to a variant RLK827 nucleic acid molecule (i.e. a portion or a hybridising sequence), which encodes a polypeptide having kinase activity and comprising a non-cytoplasmic (extracellular) domain, which non-cytoplasmic domain comprises at least 1 but no more than 3 LRR motifs and preferably also the amino acid sequence motif of SEQ ID NO: 33 as defined above, and a C-terminal kinase domain, that is separated from the non-cytoplasmic domain by a transmembrane domain.

The LRR-I type of receptor like kinases in plants have a modular structure, and it has been shown that one LRR protein is able to bind different ligands, for example the tomato SR160 receptor and its tomato homologue tBRH are able to bind brassinolide hormones and systemin, a long distance signalling peptide. Brassinolide and systemin do not compete for binding, suggesting they bind to different sites. Therefore, it is envisaged that engineering of LRR domains (e.g. by altering the number of LRR domains, or by performing domain stacking (binding to same or different ligand(s)), or domain shuffling), in such a way that the activity of the LRR is retained or modified, is useful in generating variant RLK827 nucleic acid molecules for performing the methods of the invention. In a similar way, the kinase domain may be engineered to improve kinase activity. A preferred type of variant includes those generated by domain deletion, stacking or shuffling (see for example He et al., Science 288, 2360-2363, 2000, or U.S. Pat. Nos. 5,811,238 and 6,395,547).

The term portion as defined herein refers to a piece of DNA comprising at least 150 nucleotides. A portion may be prepared, for example, by making one or more deletions to an RLK827 nucleic acid. The portions may be used in isolated form or they may be fused to other coding (or non coding) sequences in order to, for example, produce a protein that combines several activities, one of them being protein kinase activity. When fused to other coding sequences, the resulting polypeptide produced upon translation could be bigger than that predicted for the RLK827 portion. The portion useful in the methods of the present invention comprises at least the kinase domain, preferably also a non-cytoplasmic LRR domain and a transmembrane domain located N-terminally of the kinase domain, more preferably the portion comprises in the non-cytoplasmic domain at least 1 but no more than 3 LRR domains, most preferably, the portion comprises in the non-cytoplasmic domain at least 1 but no more than 3 LRR domains and the amino acid sequence motif of SEQ ID NO: 33 as defined above. Preferably, the functional portion is a portion of a nucleic acid as represented by any one of SEQ ID NO: 1, SEQ ID NO: 6, SEQ ID NO: 10, SEQ ID NO: 12, SEQ ID NO: 14, SEQ ID NO: 16 and SEQ ID NO: 18.

The term "hybridisation" as defined herein is a process wherein substantially homologous complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration, ionic strength and hybridisation buffer composition.

"Stringent hybridisation conditions" and "stringent hybridisation wash conditions" in the context of nucleic acid hybridisation experiments such as Southern and Northern hybridisations are sequence dependent and may differ depending on environmental parameters. The skilled artisan is aware of various parameters which may be altered during hybridisation and washing and which will either maintain or change the stringency conditions.

The $T_m$ is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M. Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the $T_m$, decreases about 1° C. per % base mismatch. The $T_m$ may be calculated using the following equations, depending on the types of hybrids:

DNA-DNA hybrids (Meinkoth and Wahl, Anal. Biochem., 138: 267-284, 1984):

$$T_m=81.5°\ C.+16.6\times\log\ [Na^+]^a+0.41\times\%[G/C^b]-500\times[L^c]^{-1}-0.61\times\%\ \text{formamide}$$

DNA-RNA or RNA-RNA hybrids:

$$T_m=79.8+18.5(\log_{10}[Na^+]^a)+0.58\ (\%\ G/C^b)+11.8\ (\%\ G/C^b)^2-820/L^c$$

oligo-DNA or oligo-RNA[d] hybrids:

For <20 nucleotides: $T_m=2\ (l_n)$

For 20-35 nucleotides: $T_m=22+1.46\ (l_n)$

[a] or for other monovalent cation, but only accurate in the 0.01-0.4 M range.

[b] only accurate for % GC in the 30% to 75% range.

[c] L=length of duplex in base pairs.

[d] Oligo, oligonucleotide; $l^n$, effective length of primer=2×(no. of G/C)+(no. of A/T).

Note: for each 1% formamide, the $T_m$ is reduced by about 0.6 to 0.7° C., while the presence of 6M urea reduces the $T_m$ by about 30° C.

Specificity of hybridisation is typically the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. Generally, suitable stringent conditions for nucleic acid hybridisation assays or gene amplification detection procedures are as set forth above. More or less stringent conditions may also be selected. Generally, low stringency conditions are selected to be about 50° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. For example, stringent conditions are those that are at least as stringent as, for example, conditions A-L; and reduced stringency conditions are at least as stringent as, for example, conditions M-R. Non-specific binding may be controlled using any one of a number of known techniques such as, for example, blocking the membrane with protein containing solutions, additions of heterologous RNA, DNA, and SDS to the hybridisation buffer, and treatment with Rnase.

Examples of hybridisation and wash conditions are listed in Table 1:

TABLE 1

| Stringency Condition | Polynucleotide Hybrid± | Hybrid Length (bp)‡ | Hybridization Temperature and Buffer† | Wash Temperature and Buffer† |
|---|---|---|---|---|
| A | DNA:DNA | > or equal to 50 | 65° C. 1×SSC; or 42° C., 1×SSC and 50% formamide | 65° C.; 0.3×SSC |
| B | DNA:DNA | <50 | Tb*; 1×SSC | Tb*; 1×SSC |
| C | DNA:RNA | > or equal to 50 | 67° C. 1×SSC; or 45° C., 1×SSC and 50% formamide | 67° C.; 0.3×SSC |
| D | DNA:RNA | <50 | Td*; 1×SSC | Td*; 1×SSC |
| E | RNA:RNA | > or equal to 50 | 70° C. 1×SSC; or 50° C., 1×SSC and 50% formamide | 70° C.; 0.3×SSC |
| F | RNA:RNA | <50 | Tf*; 1×SSC | Tf*; 1×SSC |
| G | DNA:DNA | > or equal to 50 | 65° C. 4×SSC; or 45° C.,.4×SSC and 50% formamide | 65° C.; 1×SSC |
| H | DNA:DNA | <150 | Th*; 4×SSC | Th*; 4×SSC |
| I | DNA:RNA | > or equal to 50 | 67° C. 4×SSC; or 45° C., 4×SSC and 50% formamide | 67° C.; 1×SSC |
| J | DNA:RNA | <50 | Tj*; 4×SSC | Tj*; 4×SSC |
| K | RNA:RNA | > or equal to 50 | 70° C. 4×SSC; or 40° C., 6×SSC and 50% formamide | 67° C.; 1×SSC |
| L | RNA:RNA | <50 | TI*; 2×SSC | TI*; 2×SSC |
| M | DNA:DNA | > or equal to 50 | 50° C. 4×SSC; or 40° C., 6×SSC and 50% formamide | 50° C.; 2×SSC |
| N | DNA:DNA | <50 | Tn*; 6×SSC | Tn*; 6×SSC |
| 0 | DNA:RNA | > or equal to 50 | 55° C. 4×SSC; or 42° C., 6×SSC and 50% formamide | 55° C.; 2×SSC |
| P | DNA:RNA | <50 | Tp*; 6×SSC | Tp*; 6×SSC |

TABLE 1-continued

| Stringency Condition | Polynucleotide Hybrid± | Hybrid Length (bp)‡ | Hybridization Temperature and Buffer† | Wash Temperature and Buffer† |
|---|---|---|---|---|
| Q | RNA:RNA | > or equal to 50 | 60° C. 4×SSC; or 45° C., 6×SSC and 50% formamide | 60° C.; 2×SSC |
| R | RNA:RNA | <50 | Tr*; 4×SSC | Tr*; 4×SSC |

‡The "hybrid length" is the anticipated length for the hybridising nucleic acid. When nucleic acids of known sequence are hybridised, the hybrid length may be determined by aligning the sequences and identifying the conserved regions described herein.

†SSPE (1×SSPE is 0.15M NaCl, 1O mM $NaH_2PO_4$, and 1.25 mM EDTA, pH7.4) may be substituted for SSC (1×SSC is 0.15M NaCI and 15 mM sodium citrate) in the hybridisation and wash buffers; washes are performed for 15 minutes after hybridisation is complete. The hybridisations and washes may additionally include 5 × Denhardt's reagent, 0.5-1.0% SDS, 100 μg/ml denatured, fragmented salmon sperm DNA, 0.5% sodium pyrophosphate, and up to 50% formamide.

*Tb-Tr: The hybridisation temperature for hybrids anticipated to be less than 50 base pairs in length should be 5-10° C. less than the melting temperature $T_m$ of the hybrids; the $T_m$ is determined according to the above-mentioned equations.

±The present invention also encompasses the substitution of any one, or more DNA or RNA hybrid partners with either a PNA, or a modified nucleic acid.

For the purposes of defining the level of stringency, reference can conveniently be made to Sambrook et al. (2001) Molecular Cloning: a laboratory manual, 3rd Edition Cold Spring Harbor Laboratory Press, CSH, New York or to Current Protocols in Molecular Biology, John Wiley & Sons, N.Y. (1989).

For example, a nucleic acid encoding SEQ ID NO: 2 or a homologue thereof may be used in a hybridisation experiment. Alternatively fragments thereof may be used as probes. Depending on the starting pool of sequences from which the RLK is to be identified, different fragments for hybridization can be selected. For example, when a limited number of homologues with a high sequence identity to RLK827 are desired, a less conserved fragment may be used for hybridisation such as GGTAGACTCGCCAAAGAATTTGAACCACTCGTTGAT (nucleotides 184 to 219 of SEQ ID NO: 1). By aligning SEQ ID NO: 2 and homologues thereof it is possible to design equivalent nucleic acid fragments useful as probes for hybridisation. Preferably the hybridising sequence comprises at least the kinase domain, preferably also a non-cytoplasmic LRR domain and a transmembrane domain located N-terminally of the kinase domain, more preferably the portion comprises in the non-cytoplasmic domain at least 1 but no more than 3 LRR domains, most preferably, the portion comprises in the non-cytoplasmic domain at least 1 but no more than 3 LRR domains and the amino acid sequence motif of SEQ ID NO: 33 as defined above.

After hybridisation and washing, the duplexes may be detected by autoradiography (when radiolabeled probes were used) or by chemiluminescence, immunodetection, by fluorescent or chromogenic detection, depending on the type of probe labelling. Alternatively, a ribonuclease protection assay may be performed for detection of RNA:RNA hybrids The RLK827 nucleic acid molecule or variant thereof may be derived from any natural or artificial source. The nucleic acid/gene or variant thereof may be isolated from a microbial source, such as bacteria, yeast or fungi, or from a plant, alga or animal (including human) source. This nucleic acid may be modified from its native form in composition and/or genomic environment through deliberate human manipulation. The nucleic acid is preferably of plant origin, whether from the same plant species (for example to the one in which it is to be introduced) or whether from a different plant species. The nucleic acid may be isolated from a dicotyledonous species, preferably from the family Brassicaceae, further preferably from *Arabidopsis thaliana*. More preferably, the RLK827 isolated from *Arabidopsis thaliana* is represented by SEQ ID NO: 1 and the RLK827 amino acid sequence is as represented by SEQ ID NO: 2.

Functional variants useful in the methods of the present invention also include alternative splice variants of an RLK827 nucleic acid molecule or gene. The term "alternative splice variant" as used herein encompasses variants of a nucleic acid sequence in which selected introns and/or exons have been excised, replaced or added. Such variants will be ones in which the biological activity of the protein is retained, which may be achieved by selectively retaining functional segments of the protein. Such splice variants may be found in nature or may be manmade. Methods for making such splice variants are well known in the art. Preferred splice variants are splice variants of a nucleic acid represented by SEQ ID NO: 1. Further preferred are splice variants encoding a polypeptide retaining kinase activity and having at least one but no more than three LRR domains in the putative non-cytoplasmic part of the protein, separated from the kinase domain by a transmembrane region. More preferred splice variants comprise in addition also the amino acid sequence motif of SEQ ID NO: 33 in the putative non-cytoplasmic domain. Most preferred splice variants of an RLK827 nucleic acid molecule are those that encode an RLK827 polypeptide as defined above.

Functional variants useful in the methods of the present invention furthermore include allelic variants of a nucleic acid encoding an RLK827 polypeptide or a homologue thereof, preferably an allelic variant of the nucleic acid represented by SEQ ID NO 1. Further preferably, the polypeptide encoded by the allelic variant has kinase activity and retains at least one but no more than three LRR domains in the putative non-cytoplasmic part of the protein, separated from the kinase domain by a transmembrane region. More preferred allelic variants comprise in addition also the amino acid sequence motif of SEQ ID NO: 33 in the putative non-cytoplasmic domain. Most preferred allelic variants of an RLK827 nucleic acid molecule are those that encode an RLK827 polypeptide as defined above. Allelic variants exist in nature and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

The expression and/or activity of an RLK827 polypeptide or a homologue thereof may also be increased by introducing a genetic modification (preferably in the locus of an RLK827 gene). The locus of a gene as defined herein is taken to mean a genomic region which includes the gene of interest and 10 kb up- or downstream of the coding region.

The genetic modification may be introduced, for example, by any one (or more) of the following methods: TDNA activation, TILLING, site-directed mutagenesis, homologous recombination, directed evolution or by introducing and expressing in a plant a nucleic acid encoding an RLK827 polypeptide or a homologue thereof. Following introduction of the genetic modification there follows a step of selecting for increased expression and/or activity of an RLK827 polypeptide, which increase in expression and/or activity gives plants having improved growth characteristics.

T-DNA activation tagging (Hayashi et al. Science 258, 1350-1353, 1992) involves insertion of T-DNA usually containing a promoter (may also be a translation enhancer or an intron), in the genomic region of the gene of interest or 10 KB up- or down stream of the coding region of a gene in a configuration such that such promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into a plant genome, for example, through *Agrobacterium* infection and leads to overexpression of genes near to the inserted T-DNA. The resulting transgenic plants show dominant phenotypes due to overexpression of genes close to the introduced promoter. The promoter to be introduced may be any promoter capable of directing expression of a gene in the desired organism, in this case a plant. For example, constitutive, tissue-preferred, cell type-preferred and inducible promoters are all suitable for use in T-DNA activation.

A genetic modification may also be introduced in the locus of an RLK827 gene using the technique of TILLING (Targeted Induced Local Lesions IN Genomes). This is a mutagenesis technology useful to generate and/or identify, and to eventually isolate mutagenised variants of an RLK827 nucleic acid molecule capable of exhibiting RLK827 activity. TILLING also allows selection of plants carrying such mutant variants. These mutant variants may even exhibit higher RLK827 activity than that exhibited by the gene in its natural form. TILLING combines high-density mutagenesis with high-throughput screening methods. The steps typically followed in TILLING are: (a) EMS mutagenesis (Redei and Koncz (1992), In: C Koncz, N-H Chua, J Schell, eds, Methods in *Arabidopsis* Research. World Scientific, Singapore, pp 16-82; Feldmann et al., (1994) In: E M Meyerowitz, C R Somerville, eds, *Arabidopsis*. Cold Spring Harbor Laboratory Press, Cold Spring Harbor, N.Y., pp 137-172; Lightner and Caspar (1998), In: J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum Nature Biotechnol. 18, 455-457, 2000, Stemple Nature Rev. Genet. 5, 145-150, 2004).

Site-directed mutagenesis may be used to generated variants of RLK827 nucleic acids or portions thereof that retain activity, namely, protein kinase activity. Several methods are available to achieve site-directed mutagenesis, the most common being PCR based methods (See for example Ausubel et al., Current Protocols in Molecular Biology. Wiley Eds., at the 4ulr.com/products/currentprotocols/index.html webpage).

Directed evolution may be used to generate variants of RLK827 nucleic acid molecules or portions thereof encoding RKS11 or RKS4 polypeptides or orthologues or portions thereof having an increased biological activity. Directed evolution consists of iterations of DNA shuffling followed by appropriate screening and/or selection (Castle et al., (2004) Science 304(5674): 1151-4; U.S. Pat. Nos. 5,811,238 and 6,395,547).

TDNA activation, TILLING, site-directed mutagenesis and directed evolution are examples of technologies that enable the generation novel alleles and variants of RLK827 that retain RLK827 function and which are therefore useful in the methods of the invention.

Homologous recombination allows introduction in a genome of a selected nucleic acid at a defined selected position. Homologous recombination is a standard technology used routinely in biological sciences for lower organism such as yeast or the moss *Physcomitrella*. Methods for performing homologous recombination in plants have been described not only for model plants (Offringa et al. (1990) EMBO J. 9, 3077-3084) but also for crop plants, for example rice (Terada et al., (2002) Nature Biotechnol. 20, 1030-1034; or lida and Terada (2004) Curr. Opin. Biotechnol. 15, 132-138). The nucleic acid to be targeted (which may be an RLK827 nucleic acid molecule or variant thereof as hereinbefore defined) need not be targeted to the locus of an RLK827 gene, but may be introduced in, for example, regions of high expression. The nucleic acid to be targeted may be an improved allele used to replace the endogenous gene or may be introduced in addition to the endogenous gene.

According to a preferred embodiment of the invention, plant growth characteristics may be improved by introducing and expressing in a plant a nucleic acid encoding an RLK827 polypeptide or a homologue thereof.

A preferred method for introducing a genetic modification (which in this case need not be in the locus of an RLK827 gene) is to introduce and express in a plant a nucleic acid encoding an RLK827 polypeptide or a homologue thereof. An RLK827 polypeptide or homologue thereof as mentioned above is one having kinase activity and comprising a non-cytoplasmic (extracellular) domain, which non-cytoplasmic domain comprises at least 1 but no more than 3 LRR motifs and preferably also the amino acid sequence motif of SEQ ID NO: 33 as defined above, and a C-terminal kinase domain that is separated from the non-cytoplasmic domain by a transmembrane domain. Preferably, the RLK827 polypeptide or homologue thereof has in increasing order of preference, at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% overall sequence identity to the amino acid sequence represented by SEQ ID NO: 2.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

Encompassed by the term "homologues" are orthologous sequences and paralogous sequences, two special forms of homology which encompass evolutionary concepts used to describe ancestral relationships of genes.

The term "paralogous" relates to gene-duplications within the genome of a species leading to paralogous genes. Paralogues of RLK827 may easily be identified by performing a BLAST analysis against a set of sequences from the same species as the query sequence.

The term "orthologous" relates to homologous genes in different organisms due to speciation. Orthologues in, for example, monocot plant species may easily be found by performing a so-called reciprocal blast search. This may be done by a first blast involving blasting the sequence in question (for example, SEQ ID NO: 1 or SEQ ID NO: 2) against any sequence database, such as the publicly available NCBI database which may be found at: the ncbi.nlm.nih.gov webpage. If orthologues in rice were sought, the sequence in question would be blasted against, for example, the 28,469 full-length cDNA clones from *Oryza sativa* Nipponbare available at NCBI. BLASTn or tBLASTX may be used when starting from nucleotides or BLASTP or TBLASTN when starting from the protein, with standard default values. The blast results may be filtered. The full-length sequences of either the filtered results or the non-filtered results are then blasted back (second blast) against the sequences of the organism from which the sequence in question is derived. The results of the first and second blasts are then compared. An orthologue is found when the results of the second blast give as hits with the highest similarity an RLK827 nucleic acid or RLK827 polypeptide, for example, if one of the organisms is *Arabidopsis thaliana* then a paralogue is found. In the case of large families, ClustalW may be used, followed by the construction of a neighbour joining tree, to help visualize the clustering. Using a reciprocal BLAST procedure a rice orthologue (Unigene accession number Os.26918) was identified represented by the ESTs CB631540, CB628137.1 and CB31541.1. Preferred orthologues are those having the highest similarity to RLK827 or to a paralogue thereof in a reciprocal BLAST search. Other examples of rice orthologues are given in SEQ ID NOs 24, 26, 28, 30 and 32.

A homologue may be in the form of a "substitutional variant" of a protein, i.e. where at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues. Preferably, amino acid substitutions comprise conservative amino acid substitutions (Table 2). To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company).

TABLE 2

Examples of conserved amino acid substitutions:

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Less conserved substitutions can be made in case the above-mentioned amino acid properties are not so critical.

A homologue may also be in the form of an "insertional variant" of a protein, i.e. where one or more amino acid residues are introduced into a predetermined site in a protein. Insertions may comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, $(histidine)_6$-tag, glutathione S-transferase-tag, protein A, maltose-binding protein, dihydrofolate reductase, Tag 100 epitope, c-myc epitope, FLAG®-epitope, lacZ, CMP (calmodulin-binding peptide), HA epitope, protein C epitope and VSV epitope.

Homologues in the form of "deletion variants" of a protein are characterised by the removal of one or more amino acids from a protein.

Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making mutations at predetermined sites in DNA are well known to those skilled in the art and include M 13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

The RLK827 polypeptide or homologue thereof may be a derivative. "Derivatives" include peptides, oligopeptides, polypeptides, proteins and enzymes which may comprise substitutions, deletions or additions of naturally and non-naturally occurring amino acid residues compared to the amino acid sequence of a naturally-occurring form of the protein, for example, as presented in SEQ ID NO 2. "Derivatives" of a protein encompass peptides, oligopeptides, polypeptides, proteins and enzymes which may comprise naturally occurring altered, glycosylated, acylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein.

According to a preferred aspect of the present invention, enhanced or increased expression of an RLK827 nucleic acid molecule or variant thereof is envisaged. Methods for obtaining enhanced or increased expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of an RLK827 nucleic acid or variant thereof. For example, endogenous promoters may be, altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region may be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, Mol. Cell. Biol. 8, 4395-4405 (1988); Callis et al., Genes Dev. 1, 1183-1200 (1987)). Such intron enhancement of gene expression is typically greatest when placed near the 5' end of the transcription unit. Use of the maize introns Adh1-S intron 1, 2, and 6, the Bronze-1 intron are known in the art. See generally, The Maize Handbook, Chapter 116, Freeling and Walbot, Eds., Springer, N.Y. (1994).

The invention also provides genetic constructs and vectors to facilitate introduction and/or expression of the nucleotide sequences useful in the methods according to the invention.

Therefore, there is provided a gene construct comprising:

(i) an RLK827 nucleic acid molecule or functional variant thereof;

(ii) one or more control sequence capable of driving expression of the nucleic acid sequence of (i); and optionally (iii) a transcription termination sequence.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells.

Plants are transformed with a vector comprising the sequence of interest (i.e., an RLK827 nucleic acid or functional variant thereof). The sequence of interest is operably linked to one or more control sequences (at least to a promoter). The terms "regulatory element", "control sequence" and "promoter" are all used interchangeably herein and are to be taken in a broad context to refer to regulatory nucleic acid sequences capable of effecting expression of the sequences to which they are ligated. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative which confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Advantageously, any type of promoter may be used to drive expression of the nucleic acid sequence. The promoter may be an inducible promoter, i.e. having induced or increased transcription initiation in response to a developmental, chemical, environmental or physical stimulus. An example of an inducible promoter being a stress-inducible promoter, i.e. a promoter activated when a plant is exposed to various stress conditions, is the water stress induced promoter WS118. Additionally or alternatively, the promoter may be a tissue-specific promoter, i.e. one that is capable of preferentially initiating transcription in certain tissues, such as the leaves, roots, seed tissue etc. An example of a seed-specific promoter is the rice oleosin 18 kDa promoter (Wu et al. (1998) J Biochem 123(3): 386-91).

Preferably, the RLK827 nucleic acid or functional variant thereof is operably linked to a constitutive promoter. A constitutive promoter is transcriptionally active during most, but not necessarily all, phases of its growth and development and is substantially ubiquitously expressed. Preferably, the constitutive promoter is a GOS2 promoter (from rice) (nucleotides 1 to 2193 in SEQ ID NO: 3). It should be clear that the applicability of the present invention is not restricted to the RLK827 nucleic acid represented by SEQ ID NO: 1, nor is the applicability of the invention restricted to expression of an RLK827 nucleic acid when driven by a GOS2 promoter. Examples of other constitutive promoters that may also be used to drive expression of a RLK827 nucleic acid are shown in Table 3 below.

TABLE 3

Examples of constitutive promoters

| Gene Source | Expression Motif | Reference |
|---|---|---|
| Actin | Constitutive | McElroy et al, Plant Cell, 2: 163-171, 1990 |
| CAMV 35S | Constitutive | Odell et al, Nature, 313: 810-812, 1985 |
| CaMV 19S | Constitutive | Nilsson et al., *Physiol. Plant. 100*: 456-462, 1997 |
| GOS2 | Constitutive | de Pater et al, Plant J Nov; 2(6): 837-44, 1992 |
| Ubiquitin | Constitutive | Christensen et al, Plant Mol. Biol. 18: 675-689, 1992 |
| Rice cyclophilin | Constitutive | Buchholz et al, Plant Mol Biol. 25(5): 837-43, 1994 |
| Maize H3 histone | Constitutive | Lepetit et al, Mol. Gen. Genet. 231: 276-285, 1992 |
| Actin 2 | Constitutive | An et al, Plant J. 10(1); 107-121, 1996 |

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences which may be suitable for use in performing the invention. Such sequences would be known or may readily be obtained by a person skilled in the art.

An example of an expression cassette comprising the RLK827 nucleic acid operably linked to the GOS2 promoter and further comprising a terminator sequence is given in SEQ ID NO: 3.

The genetic constructs of the invention may further include an origin of replication sequence, which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the fl-ori and colE1.

The genetic construct may optionally comprise a selectable marker gene. As used herein, the term "selectable marker gene" includes any gene which confers a phenotype on a cell in which it is expressed to facilitate the identification and/or selection of cells which are transfected or transformed with a nucleic acid construct of the invention. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin), to herbicides (for example bar which provides resistance to Basta; aroA or gox providing resistance against glyphosate), or genes that provide a metabolic trait (such as manA that allows plants to use mannose as sole carbon source). Visual marker genes result in the formation of colour (for example β-glucuranidase, GUS), luminescence (such as luciferase) or fluorescence (Green Fluorescent Protein, GFP, and derivatives thereof).

The present invention also encompasses plants obtainable by the methods according to the present invention. The present invention therefore provides plants obtainable by the methods according to the present invention, which plants have introduced therein an RLK827 nucleic acid or a functional variant thereof, or which plants have introduced therein a genetic modification, preferably in the locus of an RLK827 gene.

The invention also provides a method for the production of transgenic plants having improved growth characteristics, comprising introduction and expression in a plant of an RLK827 nucleic acid or a functional variant thereof.

More specifically, the present invention provides a method for the production of transgenic plants having improved growth characteristics, which method comprises:

(i) introducing into a plant or plant cell an RLK827 nucleic acid or a functional variant thereof; and (ii) cultivating the plant cell under conditions promoting plant growth and development.

The nucleic acid may: be introduced directly into a plant cell or into the plant itself (including introduction into a tissue, organ or any other part of a plant). According to a preferred feature of the present invention, the nucleic acid is preferably introduced into a plant by transformation.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

Transformation of plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens et al. (1982) Nature 296, 72-74; Negrutiu et al. (1987) Plant Mol. Biol. 8, 363-373); electroporation of protoplasts (Shillito et al. (1985) Bio/Technol 3, 1099-1102); microinjection into plant material (Crossway et al. (1986) Mol. Gen. Genet. 202, 179-185); DNA or RNA-coated particle bombardment (Klein et al. (1987) Nature 327, 70) infection with (non-integrative) viruses and the like. Transgenic rice plants expressing an RLK827 gene are preferably produced via *Agrobacterium*-mediated transformation using any of the well known methods for rice transformation, such as described in any of the following: published European patent application EP 1198985 A1, Aldemita and Hodges (Planta 199, 612-617, 1996); Chan et al. (Plant Mol. Biol. 22, 491-506, 1993), Hiei et al. (Plant J. 6, 271-282, 1994), which disclosures are incorporated by reference herein as if fully set forth. In the case of corn transformation, the preferred method is as described in either lshida et al. (Nature Biotechnol. 14, 745-50, 1996) or Frame et al. (Plant Physiol. 129, 13-22, 2002), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art. The cultivation of transformed plant cells into mature plants may thus encompass steps of selection and/or regeneration and/or growing to maturity.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette);

grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention. The invention also includes host cells containing an isolated RLK827 nucleic acid or a functional variant thereof. Preferred host cells according to the invention are plant cells. The invention also extends to harvestable parts of a plant according to the invention such as but not limited to seeds, leaves, fruits, flowers, stems, rhizomes, tubers and bulbs. The invention furthermore relates to products directly derived from a harvestable part of such a plant, such as dry pellets or powders, oil, fat and fatty acids, starch or proteins.

The present invention also encompasses the use of RLK827 nucleic acids or functional variants thereof and to the use of RLK827 polypeptides or homologues thereof.

One such use relates to improving the growth characteristics of plants. A preferred use relates to improving yield of plants, a more preferred use relates to increasing seed yield. The seed yield may include one or more of the following: increased number of (filled) seeds, increased seed weight, increased harvest index, among others.

RLK827 nucleic acids or functional variants thereof or RLK827 polypeptides or homologues thereof may find use in breeding programmes in which a DNA marker is identified which may be genetically linked to an RLK827 gene or variant thereof. The RLK827 or variants thereof or RLK827 or homologues thereof may be used to define a molecular marker. This DNA or protein marker may then be used in breeding programs to select plants having altered growth characteristics. The RLK827 gene or variant thereof may, for example, be a nucleic acid as represented by any one of SEQ ID NO: 1, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 23, SEQ ID NO: 25, SEQ ID NO: 27, SEQ ID NO: 29 and SEQ ID NO: 31.

Allelic variants of an RLK827 may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called “natural” origin caused unintentionally. Identification of allelic variants then takes place by, for example, PCR. This is followed by a selection step for selection of superior allelic variants of the sequence in question and which give rise improved growth characteristics in a plant. Selection is typically carried out by monitoring growth performance of plants containing different allelic variants of the sequence in question, for example, different allelic variants of any one of SEQ ID NO: 1, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 23, SEQ ID NO: 25, SEQ ID NO: 27, SEQ ID NO: 29 and SEQ ID NO: 31. Growth performance may be monitored in a greenhouse or in the field. Further optional steps include crossing plants, in which the superior allelic variant was identified, with another plant. This could be used, for example, to make a combination of interesting phenotypic features.

An RLK827 nucleic acid or variant thereof may also be used as a probe for genetically and physically mapping the genes that they are a part of, and as markers for traits linked to those genes. Such information may be useful in plant breeding in order to develop lines with desired phenotypes. Such use of RLK827 nucleic acids or variants thereof requires only a nucleic acid sequence of at least 15 nucleotides in length. The RLK827 nucleic acids or variants thereof may be used as restriction fragment length polymorphism (RFLP) markers. Southern blots of restriction-digested plant genomic DNA may be probed with the RLK827 nucleic acids or variants thereof. The resulting banding patterns may then be subjected to genetic analyses using computer programs such as MapMaker (Lander et al. (1987) Genomics 1, 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the RLK827 nucleic acid or variant thereof in the genetic map previously obtained using this population (Botstein et al. (1980) Am. J. Hum. Genet. 32, 314-331).

The production and use of plant gene-derived probes for use in genetic mapping is described in Bematzky and Tanksley (Plant Mol. Biol. Reporter 4, 37-41, 1986). Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., for the placing of sequences on physical maps; see Hoheisel et al. In: Nonmammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet. 7, 149-154). Although current methods of FISH mapping favour use of large clones (several to several hundred KB; see Laan et al. (1995) Genome Res. 5, 13-20), improvements in sensitivity may allow performance of FISH mapping using shorter probes.

A variety of nucleic acid amplification-based methods of genetic and physical mapping may be earned out using the nucleic acids. Examples include allele-specific amplification (Kazazian (1989) J. Lab. Clin. Med. 11, 95-96), polymorphism of PCR-amplified fragments (CAPS; Sheffield et al. (1993) Genomics 16, 325-332), allele-specific ligation (Landegren et al. (1988) Science 241, 1077-1080), nucleotide extension reactions (Sokolov (1990) Nucleic Acid Res. 18, 3671), Radiation Hybrid Mapping (Walter et al. (1997) Nat. Genet. 7, 22-28) and Happy Mapping (Dear and Cook (1989) Nucleic Acid Res. 17, 6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

In this way, generation, identification and/or isolation of modified plants with altered RLK827 expression and/or activity displaying improved growth characteristics can be performed.

RLK827 nucleic acids or functional variants thereof or RLK827 polypeptides or homologues thereof may also find use as growth regulators. Since these molecules have been shown to be useful in improving the growth characteristics of plants, they would also be useful growth regulators, such as herbicides or growth stimulators. The present invention therefore provides a composition comprising an RLK827 or a functional variant thereof or an RLK827 polypeptide or homologue thereof, together with a suitable carrier, diluent or excipient, for use as a growth regulator.

The methods according to the present invention result in plants having improved growth characteristics, as described hereinbefore. These advantageous growth characteristics may also be combined with other economically advantageous traits, such as further yield-enhancing traits, tolerance to various stresses, traits modifying various architectural features and/or biochemical and/or physiological features.

DESCRIPTION OF FIGURES

The present invention will now be described with reference to the following figures in which:

FIG. 4 A-V details examples of sequences useful in performing the methods according to the present invention. The "At" number refers to the MIPs Accession number (mips.gsf.de web page); other identifiers refer to GenBank accession numbers.

EXAMPLES

The present invention will now be described with reference to the following examples, which are by way of illustration alone.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols (at the 4ulr.com/products/currentprotocols/index.html webpage). Standard materials and methods for plant molecular work are described in Plant Molecular Biology Labfax (1993) by R. D. D. Cray, published by BIOS Scientific Publications Ltd (UK) and Blackwell Scientific Publications (UK).

Example 1

Gene Cloning

The *Arabidopsis* AtRLK827 (internal code CDS0827) was amplified by PCR using as template an *Arabidopsis thaliana* seedling cDNA library (Invitrogen, Paisley, UK). After reverse transcription of RNA extracted from seedlings, the cDNAs were cloned into pCMV Sport 6.0. Average insert size of the bank was 1.5 kb, and the original number of clones was $1.59\times10^7$ cfu. Original titer was determined to be $9.6\times10^5$ cfu/ml, and after a first amplification of $6\times10^{11}$ cfu/ml. After plasmid extraction, 200 ng of template was used in a 50 µl PCR mix. Primers prm00405 (SEQ ID NO: 4, sense) and prm00406 (SEQ ID NO: 5, reverse complementary), which include the AttB sites for Gateway recombination, were used for PCR amplification. PCR was performed using Hifi Taq DNA polymerase in standard conditions. A PCR fragment of 2750 bp was amplified and purified also using standard methods. The first step of the Gateway procedure, the BP reaction, was then performed, during which the PCR fragment recombines in vivo with the pDONR201 plasmid to produce, according to the Gateway® terminology, an "entry clone", p3080. Plasmid pDONR201 was purchased from Invitrogen, as part of the Gateway® technology.

Example 2

Vector Construction and Rice Transformation

The entry clone p3080 was subsequently used in an LR reaction with a destination vector used for *Oryza sativa* transformation. This vector contained as functional elements within the T-DNA borders: a plant selectable marker; a visual marker expression cassette; and a Gateway cassette intended for LR in vivo recombination with the sequence of interest already cloned in the entry clone. A rice GOS2 promoter for constitutive expression was located upstream of this Gateway cassette.

Figure 1:
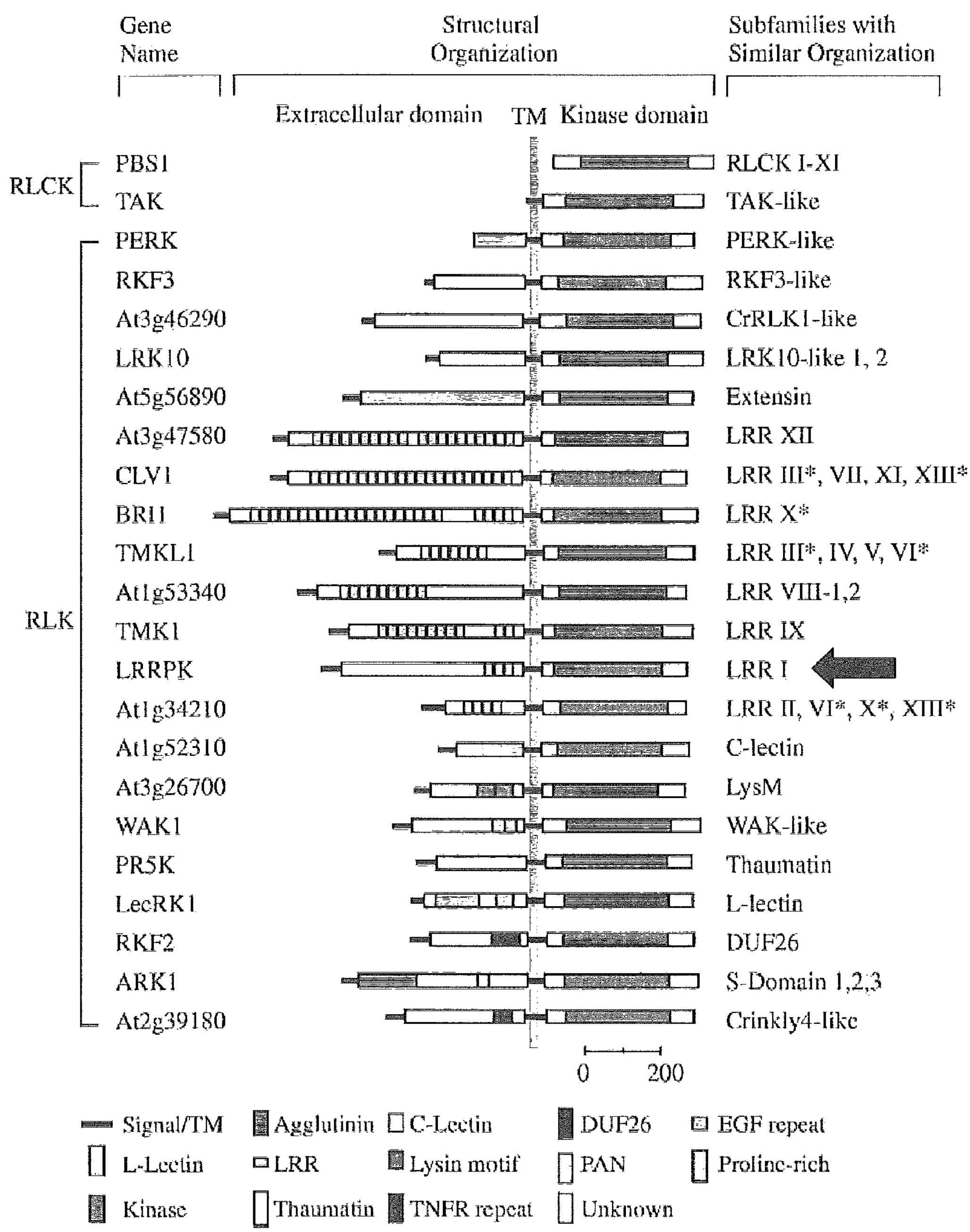
FIG. 1 gives a graphical overview of plant receptor like kinase structures (adapted from Shiu & Bleecker, 2001). The arrow indicates the structure of RLK827 and the subfamily to which RLK827 belongs.
Figure 2:
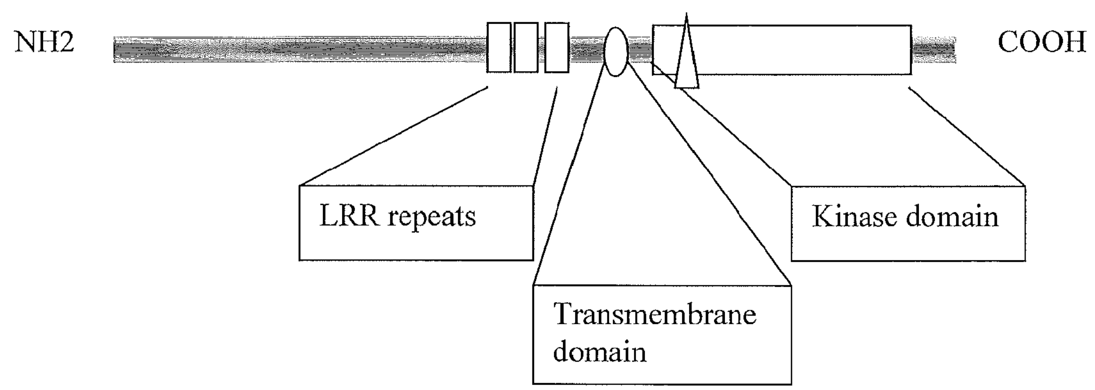
FIG. 2 shows a schematic representation of the structure of SEQ ID NO: 2. The triangle indicates sequence with an ATP-binding site signature.
Figure 3:
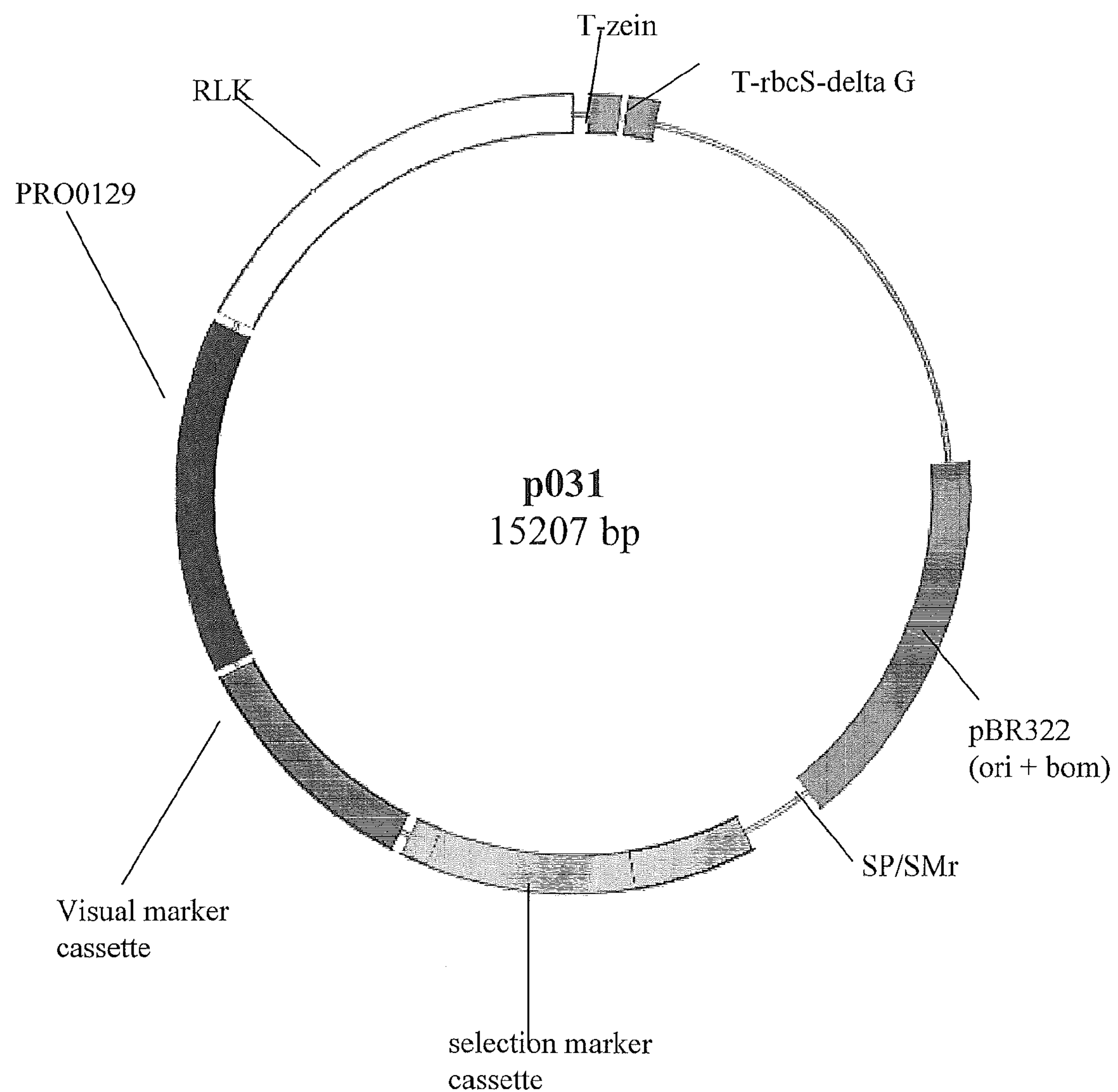
FIG. 3 shows the binary vector p031 for transformation and expression in *Oryza sativa* of an *Arabidopsis thalianan* RLK827 (internal reference CDS0827) under the control of a rice GOS2 promoter (internal reference PR00129).

After the LR recombination step, the resulting expression vector p031 (FIG. 3) was transformed into the Agrobacterium strain LBA4404 and subsequently to *Oryza sativa* plants. Transformed rice plants were allowed to grow and were then examined for the parameters described in Example 3.

Example 3

Evaluation of Trans Formants: Growth Measurements

Approximately 15 to 20 independent TO transformants were generated. The primary transformants were transferred from tissue culture chambers to a greenhouse for growing and harvest of T1 seed. Five events of which the T1 progeny segregated 3:1 for presence/absence of the transgene were retained. For each of these events, 10 T1 seedlings containing the transgene (hetero- and homo-zygotes), and 10 T1 seedlings lacking the transgene (nullizygotes), were selected by visual marker screening. The selected T1 plants were transferred to a greenhouse. Each plant received a unique barcode label to link unambiguously the phenotyping data to the corresponding plant. The selected T1 plants were grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes were grown side-by-side at random positions. From the stage of sowing until the stage of maturity the plants were passed several times through a digital imaging cabinet. At each time point digital images (2048×1536 pixels, 16 million colours) were taken of each plant from at least 6 different angles.

The mature primary panicles were harvested, bagged, barcode-labelled and then dried for three days in the oven at 37° C. The panicles were then threshed and all the seeds collected. The filled husks were separated from the empty ones using an air-blowing device. After separation, both seed lots were then counted using a commercially available counting machine. The empty husks were discarded. The filled husks were weighed on an analytical balance and the cross-sectional area of the seeds was measured using digital imaging. This procedure resulted in the set of seed-related parameters described below.

These parameters were derived in an automated way from the digital images using image analysis software and were analysed statistically. A two factor ANOVA (analyses of variance) corrected for the unbalanced design was used as statistical model for the overall evaluation of plant phenotypic characteristics. An F-test was carried out on all the parameters measured of all the plants of all the events transformed with that gene. The F-test was carried out to check for an effect of the gene over all the transformation events and to verify for an overall effect of the gene, also named herein "global gene effect". If the value of the F test shows that the data are significant, than it is concluded that there is a "gene" effect, meaning that not only presence or the position of the gene is causing the effect. The threshold for significance for a true global gene effect is set at 5% probability level for the F test.

To check for an effect of the genes within an event, i.e., for a line-specific effect, a t-test was performed within each event using data sets from the transgenic plants and the corresponding null plants. "Null plants" or "null segregants" or "nullizygotes" are the plants treated in the same way as the transgenic plant, but from which the transgene has segregated. Null plants can also be described as the homozygous negative transformed plants. The threshold for significance for the t-test is set at 10% probability level. The results for some events can be above or below this threshold. This is based on the hypothesis that a gene might only have an effect in certain positions in the genome, and that the occurrence of this position-dependent effect is not uncommon. This kind of gene effect is also named herein a "line effect of the gene". The p-value is obtained by comparing the t-value to the t-distribution or alternatively, by comparing the F-value to the F-distribution. The p-value then gives the probability that the null hypothesis (i.e., that there is no effect of the transgene) is correct.

The data obtained in the first experiment were confirmed in a second experiment with T2 plants. Three lines that had the correct expression pattern were selected for further analysis. Seed batches from the positive plants (both hetero- and homozygotes) in T1, were screened by monitoring marker expression. For each chosen event, the heterozygote seed batches were then retained for T2 evaluation. Within each seed batch an equal number of positive and negative plants were grown in the greenhouse for evaluation.

A total number of 120 RLK827 transformed plants were evaluated in the T2 generation, that is 40 plants per event of which 20 positives for the transgene, and 20 negatives.

Because two experiments with overlapping events have been carried out, a combined analysis was performed. This is useful to check consistency of the effects over the two experiments, and if this is the case, to accumulate evidence from both experiments in order to increase confidence in the conclusion. The method used was a mixed-model approach that takes into account the multilevel structure of the data (i.e. experiment—event—segregants). P-values are obtained by comparing likelihood ratio test to chi square distributions.

Example 4

Evaluation of Transformants: Measurement of Seed-Related Parameters

Upon analysis of the seeds as described above, the inventors found that plants transformed with the RLK827 gene construct had a higher number of filled seeds, a higher total weight of seeds and an increased harvest index compared to plants lacking the RLK827 transgene. Positive results obtained for plants in the T1 generation were again obtained in the T2 generation. As an example, data for line OS2 are given (Table 4).

TABLE 4

| | T1 generation | | T2 generation | | Combined analysis |
|---|---|---|---|---|---|
| Line OS2 | % difference | p-value | % difference | p-value | p-value |
| Nr filled seeds | 41 | 0.0047 | 54 | 0.0726 | 0.0079 |
| Total weight seeds | 43 | 0.0051 | 60 | 0.0655 | 0.0065 |
| Harvest Index | 48 | 0.0007 | 57 | 0.0527 | 0.0003 |

Number of Filled Seeds:

The number of filled seeds was determined by counting the number of filled husks that remained after the separation step. Line OS2 showed a significant increase in filled seed number of 41% for the T1 generation. This increase was also observed in the T2 generation (+54%). The combined analysis of T1 and T2 data confirmed that the effect on the number of filled seeds was highly significant (p-value of 0.0079).

Total Seed Yield:

The total seed yield (total weight of seeds) per plant was measured by weighing all filled husks harvested from a plant. Not only the number of filled seeds was increased, but also the total seed weight. In the first generation there was an increase of 43%, which increase was statistically significant. This increase was confirmed in the T2 generation and the combined analysis showed that the increases in seed yield were significant (p-value of 0.0065).

Harvest Index:

Line OS2 furthermore had an increased harvest index. The harvest index in the present invention is defined as the ratio between the total seed yield and the above ground area (mm2), multiplied by a factor 106. Both in T1 and T2 a positive effect on harvest index was observed (increase of respectively 48 and 57% with p-values of 0.0007 and 0.0527). Here too, the combined analysis of the T1 and T2 data showed a significant effect (p-value 0.0003).

The invention claimed is:

1. A method for improving growth characteristics of a plant relative to a corresponding wild type plant, comprising increasing activity of an RLK827 polypeptide and/or by increasing expression of a nucleic acid encoding an RLK827 polypeptide or a homologue thereof having RLK827 biological and functional activity, and optionally selecting for plants having improved growth characteristics; wherein the RLK827 polypeptide or the homologue thereof comprises a non-cytoplasmic domain having at least 1 but no more than 3 Leucine Rich Repeat (LRR) domains, a transmembrane domain, and a kinase domain.

2. The method of claim 1, wherein said increased activity and/or increased expression is effected by introducing a genetic modification in the locus of a gene encoding an RLK827 polypeptide or a homologue thereof.

3. The method of claim 2, wherein said genetic modification is effected by one of site-directed mutagenesis, homologous recombination, TILLING, directed evolution and T-DNA activation.

4. The method of claim 1, wherein said improved plant growth characteristic is increased yield.

5. A plant or plant cell obtained by the method of claim 1.

6. The method of claim 1, wherein the RLK polypeptide is a homologue that has at least 44% identity to the amino acid of SEQ ID NO 2.

7. The method of claim 1, wherein the RLK polypeptide is a homologue that has at least 60% identity to the amino acid of SEQ ID NO 2.

8. The method of claim 1, wherein the RLK polypeptide is selected from the group consisting of SEQ ID NO 2, SEQ ID NO 7, SEQ ID NO 11, SEQ ID NO 13, SEQ ID NO 15, SEQ ID NO 17, SEQ ID NO 19, SEQ ID NO 24, SEQ ID NO 26, SEQ ID NO 28, SEQ ID NO 30, and SEQ ID NO 32.

9. A construct comprising:

(i) an RLK827 nucleic acid molecule encoding a Receptor Like Kinase (RLK)827 or a homologue thereof having RLK827 biological and functional activity, wherein the RLK827 polypeptide or the homologue comprises a non-cytoplasmic domain having at least 1 but no more than 3 Leucine Rich Repeat (LRR) domains, a transmembrane domain, and a kinase domain;

(ii) one or more control sequences capable of driving expression of the nucleic acid sequence of (i), wherein a control sequence is a constitutive GOS2 promoter; and optionally (iii) a transcription termination sequence;

wherein the construct when expressed in a plant confers increased yield relative to a corresponding wild type plant.

10. A plant or plant cell comprising the construct of claim 9.

11. The plant or plant cell of claim 10, wherein said plant is a monocotyledonous plant and wherein said plant cell is derived from a monocotyledonous plant.

12. A harvestable part, and/or a product directly derived therefrom, of the plant of claim 10, wherein said harvestable part and/or product comprise the construct.

13. The harvestable part of claim 12, wherein said harvestable part is a seed.

14. The construct of claim 9, wherein said RLK827 nucleic acid molecule comprises a sequence capable of hybridising under stringent conditions to the complementary strand of the RLK827 nucleic acid comprising the sequence of SEQ ID NO: 1, SEQ ID NO: 6, SEQ ID NO: 10, SEQ ID NO: 12, SEQ ID NO: 14, SEQ ID NO: 16, SEQ ID NO: 18, SEQ ID NO: 23, SEQ ID NO: 25, SEQ ID NO: 27, SEQ ID NO: 29, or SEQ ID NO: 31, wherein the stringent conditions comprise 1×SSC and 50% formamide at 65° C. or 42° C., followed by washes at 65° C. in 0.3×SSC.

15. The construct of claim 9, wherein the RLK827 nucleic acid molecule encodes an RLK827 polypeptide which comprises a polypeptide encoded by the sequence of SEQ ID NO: 1, SEQ ID NO: 6, SEQ ID NO: 10, SEQ ID NO: 12, SEQ ID NO: 14, SEQ ID NO: 16, SEQ ID NO: 18SEQ ID NO: 23, SEQ ID NO: 25, SEQ ID NO: 27, SEQ ID NO: 29, or SEQ ID NO: 31.

16. The construct of claim 9, wherein said RLK comprises a sequence having at least 60% identity to the amino acid sequence of SEQ ID NO: 2.

17. The construct of claim 9, wherein said RLK comprises a sequence having at least 95% identity to the amino acid sequence of SEQ ID NO: 2.

18. The construct of claim 9, wherein said RLK827 nucleic acid molecule encodes a protein comprising a non-cytoplasmic domain with 1 but no more than 3 LRR domains and the amino acid sequence motif of SEQ ID NO: 33, a transmembrane domain, and a kinase domain.

19. A method for increasing yield relative to a corresponding wild type plant, comprising introducing and expressing in a plant an RLK827 nucleic acid molecule encoding a Receptor Like Kinase (RLK) comprising a non-cytoplasmic domain having at least 1 but no more than 3 Leucine Rich Repeat (LRR) domains, a transmembrane domain, and a kinase domain, wherein the nucleic acid molecule encodes an RLK827 polypeptide which comprises a polypeptide encoded by the sequence of SEQ ID NO: 1, SEQ ID NO: 6, SEQ ID NO: 10, SEQ ID NO: 12, SEQ ID NO: 14, SEQ ID NO: 16, SEQ ID NO: 18, SEQ ID NO: 23, SEQ ID NO: 25, SEQ ID NO: 27, SEQ ID NO: 29, or SEQ ID NO: 31.

* * * * *

SEQUENCE LISTING

```
<160> NUMBER OF SEQ ID NOS: 33

<210> SEQ ID NO 1
<211> LENGTH: 2655
```

```
<212> TYPE: DNA
<213> ORGANISM: Arabidospis thaliana

<400> SEQUENCE: 1

atggagagac attttgtgtt tattgccacc tatttgctga tatttcatct tgttcaagct     60

caaaatcaaa caggattcat tagtgtggat tgtggtttat cccttcttga gtctccttac    120

gatgcaccac aaacgagttt aacatataca tcagatgccg atttagtagc tagtggcaaa    180

accggtagac tcgccaaaga atttgaacca ctcgttgata agccgacttt gacactgaga    240

tactttccag agggagtacg aaactgctac aatctaaatg tcaccagcga caccaactat    300

ttaatcaagg ccacatttgt atatgggaat tacgatggtc ttaatgttgg gccaaacttc    360

aacctttatc tcggtccgaa tttgtggaca acggtgagta gcaatgacac tatagaggaa    420

ataatccttg tgaccagatc caactcttta caggtgtgtc ttgttaagac gggaataagt    480

ataccttta taaatatgtt ggagctacga ccgatgaaga aaaatatgta cgttactcaa    540

agcggttcac tgaagtattt attcagaggg tatattagca attcaagtac tcgtataagg    600

ttcccggatg atgtctatga ccgtaaatgg tacccgctct tcgacgactc atggacacaa    660

gtaactacaa atctcaaagt gaacacaagt attacttatg aactaccaca aagtgtaatg    720

gcaaaagccg caacgccaat taaggctaac gacaccttga acattacatg gacggtagag    780

ccccctacta cacagtttta ctcttacgta cacattgcag agattcaggc tctaagggca    840

aacgagacaa gggagttcaa tgtgacactg aatggagaat atacttttgg accttttagt    900

cctataccgc taaaaaccgc atccatagtc gacttaagcc cagggcaatg cgatggaggg    960

agatgcattt tgcaggttgt gaagacgctg aaatctacgc ttcctccttt acttaatgct   1020

atcgaagctt tcaccgtgat tgatttcccg caaatggaga caaatgaaaa tgatgttgct   1080

gggatcaaga atgttcaagg tacttatgga ttgagtagaa ttagttggca aggagatcca   1140

tgtgtcccca aacagttatt gtgggatggt ctaaactgca aaaactcgga tatttctacg   1200

ccaccgataa tcacttcctt agacttatct tcaagtggat taactgggat catcacgcaa   1260

gccattaaga atcttactca cctgcaaata ttggacttgt cagataataa tttgactgga   1320

gaagtacctg agtttttagc tgacataaaa tcactcttgg tcataaactt aagtggtaat   1380

aatctaagtg gctcagttcc tccctcactt cttcagaaga aaggaatgaa gttaaatgtc   1440

gaaggcaatc ctcatattct ttgcacaacg ggttcttgtg tcaagaaaaa agaggatgga   1500

cataagaaaa agagtgtcat agtgccagtt gttgcatcaa ttgcttcaat agctgttctt   1560

ataggtgcat tggttctgtt tctaattctt agaaagaaaa ggtcaccaaa agttgaaggg   1620

ccaccaccat cttatatgca agcatcagat ggtagattgc ctagatcatc tgaaccggca   1680

atcgtaacga aaaatagaag gtttcttat tcacaagttg tgataatgac aaataacttc    1740

caaagaatcc ttgggaaagg agggtttgga atggtttatc atggtttcgt gaacggtaca   1800

gagcaagtag ctgttaagat actctcccat tcatcgtctc aaggatataa acaattcaaa   1860

gctgaggtag aacttcttct tagagttcat cacaagaact tggttggtct tgttgggtac   1920

tgcgacgaag gagataactt ggctcttatc tatgaataca tggccaatgg agatctaaaa   1980

gaacatatgt caggaacacg taaccgcttt attttgaatt ggggaactag actaaaaata   2040

gtcatcgagt ctgcacaagg actcgagtac ttgcataatg gttgcaaacc accaatggta   2100

catagggacg tcaaaactac aaatatattg ttgaacgaac actttgaggc caaacttgcg   2160

gattttgggc tttcgagatc attcctgatc gaaggtgaaa ctcatgtatc aacagttgtt   2220

gctggaactc ctggatatct cgatcctgaa taccatagaa caaattggtt gacagaaaag   2280
```

```
agtgatgttt atagttttgg gattctattg ttggagatta tcacaaaccg acatgtgatc   2340

gaccaaagcc gtgaaaagcc acacatagga gaatgggtag gagtaatgct tacaaaagga   2400

gacatccaaa gcattatgga tccaagtctc aatgaagatt atgattccgg ttctgtttgg   2460

aaagctgttg aactagcaat gagttgtcta aatcattctt cagcgagaag accgaccatg   2520

tcccaagttg ttattgaatt gaacgagtgt ctggcttctg aaaatgcaag ggaggaggca   2580

agtcgggaca tggaatcaaa gagttctata gaagtgagct tgacgtttgg tactgaagtg   2640

agcccaaacg ctcga                                                    2655


<210> SEQ ID NO 2
<211> LENGTH: 885
<212> TYPE: PRT
<213> ORGANISM: Arabidospis thaliana

<400> SEQUENCE: 2

Met Glu Arg His Phe Val Phe Ile Ala Thr Tyr Leu Leu Ile Phe His
1               5                   10                  15

Leu Val Gln Ala Gln Asn Gln Thr Gly Phe Ile Ser Val Asp Cys Gly
            20                  25                  30

Leu Ser Leu Leu Glu Ser Pro Tyr Asp Ala Pro Gln Thr Ser Leu Thr
        35                  40                  45

Tyr Thr Ser Asp Ala Asp Leu Val Ala Ser Gly Lys Thr Gly Arg Leu
    50                  55                  60

Ala Lys Glu Phe Glu Pro Leu Val Asp Lys Pro Thr Leu Thr Leu Arg
65                  70                  75                  80

Tyr Phe Pro Glu Gly Val Arg Asn Cys Tyr Asn Leu Asn Val Thr Ser
                85                  90                  95

Asp Thr Asn Tyr Leu Ile Lys Ala Thr Phe Val Tyr Gly Asn Tyr Asp
            100                 105                 110

Gly Leu Asn Val Gly Pro Asn Phe Asn Leu Tyr Leu Gly Pro Asn Leu
        115                 120                 125

Trp Thr Thr Val Ser Ser Asn Asp Thr Ile Glu Glu Ile Ile Leu Val
    130                 135                 140

Thr Arg Ser Asn Ser Leu Gln Val Cys Leu Val Lys Thr Gly Ile Ser
145                 150                 155                 160

Ile Pro Phe Ile Asn Met Leu Glu Leu Arg Pro Met Lys Lys Asn Met
                165                 170                 175

Tyr Val Thr Gln Ser Gly Ser Leu Lys Tyr Leu Phe Arg Gly Tyr Ile
            180                 185                 190

Ser Asn Ser Ser Thr Arg Ile Arg Phe Pro Asp Asp Val Tyr Asp Arg
        195                 200                 205

Lys Trp Tyr Pro Leu Phe Asp Asp Ser Trp Thr Gln Val Thr Thr Asn
    210                 215                 220

Leu Lys Val Asn Thr Ser Ile Thr Tyr Glu Leu Pro Gln Ser Val Met
225                 230                 235                 240

Ala Lys Ala Ala Thr Pro Ile Lys Ala Asn Asp Thr Leu Asn Ile Thr
                245                 250                 255

Trp Thr Val Glu Pro Pro Thr Thr Gln Phe Tyr Ser Tyr Val His Ile
            260                 265                 270

Ala Glu Ile Gln Ala Leu Arg Ala Asn Glu Thr Arg Glu Phe Asn Val
        275                 280                 285

Thr Leu Asn Gly Glu Tyr Thr Phe Gly Pro Phe Ser Pro Ile Pro Leu
    290                 295                 300
```

```
Lys Thr Ala Ser Ile Val Asp Leu Ser Pro Gly Gln Cys Asp Gly Gly
305                 310                 315                 320

Arg Cys Ile Leu Gln Val Val Lys Thr Leu Lys Ser Thr Leu Pro Pro
                325                 330                 335

Leu Leu Asn Ala Ile Glu Ala Phe Thr Val Ile Asp Phe Pro Gln Met
            340                 345                 350

Glu Thr Asn Glu Asn Asp Val Ala Gly Ile Lys Asn Val Gln Gly Thr
        355                 360                 365

Tyr Gly Leu Ser Arg Ile Ser Trp Gln Gly Asp Pro Cys Val Pro Lys
    370                 375                 380

Gln Leu Leu Trp Asp Gly Leu Asn Cys Lys Asn Ser Asp Ile Ser Thr
385                 390                 395                 400

Pro Pro Ile Ile Thr Ser Leu Asp Leu Ser Ser Ser Gly Leu Thr Gly
                405                 410                 415

Ile Ile Thr Gln Ala Ile Lys Asn Leu Thr His Leu Gln Ile Leu Asp
            420                 425                 430

Leu Ser Asp Asn Asn Leu Thr Gly Glu Val Pro Glu Phe Leu Ala Asp
        435                 440                 445

Ile Lys Ser Leu Leu Val Ile Asn Leu Ser Gly Asn Asn Leu Ser Gly
    450                 455                 460

Ser Val Pro Pro Ser Leu Leu Gln Lys Lys Gly Met Lys Leu Asn Val
465                 470                 475                 480

Glu Gly Asn Pro His Ile Leu Cys Thr Thr Gly Ser Cys Val Lys Lys
                485                 490                 495

Lys Glu Asp Gly His Lys Lys Lys Ser Val Ile Val Pro Val Val Ala
            500                 505                 510

Ser Ile Ala Ser Ile Ala Val Leu Ile Gly Ala Leu Val Leu Phe Leu
        515                 520                 525

Ile Leu Arg Lys Lys Arg Ser Pro Lys Val Glu Gly Pro Pro Pro Ser
    530                 535                 540

Tyr Met Gln Ala Ser Asp Gly Arg Leu Pro Arg Ser Ser Glu Pro Ala
545                 550                 555                 560

Ile Val Thr Lys Asn Arg Arg Phe Ser Tyr Ser Gln Val Val Ile Met
                565                 570                 575

Thr Asn Asn Phe Gln Arg Ile Leu Gly Lys Gly Gly Phe Gly Met Val
            580                 585                 590

Tyr His Gly Phe Val Asn Gly Thr Glu Gln Val Ala Val Lys Ile Leu
        595                 600                 605

Ser His Ser Ser Ser Gln Gly Tyr Lys Gln Phe Lys Ala Glu Val Glu
    610                 615                 620

Leu Leu Leu Arg Val His His Lys Asn Leu Val Gly Leu Val Gly Tyr
625                 630                 635                 640

Cys Asp Glu Gly Asp Asn Leu Ala Leu Ile Tyr Glu Tyr Met Ala Asn
                645                 650                 655

Gly Asp Leu Lys Glu His Met Ser Gly Thr Arg Asn Arg Phe Ile Leu
            660                 665                 670

Asn Trp Gly Thr Arg Leu Lys Ile Val Ile Glu Ser Ala Gln Gly Leu
        675                 680                 685

Glu Tyr Leu His Asn Gly Cys Lys Pro Pro Met Val His Arg Asp Val
    690                 695                 700

Lys Thr Thr Asn Ile Leu Leu Asn Glu His Phe Glu Ala Lys Leu Ala
705                 710                 715                 720

Asp Phe Gly Leu Ser Arg Ser Phe Leu Ile Glu Gly Glu Thr His Val
                725                 730                 735
```

```
Ser Thr Val Val Ala Gly Thr Pro Gly Tyr Leu Asp Pro Glu Tyr His
            740                 745                 750

Arg Thr Asn Trp Leu Thr Glu Lys Ser Asp Val Tyr Ser Phe Gly Ile
        755                 760                 765

Leu Leu Leu Glu Ile Ile Thr Asn Arg His Val Ile Asp Gln Ser Arg
    770                 775                 780

Glu Lys Pro His Ile Gly Glu Trp Val Gly Val Met Leu Thr Lys Gly
785                 790                 795                 800

Asp Ile Gln Ser Ile Met Asp Pro Ser Leu Asn Glu Asp Tyr Asp Ser
                805                 810                 815

Gly Ser Val Trp Lys Ala Val Glu Leu Ala Met Ser Cys Leu Asn His
            820                 825                 830

Ser Ser Ala Arg Arg Pro Thr Met Ser Gln Val Val Ile Glu Leu Asn
        835                 840                 845

Glu Cys Leu Ala Ser Glu Asn Ala Arg Gly Gly Ala Ser Arg Asp Met
    850                 855                 860

Glu Ser Lys Ser Ser Ile Glu Val Ser Leu Thr Phe Gly Thr Glu Val
865                 870                 875                 880

Ser Pro Asn Ala Arg
                885


<210> SEQ ID NO 3
<211> LENGTH: 4898
<212> TYPE: DNA
<213> ORGANISM: Artificial sequence
<220> FEATURE:
<223> OTHER INFORMATION: expression cassette

<400> SEQUENCE: 3

aatccgaaaa gtttctgcac cgttttcacc ccctaactaa caatataggg aacgtgtgct      60

aaatataaaa tgagacctta tatatgtagc gctgataact agaactatgc aagaaaaact     120

catccaccta ctttagtggc aatcgggcta aataaaaaag agtcgctaca ctagtttcgt     180

tttccttagt aattaagtgg gaaaatgaaa tcattattgc ttagaatata cgttcacatc     240

tctgtcatga agttaaatta ttcgaggtag ccataattgt catcaaactc ttcttgaata     300

aaaaaatctt tctagctgaa ctcaatgggt aaagagagag atttttttta aaaaaataga     360

atgaagatat tctgaacgta ttggcaaaga tttaaacata taattatata attttatagt     420

ttgtgcattc gtcatatcgc acatcattaa ggacatgtct tactccatcc caatttttat     480

ttagtaatta aagacaattg acttattttt attatttatc ttttttcgat tagatgcaag     540

gtacttacgc acacactttg tgctcatgtg catgtgtgag tgcacctcct caatacacgt     600

tcaactagca acacatctct aatatcactc gcctatttaa tacatttagg tagcaatatc     660

tgaattcaag cactccacca tcaccagacc acttttaata atatctaaaa tacaaaaaat     720

aattttacag aatagcatga aaagtatgaa acgaactatt taggtttttc acatacaaaa     780

aaaaaaagaa ttttgctcgt gcgcgagcgc caatctccca tattgggcac acaggcaaca     840

acagagtggc tgcccacaga acaacccaca aaaaacgatg atctaacgga ggacagcaag     900

tccgcaacaa ccttttaaca gcaggctttg cggccaggag agaggaggag aggcaaagaa     960

aaccaagcat cctcctcctc ccatctataa attcctcccc ccttttcccc tctctatata    1020

ggaggcatcc aagccaagaa gagggagagc accaaggaca cgcgactagc agaagccgag    1080

cgaccgcctt cttcgatcca tatcttccgg tcgagttctt ggtcgatctc ttccctcctc    1140

cacctcctcc tcacagggta tgtgcccttc ggttgttctt ggatttattg ttctaggttg    1200
```

-continued

```
tgtagtacgg gcgttgatgt taggaaaggg gatctgtatc tgtgatgatt cctgttcttg   1260
gatttgggat agaggggttc ttgatgttgc atgttatcgg ttcggtttga ttagtagtat   1320
ggttttcaat cgtctggaga gctctatgga aatgaaatgg tttagggtac ggaatcttgc   1380
gattttgtga gtacctttttg tttgaggtaa aatcagagca ccggtgattt tgcttggtgt   1440
aataaaagta cggttgtttg gtcctcgatt ctggtagtga tgcttctcga tttgacgaag   1500
ctatcctttg tttattccct attgaacaaa aataatccaa ctttgaagac ggtcccgttg   1560
atgagattga atgattgatt cttaagcctg tccaaaattt cgcagctggc ttgtttagat   1620
acagtagtcc ccatcacgaa attcatggaa acagttataa tcctcaggaa caggggattc   1680
cctgttcttc cgatttgctt tagtcccaga atttttttc ccaaatatct taaaaagtca   1740
ctttctggtt cagttcaatg aattgattgc tacaaataat gcttttatag cgttatccta   1800
gctgtagttc agttaatagg taatacccct atagtttagt caggagaaga acttatccga   1860
tttctgatct ccatttttaa ttatatgaaa tgaactgtag cataagcagt attcatttgg   1920
attattttt ttattagctc tcaccccttc attattctga gctgaaagtc tggcatgaac   1980
tgtcctcaat tttgttttca aattcacatc gattatctat gcattatcct cttgtatcta   2040
cctgtagaag tttctttttg gttattcctt gactgcttga ttacagaaag aaatttatga   2100
agctgtaatc gggatagtta tactgcttgt tcttatgatt catttccttt gtgcagttct   2160
tggtgtagct tgccactttc accagcaaag ttcatttaaa tcaactaggg atatcacaag   2220
tttgtacaaa aaagcaggct tcacaatgga gagacatttt gtgtttattg ccacctattt   2280
gctgatattt catcttgttc aagctcaaaa tcaaacagga ttcattagtg tggattgtgg   2340
tttatccctt cttgagtctc cttacgatgc accacaaacg ggtttaacat atacatcaga   2400
tgccgattta gtagctagtg gcaaaaccgg tagactcgcc aaagaatttg aaccactcgt   2460
tgataagccg actttgacac tgagatactt tccagaggga gtacgaaact gctacaatct   2520
aaatgtcacc agcgacacca actatttaat caaggccaca tttgtatatg ggaattacga   2580
tggtcttaat gttgggccaa acttcaacct ttatctcggt ccgaatttgt ggacaacggt   2640
gagtagcaat gacactatag aggaaataat ccttgtgacc agatccaact ctttacaggt   2700
gtgtcttgtt aagacgggaa taagtatacc ttttataaat atgttggagc tacgaccgat   2760
gaagaaaaat atgtacgtta ctcaaagcgg ttcactgaag tatttattca gagggtatat   2820
tagcaattca agtactcgta taaggttccc ggatgatgtc tatgaccgta aatggtaccc   2880
gctcttcgac gactcatgga cacaagtaac tacaaatctc aaagtgaaca caagtattac   2940
ttatgaacta ccacaaagtg taatggcaaa agccgcaacg ccaattaagg ctaacgacac   3000
cttgaacatt acatggacgg tagagccccc tactacacag ttttactctt acgtacacat   3060
tgcagagatt caggctctaa gggcaaacga gacaagggag ttcaatgtga cactgaatgg   3120
agaatatact tttggacctt ttagtcctat accgctaaaa accgcatcca tagtcgactt   3180
aagcccaggg caatgcgatg gagggagatg cattttgcag gttgtgaaga cgctgaaatc   3240
tacgcttcct cctttactta atgctatcga agctttcacc gtgattgatt tcccgcaaat   3300
ggagacaaat gaaaatgatg ttgctgggat caagaatgtt caaggtactt atggattgag   3360
tagaattagt tggcaaggag atccatgtgt ccccaaacag ttattgtggg atggtctaaa   3420
ctgcaaaaac tcggatattt ctacgccacc gataatcact tccttagact tatcttcaag   3480
tggattaact gggatcatca cgcaagccat taagaatctt actcacctgc aaatattgga   3540
cttgtcagat aataatttga ctggagaagt acctgagttt ttagctgaca taaaatcact   3600
```

cttggtcata aacttaagtg gtaataatct aagtggctca gttcctccct cacttcttca 3660
gaagaaagga atgaatgtcg aaggcaatcc tcatattctt tgcacaacgg gttcttgtgt 3720
caagaaaaaa gaggatggac ataagaaaaa gagtgtcata gtgccagttg ttgcatcaat 3780
tgcttcaata gctgttctta taggtgcatt ggttctgttt ctaattctta gaaagaaaag 3840
gtcaccaaaa gttgaagggc caccaccatc ttatatgcaa gcatcagatg gtagattgcc 3900
tagatcatct gaaccggcaa tcgtaacgaa aaatagaagg ttttcttatt cacaagttgt 3960
gataatgaca aataacttcc aaagaatcct tgggaaagga gggtttggaa tggtttatca 4020
tggtttcgtg aacggtacag agcaagtagc tgttaagata ctctcccatt catcgtctca 4080
aggatataaa caattcaaag ctgaggtaga acttcttctt agagttcatc acaagaactt 4140
ggttggtctt gttgggtact gcgacgaagg agataacttg gctcttatct atgaatacat 4200
ggccaatgga gatctaaaag aacatatgtc aggaacacgt aaccgcttta ttttgaattg 4260
gggaactaga ctaaaaatag tcatcgagtc tgcacaagga ctcgagtact tgcataatgg 4320
ttgcaaacca ccaatggtac atagggacgt caaaactaca aatatattgt tgaacgaaca 4380
ctttgaggcc aaacttgcgg attttgggct ttcgagatca ttcctgatcg aaggtgaaac 4440
tcatgtatca acagttgttg ctggaactcc tggatatctc gatcctgaat accatagaac 4500
aaattggttg acagaaaaga gtgatgttta tagttttggg attctattgt tggagattat 4560
cacaaaccga catgtgatcg accaaagccg tgaaaagcca cacataggag aatgggtagg 4620
agtaatgctt acaaaaggag acatccaaag cattatggat ccaagtctca atgaagatta 4680
tgattccggt tctgtttgga aagctgttga actagcaatg agttgtctaa atcattcttc 4740
agcgagaaga ccgaccatgt cccaagttgt tattgaattg aacgagtgtc tggcttctga 4800
aaatgcaagg ggaggagcaa gtcgggacat ggaatcaaag agttctatag aagtgagctt 4860
gacgtttggt actgaagtga gcccaaacgc tcgatagt 4898

<210> SEQ ID NO 4
<211> LENGTH: 59
<212> TYPE: DNA
<213> ORGANISM: Artificial sequence
<220> FEATURE:
<223> OTHER INFORMATION: primer: prm00405

<400> SEQUENCE: 4
ggggacaagt ttgtacaaaa aagcaggctt cacaatggag agacattttg tgtttattg 59

<210> SEQ ID NO 5
<211> LENGTH: 50
<212> TYPE: DNA
<213> ORGANISM: Artificial sequence
<220> FEATURE:
<223> OTHER INFORMATION: primer: prm00406

<400> SEQUENCE: 5
ggggaccact ttgtacaaga aagctgggtg atgcaaacta tcgagcgttt 50

<210> SEQ ID NO 6
<211> LENGTH: 2715
<212> TYPE: DNA
<213> ORGANISM: Arabidopsis thaliana

<400> SEQUENCE: 6
atggagagac attgtgtgtt agttgccact tttttgctga tgcttcatat cgttcatgct 60
caggatcaaa ttggattcat tagtgtggat tgtggtttgg cacctcgtga gtctccttac 120

```
aatgaagcca aaactggttt aacatataca tcagatgacg gtctagtcaa cgttgggaaa    180
cccggtagaa tcgccaagga attcgaaccg ctcgccgata agccgacttt gacactgaga    240
tattttccag agggagtacg aaactgctac aatctaaatg tcaccagcga caccaactat    300
ctgatcaagg ccacattcgt atatggaaat tacgatggtc ttaatgttgg gccaaacttc    360
gacctttact tcggtccgaa tttgtggact acggtatgtc ttattaagac tggaataagt    420
ataccttta taaatgtttt ggagctacga ccgatgaaga aaaacatgta cgttactcaa    480
ggcgaatcac tgaattactt attcagggtg tatattagca attcaagtac tcgtataagg    540
ttcccggatg atgtctatga tcgtaaatgg tacccgtact tcgacaactc atggacacaa    600
gtaactacga ctctcgatgt aaacacaagt cttacttatg aactaccaca aagtgtaatg    660
gcaaaagccg caacgccaat taaggctaac gacaccttga acattacatg gacagtagag    720
cctcctacta caaagtttta ctcctacatg cactttgcag agcttcagac tttaagagcc    780
aacgatgcaa gggaattcaa tgtgacgatg aatggaatat atacatatgg accttatagt    840
cctaaaccac taaaaaccga aaccatatac gacaaaatcc ctgagcaatg cgatggaggt    900
gcatgccttt tgcaggttgt gaagacactt aaatctaccc ttccaccttt acttaatgct    960
atcgaggctt tcaccgtgat tgatttcccg cagatggaga ctaatggaga tgacgttgat   1020
gcaatcaaga atgttcaaga tacgtatgga attagtagaa ttagttggca aggagatcca   1080
tgtgtcccca aactgttttt gtgggatggt ctaaattgca acaactccga taattcgaca   1140
tcaccaatca tcacttcctt agacttatct tcaagtggac taactgggag catcacccaa   1200
gccattcaga atctaactaa cctgcaagaa ctggacttgt cagataacaa tttgactgga   1260
gaaatacctg atttcttagg ggacattaaa tcactcttgg tcataaactt aagtggtaat   1320
aatctaagtg gctcagttcc tccctcactt cttcagaaga aaggaatgaa gttaaatgtc   1380
gaaggaaacc ctcatcttct ttgcacagct gattcatgtg tgaaaaaagg agaggatgga   1440
cacaagaaaa agagtgtcat agtgccagtt gttgcatcaa ttgcttcaat agctgttctt   1500
ataggtgcat tggttctgtt tttcattctt agaaagaaaa agtcaccaaa agttgaagga   1560
ccaccaccat cttatatgca agcatcagat ggtagatcgc caagatcatc tgaaccggca   1620
atagtgacaa agaatagaag gtttacttac tcacaagttg cgataatgac aaataacttc   1680
caaagaatcc ttggaaaagg agggtttgga atggtttatc atggttttgt gaacggtaca   1740
gaacaagtag ctgttaagat actctcccat tcatcgtctc aaggatataa agaatttaaa   1800
gcggaggtag aacttcttct tagagttcat cacaagaact tggtcggtct tgttgggtac   1860
tgcgacgaag gagagaacat ggctcttatc tatgaataca tggccaatgg agatctaaaa   1920
gaacatatgt caggaacacg taaccggttt actttgaatt ggggaactag actgaaaata   1980
gtcgtcgagt ctgcacaagg acttgagtac ttgcataatg gatgcaaacc accaatggtt   2040
catagagatg tcaaaaccac aaatatattg ctgaacgaac acttccaagc caaactagct   2100
gattttgggc tttcaaggtc atttccaatt gaaggtgaaa ctcatgtgtc aacagttgtt   2160
gctggaacgc ctggatatct tgatcccgaa tactataaaa caaattggtt gacagaaaag   2220
agtgatgttt atagttttgg gattgtattg ttggagctta tcacaaatcg acccgtgatc   2280
gacaaaagcc gtgaaaagcc acatatagca gaatgggtag gagtaatgct tacaaaagga   2340
gacatcaaca gtatcatgga tcctaattta aatgaagatt atgattctgg ttctgtttgg   2400
aaagctgttg agctagccat gagttgtctc aatccttctt cagcaagaag accgaccatg   2460
tcccaagttg ttattgaact aaacgagtgt atagcatcag aaaattcaag ggaggagcg    2520
```

agtcgggata tggactcgaa gagttccata gaagtgagct tgacctttga taccgaactg 2580
agcccaacgg ctcggtagtt tacataaatt catattttcg ccatatgtaa cgtggatttt 2640
tatttatttt ctatttcatg taatgaaatt tgtctatgtg atatatatct ttgttaatga 2700
gcaatgaact tcttt 2715

<210> SEQ ID NO 7
<211> LENGTH: 865
<212> TYPE: PRT
<213> ORGANISM: Arabidopsis thaliana

<400> SEQUENCE: 7

```
Met Glu Arg His Cys Val Leu Val Ala Thr Phe Leu Leu Met Leu His
1               5                   10                  15

Ile Val His Ala Gln Asp Gln Ile Gly Phe Ile Ser Val Asp Cys Gly
            20                  25                  30

Leu Ala Pro Arg Glu Ser Pro Tyr Asn Glu Ala Lys Thr Gly Leu Thr
        35                  40                  45

Tyr Thr Ser Asp Asp Gly Leu Val Asn Val Gly Lys Pro Gly Arg Ile
    50                  55                  60

Ala Lys Glu Phe Glu Pro Leu Ala Asp Lys Pro Thr Leu Thr Leu Arg
65                  70                  75                  80

Tyr Phe Pro Glu Gly Val Arg Asn Cys Tyr Asn Leu Asn Val Thr Ser
                85                  90                  95

Asp Thr Asn Tyr Leu Ile Lys Ala Thr Phe Val Tyr Gly Asn Tyr Asp
            100                 105                 110

Gly Leu Asn Val Gly Pro Asn Phe Asp Leu Tyr Phe Gly Pro Asn Leu
        115                 120                 125

Trp Thr Thr Val Cys Leu Ile Lys Thr Gly Ile Ser Ile Pro Phe Ile
    130                 135                 140

Asn Val Leu Glu Leu Arg Pro Met Lys Lys Asn Met Tyr Val Thr Gln
145                 150                 155                 160

Gly Glu Ser Leu Asn Tyr Leu Phe Arg Val Tyr Ile Ser Asn Ser Ser
                165                 170                 175

Thr Arg Ile Arg Phe Pro Asp Asp Val Tyr Asp Arg Lys Trp Tyr Pro
            180                 185                 190

Tyr Phe Asp Asn Ser Trp Thr Gln Val Thr Thr Thr Leu Asp Val Asn
        195                 200                 205

Thr Ser Leu Thr Tyr Glu Leu Pro Gln Ser Val Met Ala Lys Ala Ala
    210                 215                 220

Thr Pro Ile Lys Ala Asn Asp Thr Leu Asn Ile Thr Trp Thr Val Glu
225                 230                 235                 240

Pro Pro Thr Thr Lys Phe Tyr Ser Tyr Met His Phe Ala Glu Leu Gln
                245                 250                 255

Thr Leu Arg Ala Asn Asp Ala Arg Glu Phe Asn Val Thr Met Asn Gly
            260                 265                 270

Ile Tyr Thr Tyr Gly Pro Tyr Ser Pro Lys Pro Leu Lys Thr Glu Thr
        275                 280                 285

Ile Tyr Asp Lys Ile Pro Glu Gln Cys Asp Gly Gly Ala Cys Leu Leu
    290                 295                 300

Gln Val Val Lys Thr Leu Lys Ser Thr Leu Pro Pro Leu Leu Asn Ala
305                 310                 315                 320

Ile Glu Ala Phe Thr Val Ile Asp Phe Pro Gln Met Glu Thr Asn Gly
                325                 330                 335
```

```
Asp Asp Val Asp Ala Ile Lys Asn Val Gln Asp Thr Tyr Gly Ile Ser
            340                 345                 350

Arg Ile Ser Trp Gln Gly Asp Pro Cys Val Pro Lys Leu Phe Leu Trp
        355                 360                 365

Asp Gly Leu Asn Cys Asn Asn Ser Asp Asn Ser Thr Ser Pro Ile Ile
    370                 375                 380

Thr Ser Leu Asp Leu Ser Ser Ser Gly Leu Thr Gly Ser Ile Thr Gln
385                 390                 395                 400

Ala Ile Gln Asn Leu Thr Asn Leu Gln Glu Leu Asp Leu Ser Asp Asn
                405                 410                 415

Asn Leu Thr Gly Glu Ile Pro Asp Phe Leu Gly Asp Ile Lys Ser Leu
            420                 425                 430

Leu Val Ile Asn Leu Ser Gly Asn Asn Leu Ser Gly Ser Val Pro Pro
        435                 440                 445

Ser Leu Leu Gln Lys Lys Gly Met Lys Leu Asn Val Glu Gly Asn Pro
    450                 455                 460

His Leu Leu Cys Thr Ala Asp Ser Cys Val Lys Lys Gly Glu Asp Gly
465                 470                 475                 480

His Lys Lys Lys Ser Val Ile Val Pro Val Val Ala Ser Ile Ala Ser
                485                 490                 495

Ile Ala Val Leu Ile Gly Ala Leu Val Leu Phe Phe Ile Leu Arg Lys
            500                 505                 510

Lys Lys Ser Pro Lys Val Glu Gly Pro Pro Pro Ser Tyr Met Gln Ala
        515                 520                 525

Ser Asp Gly Arg Ser Pro Arg Ser Ser Glu Pro Ala Ile Val Thr Lys
    530                 535                 540

Asn Arg Arg Phe Thr Tyr Ser Gln Val Ala Ile Met Thr Asn Asn Phe
545                 550                 555                 560

Gln Arg Ile Leu Gly Lys Gly Gly Phe Gly Met Val Tyr His Gly Phe
                565                 570                 575

Val Asn Gly Thr Glu Gln Val Ala Val Lys Ile Leu Ser His Ser Ser
            580                 585                 590

Ser Gln Gly Tyr Lys Glu Phe Lys Ala Glu Val Glu Leu Leu Leu Arg
        595                 600                 605

Val His His Lys Asn Leu Val Gly Leu Val Gly Tyr Cys Asp Glu Gly
    610                 615                 620

Glu Asn Met Ala Leu Ile Tyr Glu Tyr Met Ala Asn Gly Asp Leu Lys
625                 630                 635                 640

Glu His Met Ser Gly Thr Arg Asn Arg Phe Thr Leu Asn Trp Gly Thr
                645                 650                 655

Arg Leu Lys Ile Val Val Glu Ser Ala Gln Gly Leu Glu Tyr Leu His
            660                 665                 670

Asn Gly Cys Lys Pro Pro Met Val His Arg Asp Val Lys Thr Thr Asn
        675                 680                 685

Ile Leu Leu Asn Glu His Phe Gln Ala Lys Leu Ala Asp Phe Gly Leu
    690                 695                 700

Ser Arg Ser Phe Pro Ile Glu Gly Glu Thr His Val Ser Thr Val Val
705                 710                 715                 720

Ala Gly Thr Pro Gly Tyr Leu Asp Pro Glu Tyr Tyr Lys Thr Asn Trp
                725                 730                 735

Leu Thr Glu Lys Ser Asp Val Tyr Ser Phe Gly Ile Val Leu Leu Glu
            740                 745                 750

Leu Ile Thr Asn Arg Pro Val Ile Asp Lys Ser Arg Glu Lys Pro His
        755                 760                 765
```

```
Ile Ala Glu Trp Val Gly Val Met Leu Thr Lys Gly Asp Ile Asn Ser
    770                 775                 780

Ile Met Asp Pro Asn Leu Asn Glu Asp Tyr Asp Ser Gly Ser Val Trp
785                 790                 795                 800

Lys Ala Val Glu Leu Ala Met Ser Cys Leu Asn Pro Ser Ser Ala Arg
                805                 810                 815

Arg Pro Thr Met Ser Gln Val Val Ile Glu Leu Asn Glu Cys Ile Ala
            820                 825                 830

Ser Glu Asn Ser Arg Gly Gly Ala Ser Arg Asp Met Asp Ser Lys Ser
        835                 840                 845

Ser Ile Glu Val Ser Leu Thr Phe Asp Thr Glu Leu Ser Pro Thr Ala
    850                 855                 860

Arg
865


<210> SEQ ID NO 8
<211> LENGTH: 2028
<212> TYPE: DNA
<213> ORGANISM: Arabidopsis thaliana

<400> SEQUENCE: 8

atgacagttt tttttataaa cgattgtgtc aggttcccgg atgatgtgta tgaccgaaaa      60

tggtacccga tcttccagaa ctcatggacg caagtaacta cgaatctcaa tgtaaatatt     120

agcactattt atgaactacc acaaagcgta atgtcaacag ccgcgacgcc gctaaatgct     180

aatgcgacct tgaacattac atggacaata gagcctccta ctacaccatt ttactcctac     240

attcactttg cagagcttca atctctaagg gccaatgata caagagaatt caatgtgacg     300

ttgaatgggg agtatacaat tggaccttat agtcctaaac cgctaaaaac cgaaaccata     360

caagacttaa gccccgagca atgtaatgga ggggcgtgta ttttgcagct tgtggagacg     420

ctgaaatcaa ctcttccgcc tttacttaat gctattgagg ctttcactgt gattgatttc     480

ccgcaaatgg agacaaatga agatgatgtt actggtatca acgatgttca aaacacttat     540

ggattgaata gaatcagttg gcaaggagat ccatgtgtcc ccaaacagta ttcgtgggac     600

ggtctaaatt gcaacaactc agatatctct ataccaccaa taatcatttc cttagattta     660

tcttcaagtg gtttaaatgg ggtcattaca caaggcattc aaaatctaac ccatcttcaa     720

tacttggact tgtcagataa taatttaact ggtgatatac ctaaatttct agctgacata     780

caatcactct tggttataaa cttaagtggt aataatctca ctggatcggt gcctctctca     840

cttcttcaga agaaaggatt gaaattaaat gtcgaaggca accctcatct tctttgcaca     900

gatggtttat gtgttaacaa aggagatgga cataagaaaa agagcatcat agcaccagtg     960

gtcgcatcaa ttgcttcaat agctattctt ataggtgcat tggttctgtt ttttgttctt    1020

aaaaagaaaa cgcaatcaaa agaaccagca atagtgacga agaataaacg gtttacttac    1080

tctgaagtta tgcaaatgac aaataacttc caaagagtgc ttgggaaagg agggtttgga    1140

attgtttatc atggtttggt gaatggtact gaacaagtag ctattaagat actctcccat    1200

tcttcatctc aaggatataa acaattcaaa gctgaggtag aacttcttct tagagttcat    1260

cacaagaatt tggtaggcct tgttggatac tgtgacgaag gagagaactt ggctcttata    1320

tatgaataca tggccaatgg agatttaaaa gaacacatgt caggaacacg aaaccacttc    1380

attttaaatt ggggaactag actaaaaata gtcgttgaat ctgcccaagg acttgagtat    1440

ttgcacaatg gatgcaaacc actaatggtg catagagaca tcaaaacaac aaatatattg    1500
```

```
ttgaatgaac aatttgatgc caaacttgct gattttgggc tctcgagatc attcccgatt   1560

gaaggtgaaa ctcatgtttc aacagctgtt gctggaactc ctggatatct cgatcccgaa   1620

tactacagaa caaattggtt gactgaaaag agtgatgttt atagtttcgg agtcgtattg   1680

ttagagatca tcacaaacca acccgtgata gacccaagac gtgaaaagcc acatatagca   1740

gaatgggttg ggaagtgctt tacaaaagga gacataaaaa atataatgga tccaagtcta   1800

aatggagatt atgattccac ttctgtttgg aaagctgttg agctagcgat gtgttgtctt   1860

aatccttcat cagctagaag accgaacatg tctcaagttg ttattgaatt aaacgagtgt   1920

ttgacatctg aaaattcaag ggaggaggcg attcgagaca tggactcaga aggttctata   1980

gaagtaagct tgacctttgg taccgaagtg accccattgg ctcggtag                2028
```

<210> SEQ ID NO 9
<211> LENGTH: 675
<212> TYPE: PRT
<213> ORGANISM: Arabidopsis thaliana

<400> SEQUENCE: 9

```
Met Thr Val Phe Phe Ile Asn Asp Cys Val Arg Phe Pro Asp Asp Val
1               5                   10                  15

Tyr Asp Arg Lys Trp Tyr Pro Ile Phe Gln Asn Ser Trp Thr Gln Val
            20                  25                  30

Thr Thr Asn Leu Asn Val Asn Ile Ser Thr Ile Tyr Glu Leu Pro Gln
        35                  40                  45

Ser Val Met Ser Thr Ala Ala Thr Pro Leu Asn Ala Asn Ala Thr Leu
    50                  55                  60

Asn Ile Thr Trp Thr Ile Glu Pro Pro Thr Thr Pro Phe Tyr Ser Tyr
65                  70                  75                  80

Ile His Phe Ala Glu Leu Gln Ser Leu Arg Ala Asn Asp Thr Arg Glu
                85                  90                  95

Phe Asn Val Thr Leu Asn Gly Glu Tyr Thr Ile Gly Pro Tyr Ser Pro
            100                 105                 110

Lys Pro Leu Lys Thr Glu Thr Ile Gln Asp Leu Ser Pro Glu Gln Cys
        115                 120                 125

Asn Gly Gly Ala Cys Ile Leu Gln Leu Val Glu Thr Leu Lys Ser Thr
    130                 135                 140

Leu Pro Pro Leu Leu Asn Ala Ile Glu Ala Phe Thr Val Ile Asp Phe
145                 150                 155                 160

Pro Gln Met Glu Thr Asn Glu Asp Asp Val Thr Gly Ile Asn Asp Val
                165                 170                 175

Gln Asn Thr Tyr Gly Leu Asn Arg Ile Ser Trp Gln Gly Asp Pro Cys
            180                 185                 190

Val Pro Lys Gln Tyr Ser Trp Asp Gly Leu Asn Cys Asn Asn Ser Asp
        195                 200                 205

Ile Ser Ile Pro Pro Ile Ile Ile Ser Leu Asp Leu Ser Ser Ser Gly
    210                 215                 220

Leu Asn Gly Val Ile Thr Gln Gly Ile Gln Asn Leu Thr His Leu Gln
225                 230                 235                 240

Tyr Leu Asp Leu Ser Asp Asn Asn Leu Thr Gly Asp Ile Pro Lys Phe
                245                 250                 255

Leu Ala Asp Ile Gln Ser Leu Leu Val Ile Asn Leu Ser Gly Asn Asn
            260                 265                 270

Leu Thr Gly Ser Val Pro Leu Ser Leu Leu Gln Lys Lys Gly Leu Lys
        275                 280                 285
```

```
Leu Asn Val Glu Gly Asn Pro His Leu Leu Cys Thr Asp Gly Leu Cys
    290                 295                 300

Val Asn Lys Gly Asp Gly His Lys Lys Lys Ser Ile Ile Ala Pro Val
305                 310                 315                 320

Val Ala Ser Ile Ala Ser Ile Ala Ile Leu Ile Gly Ala Leu Val Leu
                325                 330                 335

Phe Phe Val Leu Lys Lys Lys Thr Gln Ser Lys Glu Pro Ala Ile Val
            340                 345                 350

Thr Lys Asn Lys Arg Phe Thr Tyr Ser Glu Val Met Gln Met Thr Asn
        355                 360                 365

Asn Phe Gln Arg Val Leu Gly Lys Gly Gly Phe Gly Ile Val Tyr His
    370                 375                 380

Gly Leu Val Asn Gly Thr Glu Gln Val Ala Ile Lys Ile Leu Ser His
385                 390                 395                 400

Ser Ser Ser Gln Gly Tyr Lys Gln Phe Lys Ala Glu Val Glu Leu Leu
                405                 410                 415

Leu Arg Val His His Lys Asn Leu Val Gly Leu Val Gly Tyr Cys Asp
            420                 425                 430

Glu Gly Glu Asn Leu Ala Leu Ile Tyr Glu Tyr Met Ala Asn Gly Asp
        435                 440                 445

Leu Lys Glu His Met Ser Gly Thr Arg Asn His Phe Ile Leu Asn Trp
    450                 455                 460

Gly Thr Arg Leu Lys Ile Val Val Glu Ser Ala Gln Gly Leu Glu Tyr
465                 470                 475                 480

Leu His Asn Gly Cys Lys Pro Leu Met Val His Arg Asp Ile Lys Thr
                485                 490                 495

Thr Asn Ile Leu Leu Asn Glu Gln Phe Asp Ala Lys Leu Ala Asp Phe
            500                 505                 510

Gly Leu Ser Arg Ser Phe Pro Ile Glu Gly Glu Thr His Val Ser Thr
        515                 520                 525

Ala Val Ala Gly Thr Pro Gly Tyr Leu Asp Pro Glu Tyr Tyr Arg Thr
    530                 535                 540

Asn Trp Leu Thr Glu Lys Ser Asp Val Tyr Ser Phe Gly Val Val Leu
545                 550                 555                 560

Leu Glu Ile Ile Thr Asn Gln Pro Val Ile Asp Pro Arg Arg Glu Lys
                565                 570                 575

Pro His Ile Ala Glu Trp Val Gly Glu Val Leu Thr Lys Gly Asp Ile
            580                 585                 590

Lys Asn Ile Met Asp Pro Ser Leu Asn Gly Asp Tyr Asp Ser Thr Ser
        595                 600                 605

Val Trp Lys Ala Val Glu Leu Ala Met Cys Cys Leu Asn Pro Ser Ser
    610                 615                 620

Ala Arg Arg Pro Asn Met Ser Gln Val Val Ile Glu Leu Asn Glu Cys
625                 630                 635                 640

Leu Thr Ser Glu Asn Ser Arg Gly Gly Ala Ile Arg Asp Met Asp Ser
                645                 650                 655

Glu Gly Ser Ile Glu Val Ser Leu Thr Phe Gly Thr Glu Val Thr Pro
            660                 665                 670

Leu Ala Arg
        675
```

<210> SEQ ID NO 10
<211> LENGTH: 2964
<212> TYPE: DNA
<213> ORGANISM: Arabidopsis thaliana

<400> SEQUENCE: 10

```
gagaaatacc tcatatacat aatcataaac ttatatgcat agctttgcta actcaaaaaa     60
aaaaacagat cccttctttg catagtaagg aagatattaa tggagagtca tcgtgtgttc    120
gttgccactt ttatgctgat acttcatctt gttcaagctc aagatcaacc cggattcatc    180
aatgtggatt gcggtttact ccctcgtgat tctccttaca acgcactcgg aaccggttta    240
gtatatacat cagatgtcgg tttagttagc agtgggaaaa ctggtaaaat cgccaaggaa    300
ttcgaagaga acaacagtac accgaatttg acattgagat actttccaga cggagcacga    360
aactgctaca acttaaacgt gagccgtgac accaactata tgatcaaggc tacattcgtg    420
tatggaaatt acgatggtca taaagatgag ccgaacttcg acctttactt gggtccaaat    480
ttatgggcaa cggtaagccg cagtgaaact gttgaggaga tcatccatgt gacgaaatcc    540
gattcgttac aggtttgtct tgctaagacg ggagatttta taccttttat taatatcttg    600
gagctacgac cattgaagaa aaatgtgtac gttacagaaa gtggctcact caagctctta    660
tttaggaagt attttagtga ctcaggtcaa acgataaggt atccagatga tatctatgac    720
cgtgtatggc atgcatcctt cctggaaaat aattgggcac aagtatcgac gactttgggt    780
gtaaacgtta ctgataatta tgatttatca caagatgtaa tggcaacggg cgcaacacct    840
ctaaacgata gtgagacatt gaacattaca tggaacgtag agcctcctac tacaaaggtt    900
tactcctaca tgcactttgc agagcttgag acactaaggg ccaacgatac aagggaattc    960
aatgtgatgc tgaatggaaa tgacttgttt ggaccttaca gtccaatacc gctaaagacc   1020
gaaacagaaa ccaacttaaa accagaggaa tgcgaagatg ggcatgtat tttgcagctt    1080
gtgaagacgt caaaatcaac tcttccgcct ttacttaatg ctatagaggc tttcaccgtg   1140
attgatttcc tacaagtgga gacagatgaa gatgacgctg ctgctatcaa gaatgttcaa   1200
aatgcttatg gattgattaa tagaagcagt tggcaaggag atccatgtgt ccccaaacag   1260
tattcgtggg acggtctaaa gtgcagttac tcagatagta ctccaccaat aattaatttc   1320
ttagacttat ctgcaagtgg actaaccggg atcatcgcgc ctgccattca aaatcttact   1380
cacctagaaa tattggcctt gtcaaataac aatttgaccg gagaagtacc tgaatttcta   1440
gctgacttaa aatcaatcat ggtcatagac ttaagaggca ataacctcag tggcccggtt   1500
cctgcctcac ttcttcagaa gaaaggattg atgctacatc ttgatgacaa tccccatatt   1560
ctttgcacaa ctggttcatg tatgcacaaa ggagaaggcg aaaaaaagag tatcattgta   1620
ccagtggttg catcaattgt ttcattggct gttattatag gtgcactcat tctgttcctt   1680
gttttccgaa agaaaaaggc atcaaaagtt gaagggacac taccatctta catgcaagca   1740
tcagatggta gatcgccgag atcctctgaa ccagcaatag tgacgaaaaa caaaaggttt   1800
acttactcac aagttgtgat aatgacaaat aacttccaaa gaatccttgg gaaaggaggg   1860
tttggaatcg tttatcatgg ctttgtgaac ggtgttgaac aagtagctgt taagatactc   1920
tctcattcat catctcaagg gtataaacaa ttcaaagctg aggtagaact tcttcttaga   1980
gttcatcaca agaatttggt tggtcttgtt gggtattgcg acgaaggaga gaacatggct   2040
cttatctatg aatacatggc caatggagat ttaaaagaac atatgtcagg aacaagaaac   2100
cgatttattt taaattggga aactagacta aaaatagtca ttgactctgc gcaagggctt   2160
gagtatttgc ataatggatg caaaccacta atggtacaca gggacgtcaa aactacaaat   2220
atattgttaa atgaacactt tgaagccaaa cttgctgatt ttgggctttc aaggtctttt   2280
ccgattggag gtgaaactca tgtgtcaaca gttgttgctg gaactcctgg atatctcgat   2340
```

```
cctgaatatt acaaaacaaa tcggttgaca gagaagagtg atgtatatag ttttgggatt   2400

gtattgttgg agatgatcac aaatcggcca gtgatagacc aaagccgtga aaagccatat   2460

atttcagaat gggtggggat aatgcttacg aaaggagaca tcattagcat tatggatcca   2520

agtctaaatg gagactatga ttctggttct gtgtggaaag ctgttgaact agcaatgtct   2580

tgtctgaatc cttcttcaac aagaagacct accatgtctc aagttcttat tgcattaaac   2640

gaatgtttgg tatctgaaaa ttcaagggga ggagcgagta gggacatgga ctcaaagagt   2700

tccctagagg taagcttgac atttgatact gatgtgagcc caatggctag gtagattaca   2760

tgaaatatta tcatgcggta tcacataaat ttgtttatat gtttttattt acagaactat   2820

cctcaaatta gtatctctct tataggccac ctttgttaat gaactctgaa ctttttgtca   2880

ttgatacatg tgtgaataac agtccaaagt ctattattgt tccgccgtaa tgtatcagtt   2940

tcaaatcagt gcatttttg tttg                                           2964
```

```
<210> SEQ ID NO 11
<211> LENGTH: 884
<212> TYPE: PRT
<213> ORGANISM: Arabidopsis thaliana

<400> SEQUENCE: 11

Met Glu Ser His Arg Val Phe Val Ala Thr Phe Met Leu Ile Leu His
1               5                   10                  15

Leu Val Gln Ala Gln Asp Gln Pro Gly Phe Ile Asn Val Asp Cys Gly
            20                  25                  30

Leu Leu Pro Arg Asp Ser Pro Tyr Asn Ala Leu Gly Thr Gly Leu Val
        35                  40                  45

Tyr Thr Ser Asp Val Gly Leu Val Ser Ser Gly Lys Thr Gly Lys Ile
    50                  55                  60

Ala Lys Glu Phe Glu Glu Asn Asn Ser Thr Pro Asn Leu Thr Leu Arg
65                  70                  75                  80

Tyr Phe Pro Asp Gly Ala Arg Asn Cys Tyr Asn Leu Asn Val Ser Arg
                85                  90                  95

Asp Thr Asn Tyr Met Ile Lys Ala Thr Phe Val Tyr Gly Asn Tyr Asp
            100                 105                 110

Gly His Lys Asp Glu Pro Asn Phe Asp Leu Tyr Leu Gly Pro Asn Leu
        115                 120                 125

Trp Ala Thr Val Ser Arg Ser Glu Thr Val Glu Glu Ile Ile His Val
    130                 135                 140

Thr Lys Ser Asp Ser Leu Gln Val Cys Leu Ala Lys Thr Gly Asp Phe
145                 150                 155                 160

Ile Pro Phe Ile Asn Ile Leu Glu Leu Arg Pro Leu Lys Lys Asn Val
                165                 170                 175

Tyr Val Thr Glu Ser Gly Ser Leu Lys Leu Leu Phe Arg Lys Tyr Phe
            180                 185                 190

Ser Asp Ser Gly Gln Thr Ile Arg Tyr Pro Asp Asp Ile Tyr Asp Arg
        195                 200                 205

Val Trp His Ala Ser Phe Leu Glu Asn Asn Trp Ala Gln Val Ser Thr
    210                 215                 220

Thr Leu Gly Val Asn Val Thr Asp Asn Tyr Asp Leu Ser Gln Asp Val
225                 230                 235                 240

Met Ala Thr Gly Ala Thr Pro Leu Asn Asp Ser Glu Thr Leu Asn Ile
                245                 250                 255

Thr Trp Asn Val Glu Pro Pro Thr Thr Lys Val Tyr Ser Tyr Met His
```

```
            260                 265                 270

Phe Ala Glu Leu Glu Thr Leu Arg Ala Asn Asp Thr Arg Glu Phe Asn
        275                 280                 285

Val Met Leu Asn Gly Asn Asp Leu Phe Gly Pro Tyr Ser Pro Ile Pro
    290                 295                 300

Leu Lys Thr Glu Thr Glu Thr Asn Leu Lys Pro Glu Glu Cys Glu Asp
305                 310                 315                 320

Gly Ala Cys Ile Leu Gln Leu Val Lys Thr Ser Lys Ser Thr Leu Pro
                325                 330                 335

Pro Leu Leu Asn Ala Ile Glu Ala Phe Thr Val Ile Asp Phe Leu Gln
            340                 345                 350

Val Glu Thr Asp Glu Asp Asp Ala Ala Ala Ile Lys Asn Val Gln Asn
        355                 360                 365

Ala Tyr Gly Leu Ile Asn Arg Ser Ser Trp Gln Gly Asp Pro Cys Val
    370                 375                 380

Pro Lys Gln Tyr Ser Trp Asp Gly Leu Lys Cys Ser Tyr Ser Asp Ser
385                 390                 395                 400

Thr Pro Pro Ile Ile Asn Phe Leu Asp Leu Ser Ala Ser Gly Leu Thr
                405                 410                 415

Gly Ile Ile Ala Pro Ala Ile Gln Asn Leu Thr His Leu Glu Ile Leu
            420                 425                 430

Ala Leu Ser Asn Asn Asn Leu Thr Gly Glu Val Pro Glu Phe Leu Ala
        435                 440                 445

Asp Leu Lys Ser Ile Met Val Ile Asp Leu Arg Gly Asn Asn Leu Ser
    450                 455                 460

Gly Pro Val Pro Ala Ser Leu Leu Gln Lys Lys Gly Leu Met Leu His
465                 470                 475                 480

Leu Asp Asp Asn Pro His Ile Leu Cys Thr Thr Gly Ser Cys Met His
                485                 490                 495

Lys Gly Glu Gly Glu Lys Lys Ser Ile Ile Val Pro Val Val Ala Ser
            500                 505                 510

Ile Val Ser Leu Ala Val Ile Ile Gly Ala Leu Ile Leu Phe Leu Val
        515                 520                 525

Phe Arg Lys Lys Lys Ala Ser Lys Val Glu Gly Thr Leu Pro Ser Tyr
    530                 535                 540

Met Gln Ala Ser Asp Gly Arg Ser Pro Arg Ser Ser Glu Pro Ala Ile
545                 550                 555                 560

Val Thr Lys Asn Lys Arg Phe Thr Tyr Ser Gln Val Val Ile Met Thr
                565                 570                 575

Asn Asn Phe Gln Arg Ile Leu Gly Lys Gly Gly Phe Gly Ile Val Tyr
            580                 585                 590

His Gly Phe Val Asn Gly Val Glu Gln Val Ala Val Lys Ile Leu Ser
        595                 600                 605

His Ser Ser Ser Gln Gly Tyr Lys Gln Phe Lys Ala Glu Val Glu Leu
    610                 615                 620

Leu Leu Arg Val His His Lys Asn Leu Val Gly Leu Val Gly Tyr Cys
625                 630                 635                 640

Asp Glu Gly Glu Asn Met Ala Leu Ile Tyr Glu Tyr Met Ala Asn Gly
                645                 650                 655

Asp Leu Lys Glu His Met Ser Gly Thr Arg Asn Arg Phe Ile Leu Asn
            660                 665                 670

Trp Glu Thr Arg Leu Lys Ile Val Ile Asp Ser Ala Gln Gly Leu Glu
        675                 680                 685
```

```
Tyr Leu His Asn Gly Cys Lys Pro Leu Met Val His Arg Asp Val Lys
    690                 695                 700

Thr Thr Asn Ile Leu Leu Asn Glu His Phe Glu Ala Lys Leu Ala Asp
705                 710                 715                 720

Phe Gly Leu Ser Arg Ser Phe Pro Ile Gly Gly Glu Thr His Val Ser
                725                 730                 735

Thr Val Val Ala Gly Thr Pro Gly Tyr Leu Asp Pro Glu Tyr Tyr Lys
            740                 745                 750

Thr Asn Arg Leu Thr Glu Lys Ser Asp Val Tyr Ser Phe Gly Ile Val
        755                 760                 765

Leu Leu Glu Met Ile Thr Asn Arg Pro Val Ile Asp Gln Ser Arg Glu
    770                 775                 780

Lys Pro Tyr Ile Ser Glu Trp Val Gly Ile Met Leu Thr Lys Gly Asp
785                 790                 795                 800

Ile Ile Ser Ile Met Asp Pro Ser Leu Asn Gly Asp Tyr Asp Ser Gly
                805                 810                 815

Ser Val Trp Lys Ala Val Glu Leu Ala Met Ser Cys Leu Asn Pro Ser
            820                 825                 830

Ser Thr Arg Arg Pro Thr Met Ser Gln Val Leu Ile Ala Leu Asn Glu
        835                 840                 845

Cys Leu Val Ser Glu Asn Ser Arg Gly Gly Ala Ser Arg Asp Met Asp
    850                 855                 860

Ser Lys Ser Ser Leu Glu Val Ser Leu Thr Phe Asp Thr Asp Val Ser
865                 870                 875                 880

Pro Met Ala Arg


<210> SEQ ID NO 12
<211> LENGTH: 2532
<212> TYPE: DNA
<213> ORGANISM: Arabidopsis thaliana

<400> SEQUENCE: 12

atggagagac attgtttgtt ctttgtgatt ttttccctta tactacatct tgttcaagct      60

caggacccaa taggctctcc ttacaaagaa tcctcgaccg gtctaacata tacgtcagac     120

gatggtttcg tccagagcgg gaaaattggt aaaatcacca aggaactcga gtcattatac     180

aagaaaccgg agcggacgct aagatacttt cctgatggag taagaaattg tttcagtctg     240

aatgtcacaa ggggaacaaa gtatctaatc aagccaacct ttctctatgg aaactatgat     300

ggtcgtaatg tcatcccgga ttttgatctt tacatcggcc caaatatgtg gatcacggtg     360

aatactgata acactatcaa ggagatcctc cacgtatcga aatcaaacac tttgcaagtg     420

tgtcttgtta agacaggtac aagtatacct tatataaata cattggaact acgaccattg     480

gccgacgata tatacaccaa cgaaagtggc tccctcaact atctttttcg ggtttattat     540

agcaatttaa agggctatat agagtacccc gatgatgtcc acgatcgcat atggaaacaa     600

atcctacctt accaggattg gcagatttta actacgaatc tccaaataaa cgtttctaat     660

gattatgatc taccccaacg tgtaatgaaa acagctgtaa cacccattaa agctagcaca     720

acgacgatgg aatttccctg gaacttagag cctccaactt cacagtttta cttattcctt     780

cactttgcag agcttcaaag tctacaagcc aacgagacga gggaattcaa tgtggtgttg     840

aacggaaatg ttacatttaa atcttatagt cctaagtttt tagaaatgca aacagtatat     900

agcacagcac caaagcaatg cgatggaggg aaatgcttgt tgcagttagt gaaaacgtca     960

aggtccactt tgccgcctct aattaatgct atggaggctt acactgtgct tgatttccca    1020
```

```
cagatagaaa caaatgtaga tgaagtgatt gctatcaaga atatacaatc tacttatgga   1080

ttgagtaaaa caacctggca aggagatcca tgtgtaccca aaaagttctt gtgggatggt   1140

ttaaactgca acaactcgga tgattctacg ccaccaatta tcacttcctt tggattgact   1200

ggaattatcg tgctgaccat tcagaatctc gccaatttac aagaactgga cttgtcaaat   1260

aacaacttgt ctggaggtgt tcctgaattt ctagcggata tgaagtcgct cttggtcata   1320

aacttaagtg ggaacaatct cagtggtgta gttcctcaaa agcttataga gaagaaaatg   1380

ttgaaattga acattgaagg caatccgaag cttaattgca cagtggagtc atgtgtaaac   1440

aaagatgaag agggtggacg acagataaag agcatgacaa tcccaattgt ggcatcaatt   1500

ggttctgttg ttgccttcac agttgcattg atgatatttt gtgttgttcg aaagaataac   1560

ccgtcaaacg atgaagctcc aacatcatgt atgctacccg cggatagtag atcatctgaa   1620

ccgacaatag tgacgaagaa taaaaaattt acgtatgcgg aggttttaac catgacaaac   1680

aatttccaaa aaatccttgg aaaaggagga tttggaattg tatattatgg ttcagtaaac   1740

ggtacagagc aggttgctgt gaaaatgctt tcccattcat cagctcaagg atataagcaa   1800

tttaaagctg aggttgaact tcttcttaga gtacatcaca agaatttggt aggccttgtc   1860

gggtattgcg aagaaggaga taaattggct ctcatctacg aatacatggc caatggagac   1920

ttagatgagc atatgtcagg aaaacgaggt ggttctatat taaattgggg aacaaggcta   1980

aagatagctc tcgaggctgc acaaggatta gagtacttgc ataatggatg caaaccctta   2040

atggttcata gagatgttaa aaccacaaat atattgttga atgaacattt cgataccaaa   2100

cttgctgatt ttgggctttc gagatcattc ccgatagaag ggaaactca tgtatcaact   2160

gttgttgctg gaactattgg ttacctcgat cccgatgatg tgtatagttt tggagttgta   2220

ttattggtga tgattacaaa ccaacccgtg atagaccaaa accgcgaaaa gagacatata   2280

gcagaatggg tgggaggaat gcttacgaaa ggagacatca aaagtattac tgatccaaat   2340

ctccttggag attataattc tggttctgtt tggaaagctg ttgaactagc aatgtcatgt   2400

atgaatcctt cttcgatgac aagaccgaca atgtctcaag ttgtttttga actgaaagag   2460

tgtttggcct ctgaaagctc cagggaagtg agcatgacct tcggaactga agtggcccct   2520

atggctcggt ag                                                        2532
```

<210> SEQ ID NO 13
<211> LENGTH: 843
<212> TYPE: PRT
<213> ORGANISM: Arabidopsis thaliana

<400> SEQUENCE: 13

```
Met Glu Arg His Cys Leu Phe Phe Val Ile Phe Ser Leu Ile Leu His
1               5                   10                  15

Leu Val Gln Ala Gln Asp Pro Ile Gly Ser Pro Tyr Lys Glu Ser Ser
            20                  25                  30

Thr Gly Leu Thr Tyr Thr Ser Asp Asp Gly Phe Val Gln Ser Gly Lys
        35                  40                  45

Ile Gly Lys Ile Thr Lys Glu Leu Glu Ser Leu Tyr Lys Lys Pro Glu
    50                  55                  60

Arg Thr Leu Arg Tyr Phe Pro Asp Gly Val Arg Asn Cys Phe Ser Leu
65                  70                  75                  80

Asn Val Thr Arg Gly Thr Lys Tyr Leu Ile Lys Pro Thr Phe Leu Tyr
                85                  90                  95

Gly Asn Tyr Asp Gly Arg Asn Val Ile Pro Asp Phe Asp Leu Tyr Ile
            100                 105                 110
```

```
Gly Pro Asn Met Trp Ile Thr Val Asn Thr Asp Asn Thr Ile Lys Glu
        115                 120                 125

Ile Leu His Val Ser Lys Ser Asn Thr Leu Gln Val Cys Leu Val Lys
    130                 135                 140

Thr Gly Thr Ser Ile Pro Tyr Ile Asn Thr Leu Glu Leu Arg Pro Leu
145                 150                 155                 160

Ala Asp Asp Ile Tyr Thr Asn Glu Ser Gly Ser Leu Asn Tyr Leu Phe
                165                 170                 175

Arg Val Tyr Tyr Ser Asn Leu Lys Gly Tyr Ile Glu Tyr Pro Asp Asp
            180                 185                 190

Val His Asp Arg Ile Trp Lys Gln Ile Leu Pro Tyr Gln Asp Trp Gln
        195                 200                 205

Ile Leu Thr Thr Asn Leu Gln Ile Asn Val Ser Asn Asp Tyr Asp Leu
    210                 215                 220

Pro Gln Arg Val Met Lys Thr Ala Val Thr Pro Ile Lys Ala Ser Thr
225                 230                 235                 240

Thr Thr Met Glu Phe Pro Trp Asn Leu Glu Pro Pro Thr Ser Gln Phe
                245                 250                 255

Tyr Leu Phe Leu His Phe Ala Glu Leu Gln Ser Leu Gln Ala Asn Glu
            260                 265                 270

Thr Arg Glu Phe Asn Val Val Leu Asn Gly Asn Val Thr Phe Lys Ser
        275                 280                 285

Tyr Ser Pro Lys Phe Leu Glu Met Gln Thr Val Tyr Ser Thr Ala Pro
    290                 295                 300

Lys Gln Cys Asp Gly Gly Lys Cys Leu Leu Gln Leu Val Lys Thr Ser
305                 310                 315                 320

Arg Ser Thr Leu Pro Pro Leu Ile Asn Ala Met Glu Ala Tyr Thr Val
                325                 330                 335

Leu Asp Phe Pro Gln Ile Glu Thr Asn Val Asp Glu Val Ile Ala Ile
            340                 345                 350

Lys Asn Ile Gln Ser Thr Tyr Gly Leu Ser Lys Thr Thr Trp Gln Gly
        355                 360                 365

Asp Pro Cys Val Pro Lys Lys Phe Leu Trp Asp Gly Leu Asn Cys Asn
    370                 375                 380

Asn Ser Asp Asp Ser Thr Pro Pro Ile Ile Thr Ser Phe Gly Leu Thr
385                 390                 395                 400

Gly Ile Ile Val Leu Thr Ile Gln Asn Leu Ala Asn Leu Gln Glu Leu
                405                 410                 415

Asp Leu Ser Asn Asn Asn Leu Ser Gly Gly Val Pro Glu Phe Leu Ala
            420                 425                 430

Asp Met Lys Ser Leu Leu Val Ile Asn Leu Ser Gly Asn Asn Leu Ser
        435                 440                 445

Gly Val Val Pro Gln Lys Leu Ile Glu Lys Lys Met Leu Lys Leu Asn
    450                 455                 460

Ile Glu Gly Asn Pro Lys Leu Asn Cys Thr Val Glu Ser Cys Val Asn
465                 470                 475                 480

Lys Asp Glu Glu Gly Gly Arg Gln Ile Lys Ser Met Thr Ile Pro Ile
                485                 490                 495

Val Ala Ser Ile Gly Ser Val Val Ala Phe Thr Val Ala Leu Met Ile
            500                 505                 510

Phe Cys Val Val Arg Lys Asn Asn Pro Ser Asn Asp Glu Ala Pro Thr
        515                 520                 525

Ser Cys Met Leu Pro Ala Asp Ser Arg Ser Ser Glu Pro Thr Ile Val
```

```
    530                 535                 540

Thr Lys Asn Lys Lys Phe Thr Tyr Ala Glu Val Leu Thr Met Thr Asn
545                 550                 555                 560

Asn Phe Gln Lys Ile Leu Gly Lys Gly Gly Phe Gly Ile Val Tyr Tyr
                565                 570                 575

Gly Ser Val Asn Gly Thr Glu Gln Val Ala Val Lys Met Leu Ser His
            580                 585                 590

Ser Ser Ala Gln Gly Tyr Lys Gln Phe Lys Ala Glu Val Glu Leu Leu
        595                 600                 605

Leu Arg Val His His Lys Asn Leu Val Gly Leu Val Gly Tyr Cys Glu
    610                 615                 620

Glu Gly Asp Lys Leu Ala Leu Ile Tyr Glu Tyr Met Ala Asn Gly Asp
625                 630                 635                 640

Leu Asp Glu His Met Ser Gly Lys Arg Gly Gly Ser Ile Leu Asn Trp
                645                 650                 655

Gly Thr Arg Leu Lys Ile Ala Leu Glu Ala Ala Gln Gly Leu Glu Tyr
            660                 665                 670

Leu His Asn Gly Cys Lys Pro Leu Met Val His Arg Asp Val Lys Thr
        675                 680                 685

Thr Asn Ile Leu Leu Asn Glu His Phe Asp Thr Lys Leu Ala Asp Phe
    690                 695                 700

Gly Leu Ser Arg Ser Phe Pro Ile Glu Gly Glu Thr His Val Ser Thr
705                 710                 715                 720

Val Val Ala Gly Thr Ile Gly Tyr Leu Asp Pro Asp Asp Val Tyr Ser
                725                 730                 735

Phe Gly Val Val Leu Leu Val Met Ile Thr Asn Gln Pro Val Ile Asp
            740                 745                 750

Gln Asn Arg Glu Lys Arg His Ile Ala Glu Trp Val Gly Gly Met Leu
        755                 760                 765

Thr Lys Gly Asp Ile Lys Ser Ile Thr Asp Pro Asn Leu Leu Gly Asp
    770                 775                 780

Tyr Asn Ser Gly Ser Val Trp Lys Ala Val Glu Leu Ala Met Ser Cys
785                 790                 795                 800

Met Asn Pro Ser Ser Met Thr Arg Pro Thr Met Ser Gln Val Val Phe
                805                 810                 815

Glu Leu Lys Glu Cys Leu Ala Ser Glu Ser Ser Arg Glu Val Ser Met
            820                 825                 830

Thr Phe Gly Thr Glu Val Ala Pro Met Ala Arg
        835                 840


<210> SEQ ID NO 14
<211> LENGTH: 2658
<212> TYPE: DNA
<213> ORGANISM: Arabidopsis thaliana

<400> SEQUENCE: 14

atgaaaacac atcctcaagc aattctctta tgtgtgttat tcttcatcac gtttggtctt      60

ttacatgtcg ttgaagctgg aaatcaagaa ggattcatca gtttagattg tgggttatcc     120

cccaatgaac ctccttacgt cgatgctgca accgacttaa catacacaac ggacaatgat     180

ttcgtgcaga gcggtaaaac tggtacaatc gataaggaat tggagtcaac ctacaacaaa     240

ccaattttac agcttaggta cttccccgaa ggagtccgaa actgttatac cttgaacgtc     300

acgctcggca caaactacct gatcagagcc agtttcgtgt atggtaacta cgatggtctt     360

aataaagaac tcgagtttga cctttacctt ggtcctaatc tatgggcaaa cgtgaacaca     420
```

```
gctgtatatt taatgaacgg agtgaccaca gaagaaatca tccacagtac caaatctaag    480
gtactccagg tttgtcttat taagacaggc gagagtatac ctattattaa tagcttagag    540
ctgcgaccac ttataaacga tacttacaat actcaaagtg gctcgctgaa atacttattt    600
cggaattatt tcagcacttc aaggagaata atacggtacc cgaatgatgt caacgatcgt    660
cattggtatc cgttctttga tgaggatgcg tggacagaat tgactacaaa tctcaatgtt    720
aacagttcaa atggttatga tccaccaaaa tttgtaatgg cttcagcctc aacacccata    780
agtaaaaatg cgcccttcaa cttcacctgg tcattgattc cttctacggc caaattttat    840
agttacatgc acttcgccga tattcagact ctacaggcca atgaaacccg agaattcgac    900
atgatgttga atggaaacct tgccttggaa cgtgccctcg aggttttcac cgtgatcgat    960
ttccccgaat tggaaacaaa tcaagatgat gttattgcta tcaagaatat ccaaaatact   1020
tatggagtga gtaaaactag ctggcaagga gatccatgtg ttcctaaacg gtttatgtgg   1080
gatggcttaa actgcaacaa ctcgtatatt tccacaccac ctacaataac ttttttaaac   1140
ctatcatcaa gtcatttaac ggggatcatt gcatctgcca ttcaaaacct aacccacctg   1200
caaaatttgg acttgtcaaa taacaatttg acaggaggag tacccgagtt tcttgctggc   1260
ttaaaatcac tcttagtcat aaacttaagt gggaataatc ttagtggttc tgttcctcaa   1320
acccttctcc agaagaaagg acttaagtta aatcttgaag gaaatattta tcttaattgt   1380
ccggatggat catgtgtaag caaagacgga aatggaggtg ccaagaaaaa gaatgttgta   1440
gtattggttg tggtatcaat tgcacttgta gtagttcttg gatctgcatt agctcttttt   1500
ttggtgttta gaaaaagaaa aacaccacgc aatgaagttt ctagaacatc tagatcatta   1560
gacccgacaa taacgacgaa aaacagaaga tttacttatt cggaagttgt aaagatgaca   1620
aataattttg agaaaatcct tggtaaagga gggtttggaa tggtctatca tggaactgtg   1680
aatgatgctg aacaagtagc cgttaaaatg ttatcaccct catcatctca agggtataaa   1740
gaattcaaag cagaggtaga actccttctc agagttcacc ataaaaattt ggttggcctc   1800
gttggatatt gtgatgaagg agaaaattta tctctcatct acgagtacat ggctaaagga   1860
gatcttaaag aacatatgtt aggaaaccaa ggtgtatcta ttttggactg gaaaactaga   1920
ctaaagatag tggccgagtc cgcgcaaggg ctggaatact tgcataatgg atgcaaacca   1980
ccaatggtac atagagatgt caaaaccaca aatatattgt tggatgaaca ttttcaggcc   2040
aagcttgctg atttcggtct ttcgagatct tttcctcttg aaggagaaac ccgtgtggac   2100
acagttgttg ctggaactcc tgggtacctt gatccagaat attatcgaac aaattggttg   2160
aacgagaaaa gtgatgttta tagctttgga atcgtactat tagagatcat cacaaaccaa   2220
catgtgatca accaaagtcg tgaaaaacca catatagctg aatgggttgg ggtgatgctt   2280
acaaaaggag acatcaaaag cattatagat ccaaaattta gtggagatta tgatgctggt   2340
tctgtctgga gagcagttga actagcaatg tcgtgtgtaa atccttcttc aactggaaga   2400
ccaaccatgt ctcaagttgt aatcgaatta aatgaatgtt tggcatcaga aaactcaagg   2460
agaggaatga gtcaaaacat ggagtcaaag ggatctatcc aatatacaga agtcagcacg   2520
aactttggta ctgaatatac ccctgaagct cgctaggctg catgagccat ctatcttttg   2580
ttttatttgt gtgtgttttt tttaataaat aaattgaatg tttgtaatga gtttttgtaa   2640
ttaataaatg tgattttt                                                 2658
```

<210> SEQ ID NO 15
<211> LENGTH: 851

```
<212> TYPE: PRT
<213> ORGANISM: Arabidopsis thaliana

<400> SEQUENCE: 15

Met Lys Thr His Pro Gln Ala Ile Leu Leu Cys Val Leu Phe Phe Ile
1               5                   10                  15

Thr Phe Gly Leu Leu His Val Val Glu Ala Gly Asn Gln Glu Gly Phe
            20                  25                  30

Ile Ser Leu Asp Cys Gly Leu Ser Pro Asn Glu Pro Pro Tyr Val Asp
        35                  40                  45

Ala Ala Thr Asp Leu Thr Tyr Thr Thr Asp Asn Asp Phe Val Gln Ser
    50                  55                  60

Gly Lys Thr Gly Thr Ile Asp Lys Glu Leu Glu Ser Thr Tyr Asn Lys
65                  70                  75                  80

Pro Ile Leu Gln Leu Arg Tyr Phe Pro Glu Gly Val Arg Asn Cys Tyr
                85                  90                  95

Thr Leu Asn Val Thr Leu Gly Thr Asn Tyr Leu Ile Arg Ala Ser Phe
            100                 105                 110

Val Tyr Gly Asn Tyr Asp Gly Leu Asn Lys Glu Leu Glu Phe Asp Leu
        115                 120                 125

Tyr Leu Gly Pro Asn Leu Trp Ala Asn Val Asn Thr Ala Val Tyr Leu
    130                 135                 140

Met Asn Gly Val Thr Thr Glu Glu Ile Ile His Ser Thr Lys Ser Lys
145                 150                 155                 160

Val Leu Gln Val Cys Leu Ile Lys Thr Gly Glu Ser Ile Pro Ile Ile
                165                 170                 175

Asn Ser Leu Glu Leu Arg Pro Leu Ile Asn Asp Thr Tyr Asn Thr Gln
            180                 185                 190

Ser Gly Ser Leu Lys Tyr Leu Phe Arg Asn Tyr Phe Ser Thr Ser Arg
        195                 200                 205

Arg Ile Ile Arg Tyr Pro Asn Asp Val Asn Asp Arg His Trp Tyr Pro
    210                 215                 220

Phe Phe Asp Glu Asp Ala Trp Thr Glu Leu Thr Thr Asn Leu Asn Val
225                 230                 235                 240

Asn Ser Ser Asn Gly Tyr Asp Pro Pro Lys Phe Val Met Ala Ser Ala
                245                 250                 255

Ser Thr Pro Ile Ser Lys Asn Ala Pro Phe Asn Phe Thr Trp Ser Leu
            260                 265                 270

Ile Pro Ser Thr Ala Lys Phe Tyr Ser Tyr Met His Phe Ala Asp Ile
        275                 280                 285

Gln Thr Leu Gln Ala Asn Glu Thr Arg Glu Phe Asp Met Met Leu Asn
    290                 295                 300

Gly Asn Leu Ala Leu Glu Arg Ala Leu Glu Val Phe Thr Val Ile Asp
305                 310                 315                 320

Phe Pro Glu Leu Glu Thr Asn Gln Asp Asp Val Ile Ala Ile Lys Asn
                325                 330                 335

Ile Gln Asn Thr Tyr Gly Val Ser Lys Thr Ser Trp Gln Gly Asp Pro
            340                 345                 350

Cys Val Pro Lys Arg Phe Met Trp Asp Gly Leu Asn Cys Asn Asn Ser
        355                 360                 365

Tyr Ile Ser Thr Pro Pro Thr Ile Thr Phe Leu Asn Leu Ser Ser Ser
    370                 375                 380

His Leu Thr Gly Ile Ile Ala Ser Ala Ile Gln Asn Leu Thr His Leu
385                 390                 395                 400
```

```
Gln Asn Leu Asp Leu Ser Asn Asn Asn Leu Thr Gly Gly Val Pro Glu
                405                 410                 415

Phe Leu Ala Gly Leu Lys Ser Leu Leu Val Ile Asn Leu Ser Gly Asn
            420                 425                 430

Asn Leu Ser Gly Ser Val Pro Gln Thr Leu Leu Gln Lys Lys Gly Leu
        435                 440                 445

Lys Leu Asn Leu Glu Gly Asn Ile Tyr Leu Asn Cys Pro Asp Gly Ser
    450                 455                 460

Cys Val Ser Lys Asp Gly Asn Gly Gly Ala Lys Lys Lys Asn Val Val
465                 470                 475                 480

Val Leu Val Val Val Ser Ile Ala Leu Val Val Val Leu Gly Ser Ala
                485                 490                 495

Leu Ala Leu Phe Leu Val Phe Arg Lys Arg Lys Thr Pro Arg Asn Glu
            500                 505                 510

Val Ser Arg Thr Ser Arg Ser Leu Asp Pro Thr Ile Thr Thr Lys Asn
        515                 520                 525

Arg Arg Phe Thr Tyr Ser Glu Val Val Lys Met Thr Asn Asn Phe Glu
    530                 535                 540

Lys Ile Leu Gly Lys Gly Gly Phe Gly Met Val Tyr His Gly Thr Val
545                 550                 555                 560

Asn Asp Ala Glu Gln Val Ala Val Lys Met Leu Ser Pro Ser Ser Ser
                565                 570                 575

Gln Gly Tyr Lys Glu Phe Lys Ala Glu Val Glu Leu Leu Leu Arg Val
            580                 585                 590

His His Lys Asn Leu Val Gly Leu Val Gly Tyr Cys Asp Glu Gly Glu
        595                 600                 605

Asn Leu Ser Leu Ile Tyr Glu Tyr Met Ala Lys Gly Asp Leu Lys Glu
    610                 615                 620

His Met Leu Gly Asn Gln Gly Val Ser Ile Leu Asp Trp Lys Thr Arg
625                 630                 635                 640

Leu Lys Ile Val Ala Glu Ser Ala Gln Gly Leu Glu Tyr Leu His Asn
                645                 650                 655

Gly Cys Lys Pro Pro Met Val His Arg Asp Val Lys Thr Thr Asn Ile
            660                 665                 670

Leu Leu Asp Glu His Phe Gln Ala Lys Leu Ala Asp Phe Gly Leu Ser
        675                 680                 685

Arg Ser Phe Pro Leu Glu Gly Glu Thr Arg Val Asp Thr Val Val Ala
    690                 695                 700

Gly Thr Pro Gly Tyr Leu Asp Pro Glu Tyr Tyr Arg Thr Asn Trp Leu
705                 710                 715                 720

Asn Glu Lys Ser Asp Val Tyr Ser Phe Gly Ile Val Leu Leu Glu Ile
                725                 730                 735

Ile Thr Asn Gln His Val Ile Asn Gln Ser Arg Glu Lys Pro His Ile
            740                 745                 750

Ala Glu Trp Val Gly Val Met Leu Thr Lys Gly Asp Ile Lys Ser Ile
        755                 760                 765

Ile Asp Pro Lys Phe Ser Gly Asp Tyr Asp Ala Gly Ser Val Trp Arg
    770                 775                 780

Ala Val Glu Leu Ala Met Ser Cys Val Asn Pro Ser Ser Thr Gly Arg
785                 790                 795                 800

Pro Thr Met Ser Gln Val Val Ile Glu Leu Asn Glu Cys Leu Ala Ser
                805                 810                 815

Glu Asn Ser Arg Arg Gly Met Ser Gln Asn Met Glu Ser Lys Gly Ser
            820                 825                 830
```

```
Ile Gln Tyr Thr Glu Val Ser Thr Asn Phe Gly Thr Glu Tyr Thr Pro
        835                 840                 845

Glu Ala Arg
    850


<210> SEQ ID NO 16
<211> LENGTH: 2704
<212> TYPE: DNA
<213> ORGANISM: Arabidopsis thaliana

<400> SEQUENCE: 16

atggagtacc atcctcaagc aattaggtta tgtgcgttga tcttcatctc tttctatgct      60

cttttacacc tcgttgaagc acaagaccaa aaaggattca ttagtttgga ttgcgggtca     120

ttgccaaatg agcctcctta caacgatcct tcaaccggat taacatactc gacggacgat     180

ggtttcgtgc agagtggcaa aactggaaga atccagaaag cgttcgagtc gatcttcagt     240

aaaccgtctt tgaagcttag atacttcccg gacggattcc gaaactgcta taccttgaat     300

gtcacgcaag acacaaacta tctgatcaaa gctgtatttg tgtatggtaa ctacgatggt     360

cttaacaatc ccccgagttt cgatctttac cttggtccga atctatgggt aacggttgat     420

atgaatggac ggaccaatgg tactatccag gagattatcc acaagaccat atctaagtct     480

ctccaggtct gtcttgttaa gacaggaaca agctcaccta tgattaatac gttagagcta     540

cgaccactta aaaacaatac ttacaatact cagagtggct ctctgaagta tttcttccga     600

tattatttca gcggttcagg ccaaaacata cggtaccctg atgatgtcaa tgatcgtaaa     660

tggtatccat tctttgatgc aaaagagtgg acagagttaa caaccaatct gaatataaac     720

agttctaatg gttatgcacc accagaagtt gtgatggcgt cagcctcaac gcctataagt     780

acttttggaa catggaactt ctcatggtta ttgccatctt ccacaaccca attttatgtg     840

tacatgcatt ttgccgagat tcaaactcta cggtccctcg atacccgaga attcaaagtg     900

acgttgaatg gaaaacttgc ttatgaacgc tacagcccta aaacgttagc caccgaaacc     960

attttctatt cgacaccaca acaatgtgaa gatgggacat gcctcttgga gttgacgaaa    1020

acacctaagt ctactcttcc tcctctcatg aacgctcttg aggttttcac cgtgatcgat    1080

tttccacaga tggaaacaaa tccagatgat gttgctgcta tcaagagtat ccaaagcact    1140

tatggattaa gtaaaatcag ctggcaagga gatccatgcg ttcctaaaca gtttttgtgg    1200

gagggtttaa actgcaataa tctagataac tccacgccgc ctattgtcac ttccttaaac    1260

ttatcgtcaa gtcatttaac ggggatcatc gcgcaaggca ttcagaatct gacacaccta    1320

caagaactag acttgtcaaa taacaatttg acgggaggaa tacccgaatt tcttgctgac    1380

ataaaatcac tcttagtaat aaatttaagt gggaacaatt ttaatggctc tattcctcaa    1440

atccttttac agaagaaagg actaaagcta attcttgaag gaaacgccaa tctgatttgt    1500

ccggatggat tatgtgtaaa caaagctggc aatggtggtg ccaagaaaat gaatgttgta    1560

ataccgattg ttgcatcagt tgcgtttgtg gttgttcttg gatctgcatt ggcgttcttt    1620

tttattttca aaaagaaaaa gacatcaaac agtcaagagt cggcaataat gactaagaac    1680

agaagattta catattcgga ggttgtaaca atgacaaata actttgaaag agttcttggt    1740

aaaggaggat ttggaatggt ttatcatgga actgtaaata atactgaaca agtagccgtt    1800

aaaatgcttt cacactcatc ttctcaagga tataaagaat tcaaagcaga ggtggaactt    1860

cttctcagag ttcaccacaa aaatttggtt ggcctcgttg gatattgtga tgaaggagaa    1920

aacttggctc ttatctacga gtacatggct aacggagact tgagagaaca tatgtcagga    1980
```

```
aagcgaggtg gatctattct aaattgggaa actagactaa aaatagttgt cgagtctgcc   2040

caaggtttgg aatacttgca taatggatgc aaaccaccaa tggttcatag ggatgttaaa   2100

accacaaata tattgttgaa tgaacacctc catgctaagc tagctgattt tgggctttcg   2160

agatcttttc caattgaagg agaaactcat gtgtcaacag ttgttgctgg aactcctgga   2220

taccttgatc cagaatatta ccgaacaaat tggttgaacg agaaaagtga tgtttatagc   2280

tttggaattg tactattaga gatcatcaca aaccaacttg tgatcaatca aagtcgtgaa   2340

aaaccacata tagcagaatg ggtggggtta atgcttacaa aaggagacat tcaaaacatt   2400

atggatccaa aactttatgg tgattatgac tctggttctg tctggagagc agttgaacta   2460

gcaatgtcat gtctaaatcc ttcttcagct agaagaccaa caatgtctca agttgttatc   2520

gaattaaacg aatgtttgtc atatgaaaac gcaagaggag gaacgagtca aaacatgaac   2580

tcagagagtt caatagaagt cagcatgaac tttgatattg gagctacccc tgatgctcgt   2640

tagactgcaa gagtcatttt atctttgttt tcttgagtgg atttttgtta ttttcaaagg   2700

aaaa                                                                2704
```

<210> SEQ ID NO 17
<211> LENGTH: 880
<212> TYPE: PRT
<213> ORGANISM: Arabidopsis thaliana

<400> SEQUENCE: 17

```
Met Glu Tyr His Pro Gln Ala Ile Arg Leu Cys Ala Leu Ile Phe Ile
1               5                   10                  15

Ser Phe Tyr Ala Leu Leu His Leu Val Glu Ala Gln Asp Gln Lys Gly
            20                  25                  30

Phe Ile Ser Leu Asp Cys Gly Ser Leu Pro Asn Glu Pro Pro Tyr Asn
        35                  40                  45

Asp Pro Ser Thr Gly Leu Thr Tyr Ser Thr Asp Asp Gly Phe Val Gln
    50                  55                  60

Ser Gly Lys Thr Gly Arg Ile Gln Lys Ala Phe Glu Ser Ile Phe Ser
65                  70                  75                  80

Lys Pro Ser Leu Lys Leu Arg Tyr Phe Pro Asp Gly Phe Arg Asn Cys
                85                  90                  95

Tyr Thr Leu Asn Val Thr Gln Asp Thr Asn Tyr Leu Ile Lys Ala Val
            100                 105                 110

Phe Val Tyr Gly Asn Tyr Asp Gly Leu Asn Asn Pro Pro Ser Phe Asp
        115                 120                 125

Leu Tyr Leu Gly Pro Asn Leu Trp Val Thr Val Asp Met Asn Gly Arg
    130                 135                 140

Thr Asn Gly Thr Ile Gln Glu Ile Ile His Lys Thr Ile Ser Lys Ser
145                 150                 155                 160

Leu Gln Val Cys Leu Val Lys Thr Gly Thr Ser Ser Pro Met Ile Asn
                165                 170                 175

Thr Leu Glu Leu Arg Pro Leu Lys Asn Asn Thr Tyr Asn Thr Gln Ser
            180                 185                 190

Gly Ser Leu Lys Tyr Phe Phe Arg Tyr Tyr Phe Ser Gly Ser Gly Gln
        195                 200                 205

Asn Ile Arg Tyr Pro Asp Asp Val Asn Asp Arg Lys Trp Tyr Pro Phe
    210                 215                 220

Phe Asp Ala Lys Glu Trp Thr Glu Leu Thr Thr Asn Leu Asn Ile Asn
225                 230                 235                 240
```

```
Ser Ser Asn Gly Tyr Ala Pro Pro Glu Val Val Met Ala Ser Ala Ser
                245                 250                 255

Thr Pro Ile Ser Thr Phe Gly Thr Trp Asn Phe Ser Trp Leu Leu Pro
            260                 265                 270

Ser Ser Thr Thr Gln Phe Tyr Val Tyr Met His Phe Ala Glu Ile Gln
        275                 280                 285

Thr Leu Arg Ser Leu Asp Thr Arg Glu Phe Lys Val Thr Leu Asn Gly
    290                 295                 300

Lys Leu Ala Tyr Glu Arg Tyr Ser Pro Lys Thr Leu Ala Thr Glu Thr
305                 310                 315                 320

Ile Phe Tyr Ser Thr Pro Gln Gln Cys Glu Asp Gly Thr Cys Leu Leu
                325                 330                 335

Glu Leu Thr Lys Thr Pro Lys Ser Thr Leu Pro Pro Leu Met Asn Ala
            340                 345                 350

Leu Glu Val Phe Thr Val Ile Asp Phe Pro Gln Met Glu Thr Asn Pro
        355                 360                 365

Asp Asp Val Ala Ala Ile Lys Ser Ile Gln Ser Thr Tyr Gly Leu Ser
    370                 375                 380

Lys Ile Ser Trp Gln Gly Asp Pro Cys Val Pro Lys Gln Phe Leu Trp
385                 390                 395                 400

Glu Gly Leu Asn Cys Asn Asn Leu Asp Asn Ser Thr Pro Pro Ile Val
                405                 410                 415

Thr Ser Leu Asn Leu Ser Ser Ser His Leu Thr Gly Ile Ile Ala Gln
            420                 425                 430

Gly Ile Gln Asn Leu Thr His Leu Gln Glu Leu Asp Leu Ser Asn Asn
        435                 440                 445

Asn Leu Thr Gly Gly Ile Pro Glu Phe Leu Ala Asp Ile Lys Ser Leu
    450                 455                 460

Leu Val Ile Asn Leu Ser Gly Asn Asn Phe Asn Gly Ser Ile Pro Gln
465                 470                 475                 480

Ile Leu Leu Gln Lys Lys Gly Leu Lys Leu Ile Leu Glu Gly Asn Ala
                485                 490                 495

Asn Leu Ile Cys Pro Asp Gly Leu Cys Val Asn Lys Ala Gly Asn Gly
            500                 505                 510

Gly Ala Lys Lys Met Asn Val Val Ile Pro Ile Val Ala Ser Val Ala
        515                 520                 525

Phe Val Val Val Leu Gly Ser Ala Leu Ala Phe Phe Phe Ile Phe Lys
    530                 535                 540

Lys Lys Lys Thr Ser Asn Ser Gln Glu Ser Ala Ile Met Thr Lys Asn
545                 550                 555                 560

Arg Arg Phe Thr Tyr Ser Glu Val Val Thr Met Thr Asn Asn Phe Glu
                565                 570                 575

Arg Val Leu Gly Lys Gly Gly Phe Gly Met Val Tyr His Gly Thr Val
            580                 585                 590

Asn Asn Thr Glu Gln Val Ala Val Lys Met Leu Ser His Ser Ser Ser
        595                 600                 605

Gln Gly Tyr Lys Glu Phe Lys Ala Glu Val Glu Leu Leu Leu Arg Val
    610                 615                 620

His His Lys Asn Leu Val Gly Leu Val Gly Tyr Cys Asp Glu Gly Glu
625                 630                 635                 640

Asn Leu Ala Leu Ile Tyr Glu Tyr Met Ala Asn Gly Asp Leu Arg Glu
                645                 650                 655

His Met Ser Gly Lys Arg Gly Gly Ser Ile Leu Asn Trp Glu Thr Arg
            660                 665                 670
```

```
Leu Lys Ile Val Val Glu Ser Ala Gln Gly Leu Glu Tyr Leu His Asn
        675                 680                 685

Gly Cys Lys Pro Pro Met Val His Arg Asp Val Lys Thr Thr Asn Ile
    690                 695                 700

Leu Leu Asn Glu His Leu His Ala Lys Leu Ala Asp Phe Gly Leu Ser
705                 710                 715                 720

Arg Ser Phe Pro Ile Glu Gly Glu Thr His Val Ser Thr Val Val Ala
                725                 730                 735

Gly Thr Pro Gly Tyr Leu Asp Pro Glu Tyr Tyr Arg Thr Asn Trp Leu
            740                 745                 750

Asn Glu Lys Ser Asp Val Tyr Ser Phe Gly Ile Val Leu Leu Glu Ile
        755                 760                 765

Ile Thr Asn Gln Leu Val Ile Asn Gln Ser Arg Glu Lys Pro His Ile
    770                 775                 780

Ala Glu Trp Val Gly Leu Met Leu Thr Lys Gly Asp Ile Gln Asn Ile
785                 790                 795                 800

Met Asp Pro Lys Leu Tyr Gly Asp Tyr Asp Ser Gly Ser Val Trp Arg
                805                 810                 815

Ala Val Glu Leu Ala Met Ser Cys Leu Asn Pro Ser Ser Ala Arg Arg
            820                 825                 830

Pro Thr Met Ser Gln Val Val Ile Glu Leu Asn Glu Cys Leu Ser Tyr
        835                 840                 845

Glu Asn Ala Arg Gly Gly Thr Ser Gln Asn Met Asn Ser Glu Ser Ser
    850                 855                 860

Ile Glu Val Ser Met Asn Phe Asp Ile Gly Ala Thr Pro Asp Ala Arg
865                 870                 875                 880


<210> SEQ ID NO 18
<211> LENGTH: 2667
<212> TYPE: DNA
<213> ORGANISM: Arabidopsis thaliana

<400> SEQUENCE: 18

atggagaagt attttcatgg agttttatgt gtgttcatca tcacagttgc ttttatacat     60

gttgttcagg ctcaagatcc aaacggattc atcactttgg attgtggtct gttacctgat    120

ggatctccat ataccaatcc atctactgga ttaacattca cttcggattc tagtttcatc    180

gagagtggaa agaatggccg agtcagtaag gactctgagc gaaacttcga aaaagctttt    240

gtaactctaa gatactttcc agatggagag cggaactgtt ataacctgaa tgtcacacaa    300

ggaacaaatt acttgattag agcagctttc ttatatggaa attacgatgg tcttaatact    360

gtcccaaact ttgatctatt tattggccct aataaggtga caacagtgaa ttttaatgca    420

accggaggtg gtgtgttcgt ggagataatt cacatgtcaa ggtcaacccc tttggatatt    480

tgtcttgtta agacaggaac aactacaccg atgatatcaa ccttggagct acgacctttg    540

agaagtgata cttacattag tgccattggg agctccttgc tcctctattt tagaggttat    600

cttaatgatt caggtgtcgt tttacggtac cccgatgatg tcaacgaccg tagatggttc    660

ccattctcat ataaggagtg gaaaattgta accacaactc tcaatgtaaa cacttcaaat    720

ggttttgatc taccacaagg tgcaatggca tcggctgcaa cccgtgttaa tgataatggg    780

acatgggaat ttccatggag cttagaggat tctaccacac ggtttcacat ttaccttcac    840

ttcgcagagc ttcaaacttt gttagccaac gagactagag aattcaatgt tttgctgaat    900

ggaaaagttt attatggacc ttatagtcct aaaatgttaa gtatagatac tatgagcccc    960
```

```
caacccgatt cgacattgac atgtaaagga ggaagttgcc tcttgcagct agtgaagaca   1020

acaaagtcaa ctcttcctcc tctcatcaat gctattgaac tttttactgt tgttgagttt   1080

cctcaatcag aaacaaacca agatgaagtg attgctatca agaagatcca acttacttat   1140

ggattgagta gaattaactg gcaaggagat ccatgtgtcc ccgagcagtt tttgtgggct   1200

ggtttgaagt gcagcaatat taatagttcc actccaccaa caatcacttt cttaaacttg   1260

tcttcaagtg gactaaccgg gatcatttca ccttccatcc agaatttgac ccatttacaa   1320

gagttggatt tgtcaaataa cgacttgacc ggggatgtgc ctgagtttct agctgacata   1380

aaatcgctct tgatcataaa cttaagtgga aacaatttta gcggtcaact tcctcaaaag   1440

cttatagata agaaaagact gaagctgaat gttgaaggaa accctaagct tctttgcaca   1500

aaaggaccat gtggaaataa acctggagaa ggtggacatc ccaaaaagag tataattgta   1560

ccggttgtct catcagttgc tttaatagct attcttatag ctgcattggt tttgtttttg   1620

gttcttagaa agaaaaatcc atcaaggagt aaagaaaatg gtagaacttc aagatcatcc   1680

gagccaccaa gaataacaaa aaagaaaaag tttacttacg tggaagttac tgaaatgaca   1740

aataacttta gaagtgttct tgggaaagga gggttcggta tggtttatca tggatatgta   1800

aatggtagag agcaagttgc tgttaaagta ctctcacacg cttcaaaaca tggccataaa   1860

caattcaaag cagaggttga acttcttttg agagttcatc acaagaattt ggtaagccta   1920

gttggatact gcgaaaaagg gaaggaattg gctcttgtct acgaatacat ggctaatgga   1980

gacttaaaag agtttttctc agggaagcgt ggtgatgatg ttttaaggtg ggaaactaga   2040

ttacaaatag cagtggaggc cgcacaaggt ttggagtact tgcataaagg atgtagacca   2100

ccaattgttc atagagatgt caaaaccgca aacatattat tggatgaaca cttccaagcc   2160

aaacttgctg actttgggct ttcgagatca tttctaaacg aaggagaaag tcatgtctcg   2220

acagttgttg caggaactat tggttacctt gatccagaat attacagaac aaattggttg   2280

acagagaaga gtgatgtgta tagttttggg gtcgttttat tggagatcat aacaaatcag   2340

cgcgtgattg agcggactcg agaaaagcca cacatagcag aatgggtgaa tttaatgatt   2400

accaaaggag atattagaaa aattgtagat ccaaatctca agggagatta ccattctgat   2460

tctgtttgga agtttgtgga gctagcaatg acttgtgtaa atgattcttc agcgacaaga   2520

ccgaccatga ctcaagttgt taccgaacta accgaatgtg taactttaga aaactcaagg   2580

ggagggaaaa gtcagaacat gggttcaacg agttcaagcg aagtgaccat gacctttgat   2640

accgaagtga accctgtggc tcgctag                                       2667
```

<210> SEQ ID NO 19
<211> LENGTH: 888
<212> TYPE: PRT
<213> ORGANISM: Arabidopsis thaliana

<400> SEQUENCE: 19

```
Met Glu Lys Tyr Phe His Gly Val Leu Cys Val Phe Ile Ile Thr Val
1               5                   10                  15

Ala Phe Ile His Val Val Gln Ala Gln Asp Pro Asn Gly Phe Ile Thr
            20                  25                  30

Leu Asp Cys Gly Leu Leu Pro Asp Gly Ser Pro Tyr Thr Asn Pro Ser
        35                  40                  45

Thr Gly Leu Thr Phe Thr Ser Asp Ser Ser Phe Ile Glu Ser Gly Lys
    50                  55                  60

Asn Gly Arg Val Ser Lys Asp Ser Glu Arg Asn Phe Glu Lys Ala Phe
65                  70                  75                  80
```

```
Val Thr Leu Arg Tyr Phe Pro Asp Gly Glu Arg Asn Cys Tyr Asn Leu
                85                  90                  95

Asn Val Thr Gln Gly Thr Asn Tyr Leu Ile Arg Ala Ala Phe Leu Tyr
            100                 105                 110

Gly Asn Tyr Asp Gly Leu Asn Thr Val Pro Asn Phe Asp Leu Phe Ile
        115                 120                 125

Gly Pro Asn Lys Val Thr Thr Val Asn Phe Asn Ala Thr Gly Gly Gly
    130                 135                 140

Val Phe Val Glu Ile Ile His Met Ser Arg Ser Thr Pro Leu Asp Ile
145                 150                 155                 160

Cys Leu Val Lys Thr Gly Thr Thr Thr Pro Met Ile Ser Thr Leu Glu
                165                 170                 175

Leu Arg Pro Leu Arg Ser Asp Thr Tyr Ile Ser Ala Ile Gly Ser Ser
            180                 185                 190

Leu Leu Leu Tyr Phe Arg Gly Tyr Leu Asn Asp Ser Gly Val Val Leu
        195                 200                 205

Arg Tyr Pro Asp Asp Val Asn Asp Arg Arg Trp Phe Pro Phe Ser Tyr
    210                 215                 220

Lys Glu Trp Lys Ile Val Thr Thr Thr Leu Asn Val Asn Thr Ser Asn
225                 230                 235                 240

Gly Phe Asp Leu Pro Gln Gly Ala Met Ala Ser Ala Ala Thr Arg Val
                245                 250                 255

Asn Asp Asn Gly Thr Trp Glu Phe Pro Trp Ser Leu Glu Asp Ser Thr
            260                 265                 270

Thr Arg Phe His Ile Tyr Leu His Phe Ala Glu Leu Gln Thr Leu Leu
        275                 280                 285

Ala Asn Glu Thr Arg Glu Phe Asn Val Leu Leu Asn Gly Lys Val Tyr
    290                 295                 300

Tyr Gly Pro Tyr Ser Pro Lys Met Leu Ser Ile Asp Thr Met Ser Pro
305                 310                 315                 320

Gln Pro Asp Ser Thr Leu Thr Cys Lys Gly Gly Ser Cys Leu Leu Gln
                325                 330                 335

Leu Val Lys Thr Thr Lys Ser Thr Leu Pro Pro Leu Ile Asn Ala Ile
            340                 345                 350

Glu Leu Phe Thr Val Val Glu Phe Pro Gln Ser Glu Thr Asn Gln Asp
        355                 360                 365

Glu Val Ile Ala Ile Lys Lys Ile Gln Leu Thr Tyr Gly Leu Ser Arg
    370                 375                 380

Ile Asn Trp Gln Gly Asp Pro Cys Val Pro Glu Gln Phe Leu Trp Ala
385                 390                 395                 400

Gly Leu Lys Cys Ser Asn Ile Asn Ser Ser Thr Pro Pro Thr Ile Thr
                405                 410                 415

Phe Leu Asn Leu Ser Ser Ser Gly Leu Thr Gly Ile Ile Ser Pro Ser
            420                 425                 430

Ile Gln Asn Leu Thr His Leu Gln Glu Leu Asp Leu Ser Asn Asn Asp
        435                 440                 445

Leu Thr Gly Asp Val Pro Glu Phe Leu Ala Asp Ile Lys Ser Leu Leu
    450                 455                 460

Ile Ile Asn Leu Ser Gly Asn Asn Phe Ser Gly Gln Leu Pro Gln Lys
465                 470                 475                 480

Leu Ile Asp Lys Lys Arg Leu Lys Leu Asn Val Glu Gly Asn Pro Lys
                485                 490                 495

Leu Leu Cys Thr Lys Gly Pro Cys Gly Asn Lys Pro Gly Glu Gly Gly
```

```
            500                 505                 510

His Pro Lys Lys Ser Ile Ile Val Pro Val Val Ser Ser Val Ala Leu
        515                 520                 525

Ile Ala Ile Leu Ile Ala Ala Leu Val Leu Phe Leu Val Leu Arg Lys
    530                 535                 540

Lys Asn Pro Ser Arg Ser Lys Glu Asn Gly Arg Thr Ser Arg Ser Ser
545                 550                 555                 560

Glu Pro Pro Arg Ile Thr Lys Lys Lys Lys Phe Thr Tyr Val Glu Val
                565                 570                 575

Thr Glu Met Thr Asn Asn Phe Arg Ser Val Leu Gly Lys Gly Gly Phe
            580                 585                 590

Gly Met Val Tyr His Gly Tyr Val Asn Gly Arg Glu Gln Val Ala Val
        595                 600                 605

Lys Val Leu Ser His Ala Ser Lys His Gly His Lys Gln Phe Lys Ala
    610                 615                 620

Glu Val Glu Leu Leu Leu Arg Val His His Lys Asn Leu Val Ser Leu
625                 630                 635                 640

Val Gly Tyr Cys Glu Lys Gly Lys Glu Leu Ala Leu Val Tyr Glu Tyr
                645                 650                 655

Met Ala Asn Gly Asp Leu Lys Glu Phe Phe Ser Gly Lys Arg Gly Asp
            660                 665                 670

Asp Val Leu Arg Trp Glu Thr Arg Leu Gln Ile Ala Val Glu Ala Ala
        675                 680                 685

Gln Gly Leu Glu Tyr Leu His Lys Gly Cys Arg Pro Pro Ile Val His
    690                 695                 700

Arg Asp Val Lys Thr Ala Asn Ile Leu Leu Asp Glu His Phe Gln Ala
705                 710                 715                 720

Lys Leu Ala Asp Phe Gly Leu Ser Arg Ser Phe Leu Asn Glu Gly Glu
                725                 730                 735

Ser His Val Ser Thr Val Val Ala Gly Thr Ile Gly Tyr Leu Asp Pro
            740                 745                 750

Glu Tyr Tyr Arg Thr Asn Trp Leu Thr Glu Lys Ser Asp Val Tyr Ser
        755                 760                 765

Phe Gly Val Val Leu Leu Glu Ile Ile Thr Asn Gln Arg Val Ile Glu
    770                 775                 780

Arg Thr Arg Glu Lys Pro His Ile Ala Glu Trp Val Asn Leu Met Ile
785                 790                 795                 800

Thr Lys Gly Asp Ile Arg Lys Ile Val Asp Pro Asn Leu Lys Gly Asp
                805                 810                 815

Tyr His Ser Asp Ser Val Trp Lys Phe Val Glu Leu Ala Met Thr Cys
            820                 825                 830

Val Asn Asp Ser Ser Ala Thr Arg Pro Thr Met Thr Gln Val Val Thr
        835                 840                 845

Glu Leu Thr Glu Cys Val Thr Leu Glu Asn Ser Arg Gly Gly Lys Ser
    850                 855                 860

Gln Asn Met Gly Ser Thr Ser Ser Ser Glu Val Thr Met Thr Phe Asp
865                 870                 875                 880

Thr Glu Val Asn Pro Val Ala Arg
                885
```

<210> SEQ ID NO 20
<211> LENGTH: 820
<212> TYPE: DNA
<213> ORGANISM: Oryza sativa

<400> SEQUENCE: 20

```
tgcacaccta tccttcatct gatcctccca tgcatggtat atagtaccag aacgcatgaa     60
tgccccagaa agtgtgaaaa atcgctggaa ccatctgcca aaaactgaaa atcgccgatt    120
tacatatgag gagcttgaga agtatactga taacttcaaa cgcctcattg gacacggagg    180
ctttggacat gtttactatg gttgtctaga agaaaatatt gaggttgctg tcaagatacg    240
atctgaatca tcatcacacg ggcttgatga gtttttggct gaggttcaga gtttgacaaa    300
ggtgcatcac agaaatctgg tgtctttggt tggctactgt tgggagaatg atcatttagc    360
acttgtttac gagtacatgt ctggaggcaa tctttgtgac catctgagag gtaaaattgg    420
tgctgataaa tccttaaatt gggcaacacg tctacgtatt ctagttgatg ctggacaagg    480
cctggattat ctacataagg gttgtaacct gccaattatt catggagatg ttaagaccaa    540
taacattcta ttgggtcaaa atctaaaagc aaaaatagga gattttgggc tttccaaaac    600
ataccatagc gacacgcaga ctcacatatc agctacagca gctggatccg tgggatacat    660
cgatccagag tactacagca ctggaaggct cacggagagc agtgatgttt acagctttgg    720
tgttgttttg ctagaggtag ccacaggtga gtctcccata atacctggac atggtcacat    780
tgttcagcgt gtgaaacaga agattgtcac tggcaatatc                          820
```

<210> SEQ ID NO 21
<211> LENGTH: 824
<212> TYPE: DNA
<213> ORGANISM: Oryza sativa

<400> SEQUENCE: 21

```
ctttttttaa cattgtacca gaacagtttc tcacataaac atcttattgt tgtgttccac     60
acattgaagc aaactatata ttgcaaggaa ttaagcactc ctattttggt tctgtcgaac    120
catctttgtt tatgaatacc tgttgtataa attactgcgt ttgtcatatc attttacact    180
tatagcagag aattgacgtg gcaaagccag gcgcacgtac actttcttca tcttggtgaa    240
ggaccaaatt ttgacatgga agacgcggta tcacttgcta tgttttcgtg gtcgaccctt    300
tcctcatgag cgtcctccaa agctaggcct tccttaagtt gtgcaaccac agtggccatc    360
actggtcttt gagtagcaac atcagcagtg cacctcatgg cagtgtcaac aaccttccac    420
atagagctga cattgtaggc atcaagacgc gaatcggcaa ctgagctgat attgccagtg    480
acaatcttct gtttcacacg ctgaacaatg tgaccatgtc caggtattat tggagactca    540
cctgtggcta cctctagcaa aacaacacca aagctgtaaa catcactgct ctccgtgagc    600
cttccagtgc tgtagtactc tggatcgatg tatcccacgg atccagctgc tgtagctgat    660
atgtgagtct gcgtgtcgct atggtatgtt ttggaaagcc caaaatctcc tatttttgct    720
tttagatttt gacccaatag aatgttattg gtcttaacat ctccatgaat aattggcagg    780
ttacaaccct tatgtagata atccaggcct tgtccagcat caac                     824
```

<210> SEQ ID NO 22
<211> LENGTH: 807
<212> TYPE: DNA
<213> ORGANISM: Oryza sativa

<400> SEQUENCE: 22

```
ctttttttatt ttaaggtctt accacatatc aattgtaaca ttgtaccaga acagtttctc     60
acataaacat attattgttg tgttccacac attgaagcaa actatatatt gcaaggaatt    120
aagcactcct attttggttc tgtcgaacca tctttgttta tgaatacctg ttgtataaat    180
```

```
tactgcgttt gtcatatcat tttacactta tagcagagaa ttgacgtggc aaagccaggc    240

gcacgtacac tttcttcatc ttggtgaagg accaaatttt gacatggaag acgcggtatc    300

acttgctatg ttttcgtggt cgaccctttc ctcatgagcg tcctccaaag ctaggccttc    360

cttaagttgt gcaaccacag tggccatcac tggtctttga gtagcaacat cagcagtgca    420

cctcatggca gtgtcaacaa ccttccacat agagctgaca ttgtaggcat caagacgcga    480

atcggcaact gagctgatat tgccagtgac aatcttctgt ttcacacgct gaacaatgtg    540

accatgtcca ggtattattg gagactcacc tgtggctacc tctagcaaaa caacaccaaa    600

gctgtaaaca tcactgctct ccgtgagcct tccagtgctg tagtactctg gatcgatgta    660

tcccacggat ccagctgctg tagctgatat gtgagtctgc gtgtcgctat ggtatgtttt    720

ggaaagccca aaatctccta tttttgcttt tagattttga cccaatagaa tgttattggt    780

cttaacatct ccatgaataa ttggcag                                          807
```

```
<210> SEQ ID NO 23
<211> LENGTH: 2721
<212> TYPE: DNA
<213> ORGANISM: Oryza sativa

<400> SEQUENCE: 23

atggagcgtt cactgctgcc gtggttgctt cttcttctct gcttcgccga cggcgtattc     60

caatctcgtg cacagccaga cagcaaaggt ttcattagca tagactgtgg tatccagccg    120

aacacgagct acgtgcacaa cacgaccaag atatcctacg tcgccgacga cgacttcacc    180

gacggcggct ccaactacaa cgtttcgccg gagtacatca aaccgcagct ctcgcagcgg    240

tactacaact tgcgtgcctt ccccgacggt gcgcgcaact gctacacggc ccggtcgctg    300

gcgcctggga tcaagtacct catccgcgcc tctttcttgt atggcaacta cgacggcctc    360

aacaagctgc cggtgtttca tctctacatt ggcgtcaact tctggaccat ggtgaacatc    420

acgagcctcg gcctcggcgg ctctcgttat gaggaggcca tcgtggtggt gcccgatgac    480

tttgtgcagg tctgcctgat caacactggc accggcacgc ccttcatctc ctcgctggag    540

ctgaggcctc tggacaaaag gctctatccg caggtgaacg ccacgctggg cctcctccag    600

ctcaaccgcc tcaactttgg cccgactgat aacagcctcg tcaggtaccc agatgaccca    660

catgacagat tttggggaaa ctgggacagc tatacatcga gcttatggaa ggagatatcc    720

acggcgtcga gggtagataa cttagacgga gacatattcg atgcgccgac ggcggtgatg    780

cagacggcag tgacgccgcg caacgcgtca ggtaacatct acttcttttg ggagccttgg    840

ccgcagccaa acgacccgac gccgccgtac actgtcatct tccacttctc cgagctggag    900

atcctcacca acaacgcctc gcgccagttc tacatcaatc tcaacggcga accgttgatc    960

gatactgctt acgagccgac ataccttaca gcgagatact tatatggctt ggagcccctt   1020

gaaagaacct ccaggtacaa tatcaccatc aacgctaccg ccaactcgac gctgccgccg   1080

ctcatcaacg ccgccgagat ttctcgatc atctccaccg cagtcatcgg cacggactcg    1140

caggatgcat cttccatgat ggcgatcaag gacaagtacc aagtcaagaa gaattggatg   1200

ggtgacccgt gtatgccaaa gacatttgcg tgggacaagc tgacctgcag ctatcccaat   1260

tcgagcggtg caagaatcat aagcttaaat ctgtcctcca gtggtttgag tgctgacata   1320

tcatccgctt ttgggaatct caaggctctt caatacttgg atctatcaaa caacagtttg   1380

accggctcaa ttccggatgt cctctcacaa ttaccttcct tgagagtttt agatctgaca   1440

ggaaatcaac tcagtggatc aattccatct ggaattctca agaggattca agatggctcc   1500
```

```
ttaaatgtaa gatatggaaa taatccaaac ctatgcatca acggcaattc atgcaaggca   1560

gctaaaaaga agagcaagct agccatctac acagttattc ctgcagttct ggttgtattg   1620

atagcatcag ttacaacact cttttgcctg ctgagacgaa aaaagcaagg accaatgaac   1680

aattctctag agcagcaaaa cgagatgtcg acatcaacaa gccacgtgct gataaatagt   1740

ggatatggtg acaatgtatc gctgcggctt gagaaccgtc ggtttacata taaagaacta   1800

gagaagataa ccaacaaatt caaacgagtg ctcggacggg gagggttcgg atatgtctac   1860

catggcttct tggaggatgg cacagaagtg gcggtcaagt tgcgatctga atcctcaagc   1920

caaggtgcta aggagttcct catagaggct caaattttga cccggattca ccataagaat   1980

cttgtatcta tgatcagtta ctgcaaggat gggatataca tggctcttgt ctacgagtac   2040

atgccagaag gaaccctaga agaacatatt gtaggggaaa acaaaaaagg gaaaatactt   2100

aacatggaga gagaggctca atatcgcatt ggaatctgca caagggatgt gaaggcgacc   2160

aacatcctac taaacacaag gttggaggca aagattgccg attttggctt gtccaaggca   2220

tccagctatg acaacatcac ccatgtatcc acgaacgctc tcgttggcac acttggatat   2280

gtcgatccag agtaccagat gacaatgcaa gcaacaacaa agagcgatgt ctatagcttt   2340

ggcgtcgtct tattggagct ggtcactggg aagccggcta tcttgcatga accaaacccc   2400

atcagcgtca tccactggac acgacaacgt ctagcacggg gtaacatcga ggatgttgtg   2460

gacacatgca tgcctagtga ttatgatgta aatggtgtgt ggaaggctat ggacattgcg   2520

ttcacgtgca ctgcacaagc atcgacacaa cgactcacta tgactgaagt ggtgatgcag   2580

ttgcaagagt gtctcgagct tgaggatgca cgttgtgcta ttggcgatgc acacaacgag   2640

ttctaccctg accctcggag cgaccacaat ttaagttata acacgtatgt ctcggaccgg   2700

tccaacgatg ttttagaatg a                                             2721
```

```
<210> SEQ ID NO 24
<211> LENGTH: 906
<212> TYPE: PRT
<213> ORGANISM: Oryza sativa

<400> SEQUENCE: 24

Met Glu Arg Ser Leu Leu Pro Trp Leu Leu Leu Leu Leu Cys Phe Ala
1               5                   10                  15

Asp Gly Val Phe Gln Ser Arg Ala Gln Pro Asp Ser Lys Gly Phe Ile
            20                  25                  30

Ser Ile Asp Cys Gly Ile Gln Pro Asn Thr Ser Tyr Val His Asn Thr
        35                  40                  45

Thr Lys Ile Ser Tyr Val Ala Asp Asp Asp Phe Thr Asp Gly Gly Ser
    50                  55                  60

Asn Tyr Asn Val Ser Pro Glu Tyr Ile Lys Pro Gln Leu Ser Gln Arg
65                  70                  75                  80

Tyr Tyr Asn Leu Arg Ala Phe Pro Asp Gly Ala Arg Asn Cys Tyr Thr
                85                  90                  95

Ala Arg Ser Leu Ala Pro Gly Ile Lys Tyr Leu Ile Arg Ala Ser Phe
            100                 105                 110

Leu Tyr Gly Asn Tyr Asp Gly Leu Asn Lys Leu Pro Val Phe His Leu
        115                 120                 125

Tyr Ile Gly Val Asn Phe Trp Thr Met Val Asn Ile Thr Ser Leu Gly
    130                 135                 140

Leu Gly Gly Ser Arg Tyr Glu Glu Ala Ile Val Val Val Pro Asp Asp
145                 150                 155                 160
```

-continued

```
Phe Val Gln Val Cys Leu Ile Asn Thr Gly Thr Gly Thr Pro Phe Ile
                165                 170                 175

Ser Ser Leu Glu Leu Arg Pro Leu Asp Lys Arg Leu Tyr Pro Gln Val
            180                 185                 190

Asn Ala Thr Leu Gly Leu Leu Gln Leu Asn Arg Leu Asn Phe Gly Pro
        195                 200                 205

Thr Asp Asn Ser Leu Val Arg Tyr Pro Asp Asp Pro His Asp Arg Phe
    210                 215                 220

Trp Gly Asn Trp Asp Ser Tyr Thr Ser Ser Leu Trp Lys Glu Ile Ser
225                 230                 235                 240

Thr Ala Ser Arg Val Asp Asn Leu Asp Gly Asp Ile Phe Asp Ala Pro
                245                 250                 255

Thr Ala Val Met Gln Thr Ala Val Thr Pro Arg Asn Ala Ser Gly Asn
            260                 265                 270

Ile Tyr Phe Phe Trp Glu Pro Trp Pro Gln Pro Asn Asp Pro Thr Pro
        275                 280                 285

Pro Tyr Thr Val Ile Phe His Phe Ser Glu Leu Glu Ile Leu Thr Asn
    290                 295                 300

Asn Ala Ser Arg Gln Phe Tyr Ile Asn Leu Asn Gly Glu Pro Leu Ile
305                 310                 315                 320

Asp Thr Ala Tyr Glu Pro Thr Tyr Leu Thr Ala Arg Tyr Leu Tyr Gly
                325                 330                 335

Leu Glu Pro Leu Glu Arg Thr Ser Arg Tyr Asn Ile Thr Ile Asn Ala
            340                 345                 350

Thr Ala Asn Ser Thr Leu Pro Pro Leu Ile Asn Ala Ala Glu Ile Phe
        355                 360                 365

Ser Ile Ile Ser Thr Ala Val Ile Gly Thr Asp Ser Gln Asp Ala Ser
    370                 375                 380

Ser Met Met Ala Ile Lys Asp Lys Tyr Gln Val Lys Lys Asn Trp Met
385                 390                 395                 400

Gly Asp Pro Cys Met Pro Lys Thr Phe Ala Trp Asp Lys Leu Thr Cys
                405                 410                 415

Ser Tyr Pro Asn Ser Ser Gly Ala Arg Ile Ile Ser Leu Asn Leu Ser
            420                 425                 430

Ser Ser Gly Leu Ser Ala Asp Ile Ser Ser Ala Phe Gly Asn Leu Lys
        435                 440                 445

Ala Leu Gln Tyr Leu Asp Leu Ser Asn Asn Ser Leu Thr Gly Ser Ile
    450                 455                 460

Pro Asp Val Leu Ser Gln Leu Pro Ser Leu Arg Val Leu Asp Leu Thr
465                 470                 475                 480

Gly Asn Gln Leu Ser Gly Ser Ile Pro Ser Gly Ile Leu Lys Arg Ile
                485                 490                 495

Gln Asp Gly Ser Leu Asn Val Arg Tyr Gly Asn Asn Pro Asn Leu Cys
            500                 505                 510

Ile Asn Gly Asn Ser Cys Lys Ala Ala Lys Lys Lys Ser Lys Leu Ala
        515                 520                 525

Ile Tyr Thr Val Ile Pro Ala Val Leu Val Val Leu Ile Ala Ser Val
    530                 535                 540

Thr Thr Leu Phe Cys Leu Leu Arg Arg Lys Lys Gln Gly Pro Met Asn
545                 550                 555                 560

Asn Ser Leu Glu Gln Gln Asn Glu Met Ser Thr Ser Thr Ser His Val
                565                 570                 575

Leu Ile Asn Ser Gly Tyr Gly Asp Asn Val Ser Leu Arg Leu Glu Asn
            580                 585                 590
```

```
Arg Arg Phe Thr Tyr Lys Glu Leu Glu Lys Ile Thr Asn Lys Phe Lys
        595                 600                 605

Arg Val Leu Gly Arg Gly Gly Phe Gly Tyr Val Tyr His Gly Phe Leu
    610                 615                 620

Glu Asp Gly Thr Glu Val Ala Val Lys Leu Arg Ser Glu Ser Ser Ser
625                 630                 635                 640

Gln Gly Ala Lys Glu Phe Leu Ile Glu Ala Gln Ile Leu Thr Arg Ile
                645                 650                 655

His His Lys Asn Leu Val Ser Met Ile Ser Tyr Cys Lys Asp Gly Ile
            660                 665                 670

Tyr Met Ala Leu Val Tyr Glu Tyr Met Pro Glu Gly Thr Leu Glu Glu
        675                 680                 685

His Ile Val Gly Glu Asn Lys Lys Gly Lys Ile Leu Asn Met Glu Arg
    690                 695                 700

Glu Ala Gln Tyr Arg Ile Gly Ile Cys Thr Arg Asp Val Lys Ala Thr
705                 710                 715                 720

Asn Ile Leu Leu Asn Thr Arg Leu Glu Ala Lys Ile Ala Asp Phe Gly
                725                 730                 735

Leu Ser Lys Ala Ser Ser Tyr Asp Asn Ile Thr His Val Ser Thr Asn
            740                 745                 750

Ala Leu Val Gly Thr Leu Gly Tyr Val Asp Pro Glu Tyr Gln Met Thr
        755                 760                 765

Met Gln Ala Thr Thr Lys Ser Asp Val Tyr Ser Phe Gly Val Val Leu
    770                 775                 780

Leu Glu Leu Val Thr Gly Lys Pro Ala Ile Leu His Glu Pro Asn Pro
785                 790                 795                 800

Ile Ser Val Ile His Trp Thr Arg Gln Arg Leu Ala Arg Gly Asn Ile
                805                 810                 815

Glu Asp Val Val Asp Thr Cys Met Pro Ser Asp Tyr Asp Val Asn Gly
            820                 825                 830

Val Trp Lys Ala Met Asp Ile Ala Phe Thr Cys Thr Ala Gln Ala Ser
        835                 840                 845

Thr Gln Arg Leu Thr Met Thr Glu Val Val Met Gln Leu Gln Glu Cys
    850                 855                 860

Leu Glu Leu Glu Asp Ala Arg Cys Ala Ile Gly Asp Ala His Asn Glu
865                 870                 875                 880

Phe Tyr Pro Asp Pro Arg Ser Asp His Asn Leu Ser Tyr Asn Thr Tyr
                885                 890                 895

Val Ser Asp Arg Ser Asn Asp Val Leu Glu
            900                 905
```

<210> SEQ ID NO 25
<211> LENGTH: 2316
<212> TYPE: DNA
<213> ORGANISM: Oryza sativa

<400> SEQUENCE: 25

```
atggtgatca gctacagctg ctcggctggt accaagctga catggatatt gtcgttgctg      60

ctcatcctgg tcgcggcgac acaagtccat ggcgtgtctc ctcctgggtt tttaaacgtc     120

gactgcggat tgacaaatcg tagtacttac aatgacaccg acacaacttt gacgtacgtt     180

tctgacagag aatttgtcga gagcggcaag agctacgata ttatggcaca atacatggca     240

gatgctacaa atgaacaaga aaaaacgttg agaagcttcc ctgatggcca acggaactgt     300

tatacattac caaccaacag tagcaagaag tatctcatca gagccacctt cacttatgga     360
```

```
aactacgatg ggctcaactc gtcagagaag ggttctttgt ttatctttgg actccatatc    420
ggtgtcaact tctggacgac ggtaaacttg acaaagtggg atccatcgag cacggtatgg    480
aaagaggtga tcacggttgc tccggacaag tccgtatctg tctgtctgat aaacatggga    540
tcaggaactc ccttcatatc tacactagat cttaggccct tgcaagacac aatgtatccc    600
ttcgtgaatg cctcaacgtc cgtcagctat ttttctcgga taagatttgg atcggttgat    660
gaatacatca caagattccc aacggatcag tatgatcgct tctgggaggg ctgggtcttt    720
accatgcaca cctttccatg ggttaataag agtagcaacg gcaaggtggc tgaacttcct    780
aatattgaca cctttgggct tcctccagcc attctgggaa gcgcttcaac cataaacgga    840
aacttctctt ggctcaacat cagcgttagt gccagtaact ctctcgcaac agacctagag    900
cttcttccag tctttcactt tgttgaactc ggcaataatg gttcaaagag aatttttgac    960
atctacaatg tcgatgaacc gcaagcactg ttctccaact tcagcccacc gtcattcctg   1020
agctccatgt tccacaactg gttcttgcgc aaaggcagaa gggcatattt tcagcttcgc   1080
aagaccccag actcacagct accacctctt attaacgcat atgaggtgta ctcccgtgtc   1140
caggtggaga acttcaccac tgcttcaagt gatgggaagt caagaaaatc agaagaagaa   1200
gattatgata tgtatgaaga ggagactccc ctacatatcg acatcagaag gttcacatat   1260
gcagagctga agctcataac taacaatttc caatcaatca ttggaaaagg aggttttggt   1320
actgtttatc atggcatact ggaaaataat gatgaagtag ctgttaaggt tcttgtggag   1380
acatccatag cagagtcaaa agactttctc cctgagaaac aaccaaatct taatgggtac   1440
cgacatataa aatcaaatca aggtacaaac cttgtcaaaa gttcatcaca agaatcttgt   1500
cgctttgtgg tatttgcact accatgcaca tatcgaatgg atttctataa tgccattaat   1560
gtagcacact ttgatgcagg atatgacagt ttgaattggg aagagcgact tcacattgca   1620
cttgatgctg cacaagtagg tctggaatac cttcatgaat catgcacccc atcaatagtt   1680
cacagagatg tgaagacacc caacatcctt ctggacaaga atctggtggc caagatatct   1740
gattttgggc tttcacgggc ttttaatgct gctcacacgc atatatctac tgttgctgct   1800
ggcactcttg gttaccttga ccctgagtac catgccactt tccagcttac tgttaagaca   1860
gacgtttaca gttttggaat cgtcctcttg gagattgtga ctggtcaacc cccggtattc   1920
atggaccctc aaaccgtcca cctgccaaat tgggtgcgac aaaagattgc taatgggagc   1980
gttcacgatg ttgtggacaa gaagctgttg gatcagtatg atgccacgca cctgcagact   2040
gtgatagacc tcgccatgaa ctgcctcgaa aacgcatcga ttgacaggcc aagcatgacc   2100
gaggttgttt ccgtgcttaa ggtgtgcttg ccgatttcaa gcgagagaca atcggcaact   2160
tcaacccctc gaaagaagaa cgtcatggat gcagagattc caagacagtt ccagttgatg   2220
atttctggag cttcaacaac aagctacgag ggcagctcct ttcagtctgg atataccggt   2280
ggggtatcag aaataagcca catttctggg cggtga                             2316
```

<210> SEQ ID NO 26
<211> LENGTH: 771
<212> TYPE: PRT
<213> ORGANISM: Oryza sativa

<400> SEQUENCE: 26

```
Met Val Ile Ser Tyr Ser Cys Ser Ala Gly Thr Lys Leu Thr Trp Ile
1               5                   10                  15

Leu Ser Leu Leu Leu Ile Leu Val Ala Ala Thr Gln Val His Gly Val
            20                  25                  30
```

```
Ser Pro Pro Gly Phe Leu Asn Val Asp Cys Gly Leu Thr Asn Arg Ser
        35                  40                  45

Thr Tyr Asn Asp Thr Asp Thr Thr Leu Thr Tyr Val Ser Asp Arg Glu
    50                  55                  60

Phe Val Glu Ser Gly Lys Ser Tyr Asp Ile Met Ala Gln Tyr Met Ala
65                  70                  75                  80

Asp Ala Thr Asn Glu Gln Glu Lys Thr Leu Arg Ser Phe Pro Asp Gly
                85                  90                  95

Gln Arg Asn Cys Tyr Thr Leu Pro Thr Asn Ser Ser Lys Lys Tyr Leu
            100                 105                 110

Ile Arg Ala Thr Phe Thr Tyr Gly Asn Tyr Asp Gly Leu Asn Ser Ser
        115                 120                 125

Glu Lys Gly Ser Leu Phe Ile Phe Gly Leu His Ile Gly Val Asn Phe
    130                 135                 140

Trp Thr Thr Val Asn Leu Thr Lys Trp Asp Pro Ser Ser Thr Val Trp
145                 150                 155                 160

Lys Glu Val Ile Thr Val Ala Pro Asp Lys Ser Val Ser Val Cys Leu
                165                 170                 175

Ile Asn Met Gly Ser Gly Thr Pro Phe Ile Ser Thr Leu Asp Leu Arg
            180                 185                 190

Pro Leu Gln Asp Thr Met Tyr Pro Phe Val Asn Ala Ser Thr Ser Val
        195                 200                 205

Ser Tyr Phe Ser Arg Ile Arg Phe Gly Ser Val Asp Glu Tyr Ile Thr
    210                 215                 220

Arg Phe Pro Thr Asp Gln Tyr Asp Arg Phe Trp Glu Gly Trp Val Phe
225                 230                 235                 240

Thr Met His Thr Phe Pro Trp Val Asn Lys Ser Ser Asn Gly Lys Val
                245                 250                 255

Ala Glu Leu Pro Asn Ile Asp Thr Phe Gly Leu Pro Pro Ala Ile Leu
            260                 265                 270

Gly Ser Ala Ser Thr Ile Asn Gly Asn Phe Ser Trp Leu Asn Ile Ser
        275                 280                 285

Val Ser Ala Ser Asn Ser Leu Ala Thr Asp Leu Glu Leu Leu Pro Val
    290                 295                 300

Phe His Phe Val Glu Leu Gly Asn Asn Gly Ser Lys Arg Ile Phe Asp
305                 310                 315                 320

Ile Tyr Asn Val Asp Glu Pro Gln Ala Leu Phe Ser Asn Phe Ser Pro
                325                 330                 335

Pro Ser Phe Leu Ser Ser Met Phe His Asn Trp Phe Leu Arg Lys Gly
            340                 345                 350

Arg Arg Ala Tyr Phe Gln Leu Arg Lys Thr Pro Asp Ser Gln Leu Pro
        355                 360                 365

Pro Leu Ile Asn Ala Tyr Glu Val Tyr Ser Arg Val Gln Val Glu Asn
    370                 375                 380

Phe Thr Thr Ala Ser Ser Asp Gly Lys Ser Arg Lys Ser Glu Glu Glu
385                 390                 395                 400

Asp Tyr Asp Met Tyr Glu Glu Glu Thr Pro Leu His Ile Asp Ile Arg
                405                 410                 415

Arg Phe Thr Tyr Ala Glu Leu Lys Leu Ile Thr Asn Asn Phe Gln Ser
            420                 425                 430

Ile Ile Gly Lys Gly Gly Phe Gly Thr Val Tyr His Gly Ile Leu Glu
        435                 440                 445

Asn Asn Asp Glu Val Ala Val Lys Val Leu Val Glu Thr Ser Ile Ala
```

```
    450                 455                 460

Glu Ser Lys Asp Phe Leu Pro Glu Lys Gln Pro Asn Leu Asn Gly Tyr
465                 470                 475                 480

Arg His Ile Lys Ser Asn Gln Gly Thr Asn Leu Val Lys Ser Ser Ser
                485                 490                 495

Gln Glu Ser Cys Arg Phe Val Val Phe Ala Leu Pro Cys Thr Tyr Arg
            500                 505                 510

Met Asp Phe Tyr Asn Ala Ile Asn Val Ala His Phe Asp Ala Gly Tyr
        515                 520                 525

Asp Ser Leu Asn Trp Glu Glu Arg Leu His Ile Ala Leu Asp Ala Ala
    530                 535                 540

Gln Val Gly Leu Glu Tyr Leu His Glu Ser Cys Thr Pro Ser Ile Val
545                 550                 555                 560

His Arg Asp Val Lys Thr Pro Asn Ile Leu Leu Asp Lys Asn Leu Val
                565                 570                 575

Ala Lys Ile Ser Asp Phe Gly Leu Ser Arg Ala Phe Asn Ala Ala His
            580                 585                 590

Thr His Ile Ser Thr Val Ala Ala Gly Thr Leu Gly Tyr Leu Asp Pro
        595                 600                 605

Glu Tyr His Ala Thr Phe Gln Leu Thr Val Lys Thr Asp Val Tyr Ser
    610                 615                 620

Phe Gly Ile Val Leu Leu Glu Ile Val Thr Gly Gln Pro Pro Val Phe
625                 630                 635                 640

Met Asp Pro Gln Thr Val His Leu Pro Asn Trp Val Arg Gln Lys Ile
                645                 650                 655

Ala Asn Gly Ser Val His Asp Val Val Asp Lys Lys Leu Leu Asp Gln
            660                 665                 670

Tyr Asp Ala Thr His Leu Gln Thr Val Ile Asp Leu Ala Met Asn Cys
        675                 680                 685

Leu Glu Asn Ala Ser Ile Asp Arg Pro Ser Met Thr Glu Val Val Ser
    690                 695                 700

Val Leu Lys Val Cys Leu Pro Ile Ser Ser Glu Arg Gln Ser Ala Thr
705                 710                 715                 720

Ser Thr Pro Arg Lys Lys Asn Val Met Asp Ala Glu Ile Pro Arg Gln
                725                 730                 735

Phe Gln Leu Met Ile Ser Gly Ala Ser Thr Thr Ser Tyr Glu Gly Ser
            740                 745                 750

Ser Phe Gln Ser Gly Tyr Thr Gly Gly Val Ser Glu Ile Ser His Ile
        755                 760                 765

Ser Gly Arg
    770
```

<210> SEQ ID NO 27
<211> LENGTH: 2604
<212> TYPE: DNA
<213> ORGANISM: Oryza sativa

<400> SEQUENCE: 27

```
atgcaggctc acagcagcca gcaggacaca atacaagatg catgctgtct tctgctggtc      60

atccccatcg aaagccggtg caattccgaa gtgttaacag acctgcgccc ctatctgaag     120

ggaaaagagg cagccaccga aagaatgttt gcaggtctct tctactgtct gacaaagtgg     180

gcagaagggt tcacaaacat tgactgtggc ttcgtagacg gcgagagtta cacggacagc     240

acaacaaatt taacatacgt acctgatcat gaattcgttg aaggcggcac acaccatgaa     300
```

-continued

```
gttgtgccaa agctaattag tggatccacc gatgagcaag agaaaacctt gagaagcttc    360

cctgatggcc aacgcaactg ttacacaata ccgtccacta gtggtaagaa gtatctcatc    420

agaacaacct tcacttacgg aaactacgat ggactcaggt cgtcagagaa cggttcctta    480

tttctgtttg gactccacat cggcgtcaac ttctggacaa cggtgaactt gacaaaacag    540

gactcatcag acactatctg gaaagaggtg ctcacggttg ctccggacga gttcatatat    600

gtgtgcctgg taaactttgg atcaggaacc cctttcattt ctgcattgga gttgcggcaa    660

ttggatgatc caatgtaccc attcctgaat ctttttgtgt ctgtaagcta ctttactcga    720

atgagatttg gggcagtcga tgatttcatc acaagatatc caactgatct ctttgatcgt    780

ttctgggaag cagcccaatg ctactcctat ccctggctca acctgaccac caaccaaaca    840

gtgaacaagc tcccaggaaa tgacaacttc caggtgccaa cactcatcgt ccagaaggca    900

tccaccatca acagcggttt ttcatggctc aacatcagca taacggccgg tgataacctg    960

aatggccaga gcctggagct tctcccgatc ttccactttg ctgagataga aaagaaccgc   1020

ccaaatcgga cgttccaaat ctatagtgat ggcaacgagc tgcaccaggc cttctcaccg   1080

tcctacttgc aggtggacag cgtgtacctg agggaccggt acctacatga gtcaggtaca   1140

actttcaccc tgtgcaagac aaacagctcg gagctcccac cactcatcaa cgcctttgag   1200

gcttactcgc ttgttcggat ggaaaacctc accactgaca ccatcgatgt cagttccatg   1260

aaacaagtaa agacgcagta caatgtgcaa cgaagaagtt ggaatggaga tccatgttct   1320

ccaaaagagt atacctggga aggtgtgaaa tgcaactact atgatggcaa acagaatccc   1380

aggatcatcc tagtattaga aggaaatccc atgtgctcaa atataagtga aagctactgt   1440

gccatgcaag cagataaggc gaagaagaat acagcaacat tgctcattgc agtgatagtt   1500

cctgttgtag ctattacact tatgttattt ctatggatgc tctgctgtaa aggaaaacca   1560

aaagaacatg atgattatga tatgtatgaa gaggaaaatc ccctgcatag cgacaccaga   1620

agattcacat atacagagtt gaggactata acgaacaact tccagtctat cattggaaat   1680

ggaggatttg gtacagttta tcatggcata ttggggaatg gagaggaagt cgcagtcaag   1740

gtgcttcggg agacatctag agccctatca aaggacttcc tccctgaggt gcaaacattg   1800

tcaaaagttc atcacaagaa tctcgtcaca tttttaggat attgcctaaa caagaaatgc   1860

cttgcccttg tgtacgattt catgtctaga ggaaacttac aagaagtttt aagaggagga   1920

ctggagtatc tacatgaatc atgcacccca gcaattgttc acagagatgt aaaaacggca   1980

aacatacttc tcgatgagaa tcttgtggcc atgatatctg actttggtct ttcacgatct   2040

tacactcccg cacacacaca catatcaact attgctgccg gtactgttgg ctaccttgac   2100

ccagagtacc atgctacttt ccaactcact gtgaaagcag atgtctacag ttttggcatt   2160

gtccttctag agatcattac cggccaacct tcggttttag tggacccaga accagtgcat   2220

ctaccaaact gggtacgcca aaagattgct agaggaagca ttcatgatgc tgtggacagt   2280

agactgatgc atcagtatga tgccacttct gtacagagtg tcatagacct tgccatgaac   2340

tgtgtgggaa atgtgtccat tgataggccg agcatgaccg aaattgttat caagctcaaa   2400

gagtgcttac tggcaggtac aggtaaaaag caactggtgt ctggctccta taaacagaag   2460

gacgccatgg acgctggcat tgcaaggcag ttccagctgc tgatttctgg agttccaata   2520

gtaagtaacg agtgtatatc aggtggcatc acagaattaa gttattattc aggaagctca   2580

accgtggaac aagttggtgc ctga                                          2604
```

<210> SEQ ID NO 28

<211> LENGTH: 867
<212> TYPE: PRT
<213> ORGANISM: Oryza sativa

<400> SEQUENCE: 28

```
Met Gln Ala His Ser Ser Gln Gln Asp Thr Ile Gln Asp Ala Cys Cys
1               5                   10                  15

Leu Leu Leu Val Ile Pro Ile Glu Ser Arg Cys Asn Ser Glu Val Leu
            20                  25                  30

Thr Asp Leu Arg Pro Tyr Leu Lys Gly Lys Glu Ala Ala Thr Glu Arg
        35                  40                  45

Met Phe Ala Gly Leu Phe Tyr Cys Leu Thr Lys Trp Ala Glu Gly Phe
    50                  55                  60

Thr Asn Ile Asp Cys Gly Phe Val Asp Gly Glu Ser Tyr Thr Asp Ser
65                  70                  75                  80

Thr Thr Asn Leu Thr Tyr Val Pro Asp His Glu Phe Val Glu Gly Gly
                85                  90                  95

Thr His His Glu Val Val Pro Lys Leu Ile Ser Gly Ser Thr Asp Glu
            100                 105                 110

Gln Glu Lys Thr Leu Arg Ser Phe Pro Asp Gly Gln Arg Asn Cys Tyr
        115                 120                 125

Thr Ile Pro Ser Thr Ser Gly Lys Lys Tyr Leu Ile Arg Thr Thr Phe
    130                 135                 140

Thr Tyr Gly Asn Tyr Asp Gly Leu Arg Ser Ser Glu Asn Gly Ser Leu
145                 150                 155                 160

Phe Leu Phe Gly Leu His Ile Gly Val Asn Phe Trp Thr Thr Val Asn
                165                 170                 175

Leu Thr Lys Gln Asp Ser Ser Asp Thr Ile Trp Lys Glu Val Leu Thr
            180                 185                 190

Val Ala Pro Asp Glu Phe Ile Tyr Val Cys Leu Val Asn Phe Gly Ser
        195                 200                 205

Gly Thr Pro Phe Ile Ser Ala Leu Glu Leu Arg Gln Leu Asp Asp Pro
    210                 215                 220

Met Tyr Pro Phe Leu Asn Leu Phe Val Ser Val Ser Tyr Phe Thr Arg
225                 230                 235                 240

Met Arg Phe Gly Ala Val Asp Asp Phe Ile Thr Arg Tyr Pro Thr Asp
                245                 250                 255

Leu Phe Asp Arg Phe Trp Glu Ala Ala Gln Cys Tyr Ser Tyr Pro Trp
            260                 265                 270

Leu Asn Leu Thr Thr Asn Gln Thr Val Asn Lys Leu Pro Gly Asn Asp
        275                 280                 285

Asn Phe Gln Val Pro Thr Leu Ile Val Gln Lys Ala Ser Thr Ile Asn
    290                 295                 300

Ser Gly Phe Ser Trp Leu Asn Ile Ser Ile Thr Ala Gly Asp Asn Leu
305                 310                 315                 320

Asn Gly Gln Ser Leu Glu Leu Leu Pro Ile Phe His Phe Ala Glu Ile
                325                 330                 335

Glu Lys Asn Arg Pro Asn Arg Thr Phe Gln Ile Tyr Ser Asp Gly Asn
            340                 345                 350

Glu Leu His Gln Ala Phe Ser Pro Ser Tyr Leu Gln Val Asp Ser Val
        355                 360                 365

Tyr Leu Arg Asp Arg Tyr Leu His Glu Ser Gly Thr Thr Phe Thr Leu
    370                 375                 380

Cys Lys Thr Asn Ser Ser Glu Leu Pro Pro Leu Ile Asn Ala Phe Glu
385                 390                 395                 400
```

```
Ala Tyr Ser Leu Val Arg Met Glu Asn Leu Thr Thr Asp Thr Ile Asp
                405                 410                 415

Val Ser Ser Met Lys Gln Val Lys Thr Gln Tyr Asn Val Gln Arg Arg
            420                 425                 430

Ser Trp Asn Gly Asp Pro Cys Ser Pro Lys Glu Tyr Thr Trp Glu Gly
        435                 440                 445

Val Lys Cys Asn Tyr Tyr Asp Gly Lys Gln Asn Pro Arg Ile Ile Leu
    450                 455                 460

Val Leu Glu Gly Asn Pro Met Cys Ser Asn Ile Ser Glu Ser Tyr Cys
465                 470                 475                 480

Ala Met Gln Ala Asp Lys Ala Lys Lys Asn Thr Ala Thr Leu Leu Ile
                485                 490                 495

Ala Val Ile Val Pro Val Val Ala Ile Thr Leu Met Leu Phe Leu Trp
            500                 505                 510

Met Leu Cys Cys Lys Gly Lys Pro Lys Glu His Asp Asp Tyr Asp Met
        515                 520                 525

Tyr Glu Glu Glu Asn Pro Leu His Ser Asp Thr Arg Arg Phe Thr Tyr
    530                 535                 540

Thr Glu Leu Arg Thr Ile Thr Asn Asn Phe Gln Ser Ile Ile Gly Asn
545                 550                 555                 560

Gly Gly Phe Gly Thr Val Tyr His Gly Ile Leu Gly Asn Gly Glu Glu
                565                 570                 575

Val Ala Val Lys Val Leu Arg Glu Thr Ser Arg Ala Leu Ser Lys Asp
            580                 585                 590

Phe Leu Pro Glu Val Gln Thr Leu Ser Lys Val His His Lys Asn Leu
        595                 600                 605

Val Thr Phe Leu Gly Tyr Cys Leu Asn Lys Lys Cys Leu Ala Leu Val
    610                 615                 620

Tyr Asp Phe Met Ser Arg Gly Asn Leu Gln Glu Val Leu Arg Gly Gly
625                 630                 635                 640

Leu Glu Tyr Leu His Glu Ser Cys Thr Pro Ala Ile Val His Arg Asp
                645                 650                 655

Val Lys Thr Ala Asn Ile Leu Leu Asp Glu Asn Leu Val Ala Met Ile
            660                 665                 670

Ser Asp Phe Gly Leu Ser Arg Ser Tyr Thr Pro Ala His Thr His Ile
        675                 680                 685

Ser Thr Ile Ala Ala Gly Thr Val Gly Tyr Leu Asp Pro Glu Tyr His
    690                 695                 700

Ala Thr Phe Gln Leu Thr Val Lys Ala Asp Val Tyr Ser Phe Gly Ile
705                 710                 715                 720

Val Leu Leu Glu Ile Ile Thr Gly Gln Pro Ser Val Leu Val Asp Pro
                725                 730                 735

Glu Pro Val His Leu Pro Asn Trp Val Arg Gln Lys Ile Ala Arg Gly
            740                 745                 750

Ser Ile His Asp Ala Val Asp Ser Arg Leu Met His Gln Tyr Asp Ala
        755                 760                 765

Thr Ser Val Gln Ser Val Ile Asp Leu Ala Met Asn Cys Val Gly Asn
    770                 775                 780

Val Ser Ile Asp Arg Pro Ser Met Thr Glu Ile Val Ile Lys Leu Lys
785                 790                 795                 800

Glu Cys Leu Leu Ala Gly Thr Gly Lys Lys Gln Leu Val Ser Gly Ser
                805                 810                 815

Tyr Lys Gln Lys Asp Ala Met Asp Ala Gly Ile Ala Arg Gln Phe Gln
```

```
            820                 825                 830

Leu Leu Ile Ser Gly Val Pro Ile Val Ser Asn Glu Cys Ile Ser Gly
        835                 840                 845

Gly Ile Thr Glu Leu Ser Tyr Tyr Ser Gly Ser Ser Thr Val Glu Gln
    850                 855                 860

Val Gly Ala
865
```

<210> SEQ ID NO 29
<211> LENGTH: 2607
<212> TYPE: DNA
<213> ORGANISM: Oryza sativa

<400> SEQUENCE: 29

```
atggttgacg gacggagagg gtaccgccaa acgattaatc ggaatacgga cgatttatcg     60

gaatttgacg gatatttaac aaaactgtta cttacaggga agtgtgtctg tgcagggttt    120

ttaaacatcg actgcggatt gacaaatcgt agtacttata atgacaccga cacaactttg    180

acgtacgttt ctgacagaga atttgttgag ggcggcaacg gcaagagcta cgatattatg    240

gcacaataca tcgcagatgc tacaaatgaa caagaaaaaa cgttgagaag cttccctgat    300

ggccaacgga actgttatac attaccaacc aacagtagca agaagtatct catcagagcc    360

accttcactt atggaaacta cgatgggctc aactcgtcag agaagggttc tctgtttctc    420

tttggactcc acatcggcgt caacttctgg gcaacggtga acttgacaaa ctggggttca    480

tcagatacga tgtataaaga ggtgatcaca gttgctccag acaaattcat atccgtctgt    540

ctgataaact tgggatcagg aactcccttc gtatctacat tagacttgag ggaattggat    600

ggtgcaatgt tcccatttct gaatctttct gtttcaatca gccatttggc tcgacaaaga    660

tatggctcgg tcgatgatta catcacgaga tatccaactg atcccttcga tcgtttctgg    720

gaggcagccc tacgctacaa atttcccttc ctcaacatga ccaccaacca agacgtgaca    780

aagcttcctg gaaatgacga ctttcaggtg ccgatgccca tccttcagaa ggcctcaacc    840

ataagcagca atttctcaga gtttaacgtc agcgtgatat ttccggacaa catgaaaaac    900

atcgacaaca tcaacaacat cgactacagg agcttggagc tgctaccaat cttccacttt    960

gccgatattg gaggcaacaa ccagaataga acgtttgata tctataacga tggaaacctg   1020

atgtttccca actacatacc acccctgttc cgagcggaga gcacatatca gagtggtaag   1080

ttcttgcgca agaggggcct caacttcacc ctgcgcaaga cgcccagctc ggagctccag   1140

ccgctcatca acgcattcga ggtgtactcg cttgttcata cagacaacct caccacttct   1200

ccagacgacg ttgattacat gaaagaagtg aagaagtact acagttacac aagaaactgg   1260

aatggagatc catgctcccc aagagagtat tcctggcaag gtctggcttg cgactacgct   1320

aatggaaaca aaaatccaag gatcacccga atggatttat cgcacaacaa cttgacaggc   1380

gcaattccag actatcaact caattcactc agagtgcttg atagttcctg tggtatccct   1440

cctactcctt gtactggttt gtatcctctg gaggctgtgc tggaaaggtt ggagtttgca   1500

ggaaaatcag cagaacaaga agattattct atttatgaag aggaagctcc attacatatc   1560

gacatcaaac ggttcacata tgcagagctg aagctcataa ctaacaactt ccaatcaatc   1620

attggaaaag gaggttttgg cactgtttat catggcatac tggaaaataa cgatgaagta   1680

gctgttaagg tgcttgtgga gacatctata gcagagtcaa aagacttcct ccctgagagg   1740

aaatcttcag ctgtcatggt cgggataaca tatcaacgca gaagccgcac agggctgcag   1800

gatacggcgt caggagatgc agcgcagcgc actactaatt tcgcacactt tgatgcagga   1860
```

```
tatgatagta gtttgaattg ggaagaacga cttcacattg cacttgatgc tgcacaagga   1920

ctggagtatc tacatgaatc atgcagcccg tcaatagttc acagagatgt gaagacaccc   1980

aacatccttc tggacaagaa tctggtggcc aagatatctg attttgggct ttcacgggct   2040

tttaatgcag ctcacacgca tatatctact gttgttgccg gcacccttgg ttaccttgac   2100

cctgagtatc atgctacttt ccaacttacc gttaagacag acgtttacag ttttggaatt   2160

gtcctcttgg agattgtcac tggtcaaccc ccagtattta tggatcccca aaccgtccac   2220

ttgccaaatt gggtgcggca aaagattgat aagggaagca tccacgatgt tgtggacaag   2280

aaactgttag atcaatacga tgccactcac ctgcaaactg tgatagacct tgcaatgaac   2340

tgccttgaaa acacatcaat tgacaggcca agcatgactg aggttgtttc tgtgcttaag   2400

gtgttgttta cggtggctat ttcaagtgag aaacgatcgg ttacatcaac ccctcaagag   2460

aagaacgtca tggatgcaga cattccacgg cagttccact tgatgatttc tggagctaca   2520

acaacaagct acgacaacga gggcagttcc tcacagtctg gtcctaccgg tgggatgtca   2580

gaaataagct acatttctgg acggtga                                       2607
```

<210> SEQ ID NO 30
<211> LENGTH: 783
<212> TYPE: PRT
<213> ORGANISM: Oryza sativa

<400> SEQUENCE: 30

```
Met Leu His Ser Arg Asn Pro Asp Thr Thr Thr Pro Pro Ala Arg Arg
1               5                   10                  15

Gly Lys Lys Thr Arg Ser Leu Ala Ser Gln Gly Cys Thr Ala Phe Phe
            20                  25                  30

Ser Gln Thr Gln Leu Leu Val Thr Arg Ser Arg Asn Thr Ser Phe Glu
        35                  40                  45

Ser Lys Lys Leu Pro Ser Asn Tyr Gln Lys Asn Asn Gly Ser Ser Lys
    50                  55                  60

Arg Ser Ser Leu Lys Val Phe Leu Tyr Ala Gly Phe Leu Ser Ile Asp
65                  70                  75                  80

Cys Gly Tyr Thr Asp Ser Ala Gly Tyr Asp Asp Lys Asn Thr Met Leu
                85                  90                  95

Pro Tyr Val Ser Asp Lys Gly Tyr Ile Lys Gly Gly Lys Thr Phe Ser
            100                 105                 110

Ile Leu Ser Gln Tyr Met Lys Glu Ala Ala Asn Lys Gln Glu Glu Thr
        115                 120                 125

Leu Arg Ser Phe Pro Asp Gly Gln Arg Asn Cys Tyr Thr Leu Pro Thr
    130                 135                 140

Asn Arg Ser Lys Lys Tyr Leu Ile Arg Ala Thr Phe Thr Tyr Gly Asn
145                 150                 155                 160

Tyr Asp Gly Arg Asn Ser Ser Glu Ser Gly Ser Pro Phe Leu Phe Gly
                165                 170                 175

Leu His Ile Gly Ile Asn Phe Trp Thr Met Val Asn Leu Thr Lys Leu
            180                 185                 190

Pro Ser Ser Asn Thr Ile Trp Lys Glu Leu Ile Met Val Ala Pro Gly
        195                 200                 205

Asn Ser Val Ser Val Cys Leu Ile Asn Asn Glu Leu Gly Thr Pro Phe
    210                 215                 220

Ile Ser Thr Leu Asp Leu Arg Pro Leu Gln Asp Thr Met Tyr Pro Phe
225                 230                 235                 240
```

```
Val Asn Val Ser Val Ala Val Ser Tyr Phe Ser Arg Gln Arg Tyr Gly
                245                 250                 255

Gln Val Asn Asp Val Ile Thr Arg Tyr Pro Glu Asp Val Tyr Asp Arg
            260                 265                 270

Phe Trp Glu Gly Ala Phe His Thr Arg Ser Tyr Pro Trp Ile Asn Leu
        275                 280                 285

Asn Thr Thr Gln Glu Val Lys Arg Leu Pro Gly Asp Glu Lys Phe Met
    290                 295                 300

Val Pro Asn Thr Ile Leu Gln Lys Ala Ser Thr Ile Asn Ile Thr Phe
305                 310                 315                 320

Ser Trp Leu Asn Ile Thr Val Arg Gly Ala Asn Asn Leu Leu Gly Leu
                325                 330                 335

Gly Asp Leu Glu Leu Leu Pro Val Phe His Phe Ala Glu Ile Ala Ser
            340                 345                 350

Asn Thr Thr Arg Leu Phe Asp Ile Tyr Ser Asp Ser Glu Glu Leu Phe
        355                 360                 365

Ala Asn Phe Ser Pro Ser Pro Phe Gln Val Asp Ser Met Tyr Gln Asn
    370                 375                 380

Gly Arg Phe Leu Pro Gly Val Ser Ser Thr Phe Thr Leu Arg Lys Gln
385                 390                 395                 400

Pro Thr Ser Gln Pro Pro Leu Ile Asn Ala Phe Glu Val Tyr Ser Leu
                405                 410                 415

Val Arg Ile Ala Thr Ala Ser Asp Asp Gly Glu Gln Asn Ser Gly Leu
            420                 425                 430

Asn Ser Asp Ile Phe Val Tyr Thr Leu Tyr Ser Arg Ala Lys Trp Ile
        435                 440                 445

Glu Pro Phe Val Asn Cys Asp Leu Ala Gly Lys Ser Lys Glu His Asp
    450                 455                 460

Asp Tyr Asp Met Tyr Glu Glu Asp Thr Pro Leu His Thr Asp Thr Arg
465                 470                 475                 480

Arg Phe Thr Tyr Thr Glu Leu Lys Thr Ile Thr Asn Asn Phe Gln Ser
                485                 490                 495

Ile Ile Gly Lys Gly Gly Phe Gly Met Val Tyr His Gly Ile Leu Asp
            500                 505                 510

Asn Gly Glu Glu Val Ala Val Lys Val Gln Ile Leu Ser Lys Val Gln
        515                 520                 525

His Lys Asn Leu Val Thr Phe Leu Gly Tyr Cys His Asn Lys Lys Cys
    530                 535                 540

Leu Ala Leu Val Tyr Asp Phe Met Ala Arg Gly Asn Leu Gln Glu Val
545                 550                 555                 560

Leu Arg Gly Gly Leu Glu Tyr Leu His Glu Ser Cys Thr Pro Pro Ile
                565                 570                 575

Val His Arg Asp Val Lys Thr Ala Asn Ile Leu Leu Asp Lys Asn Leu
            580                 585                 590

Val Ala Met Ile Ser Asp Phe Gly Leu Ser Arg Ser Tyr Thr Pro Ala
        595                 600                 605

His Thr His Ile Ser Thr Val Ala Ala Gly Thr Val Gly Tyr Leu Asp
    610                 615                 620

Pro Glu Tyr His Ala Thr Phe His Leu Thr Val Lys Ala Asp Val Tyr
625                 630                 635                 640

Ser Phe Gly Ile Val Leu Leu Glu Ile Ile Thr Gly Gln Pro Ser Val
                645                 650                 655

Leu Val Asp Ser Glu Pro Val His Leu Pro Asn Trp Val Arg Gln Lys
            660                 665                 670
```

```
Ile Ala Glu Gly Ser Ile His Asp Ala Val Asp Ser Arg Leu Arg His
        675                 680                 685

Gln Tyr Asp Ala Thr Ser Ile Gln Ser Val Ile Asp Leu Ala Met Ser
    690                 695                 700

Cys Val Glu Asn Thr Ser Thr Asp Arg Pro Ser Met Thr Asp Ile Val
705                 710                 715                 720

Ile Lys Leu Lys Glu Cys Leu Pro Ala Gly Thr Gly Glu Met Gln Leu
                725                 730                 735

Val Ser Arg Ser Tyr Lys Gln Lys Glu Ala Met Asp Ala Asp Ile Ala
            740                 745                 750

Arg Gln Phe Gln Leu Leu Ile Ser Gly Val Ser Ile Glu Ser Ile Glu
        755                 760                 765

Gly Asn Ser Ser Gly Thr Thr Glu Leu Arg Tyr Pro Ser Gly Arg
    770                 775                 780


<210> SEQ ID NO 31
<211> LENGTH: 2352
<212> TYPE: DNA
<213> ORGANISM: Oryza sativa

<400> SEQUENCE: 31

atgttgcatt ccagaaatcc tgacaccacc actccaccag ctcgaagggg aaaaaaaact      60

cgcagcctcg cgtcgcaggg ctgcacagct ttcttctcac agacacagtt actagtaacc     120

cgcagtagga acaccagctt tgaatctaaa aaacttccat ccaattatca gaaaaacaac     180

ggaagcagca aacggagctc tcttaaagtg tttttatatg cagggttttt aagcatcgac     240

tgcggatata cagatagtgc tggctatgac gacaagaaca caatgttgcc atatgtctct     300

gacaaaggat atataaaggg cggcaagacc ttcagtattc tgtcacagta catgaaagaa     360

gctgcaaata agcaagaaga aaccctgaga agtttccctg atggccaacg gaactgttat     420

acattaccaa ccaaccgtag caagaagtat ctcatcagag ccaccttcac ttacgggaac     480

tacgatggcc gcaactcatc agagagtggt tcaccgtttc tctttggact ccatatcggc     540

atcaacttct ggacaatggt gaacctgaca aaattgcctt catcgaacac aatctggaaa     600

gagctgatca tggttgctcc aggcaattcc gtatctgttt gtctgataaa caacgaattg     660

gggactccct tcatatcgac attggatttg aggcccttgc aagatacaat gtaccccttt     720

gtgaatgttt ctgtggccgt cagttatttt tctcggcaaa gatatggaca agtcaatgat     780

gtcatcacta gatatccaga ggatgtttac gaccggtttt gggagggagc gttccacacc     840

agatcctatc cctggatcaa ccttaacaca acacaagaag tgaaaaggct cccaggtgat     900

gaaaagttca tggtgccgaa taccatcctc cagaaagctt caaccataaa catcacattc     960

agttggctca acatcactgt gaggggcgcc aacaacctgc ttggcttggg ggatctggag    1020

ctgctaccgg tctttcactt tgctgagata gccagcaaca cgaccaggtt gttcgatatc    1080

tacagcgaca gcgaggagct gttcgccaac ttctcaccat ccccctcca ggtggacagc    1140

atgtaccaga atggccggtt cttgcccggt gtgagctcaa ctttcacgtt gcgcaagcag    1200

cccacatcac agccaccgct catcaacgcg ttcgaggtgt attcacttgt ccggatagct    1260

actgcttctg atgatggtga acaaaacagt gggttaaatt cagatatttt cgtgtataca    1320

ctatacagta gagcaaagtg gattgagcca tttgtgaatt gtgacttagc aggaaaatca    1380

aaagaacatg atgattatga tatgtatgaa gaggatactc ccctgcatac tgacaccaga    1440

agattcacat atacagagtt gaagactata actaacaact tccagtctat cattggaaaa    1500
```

```
ggaggatttg gtatggttta tcatggcata ttggacaatg gagaggaagt ggcagtcaag   1560

gtgcaaatat tgtcaaaagt tcaacacaag aatctcgtca cgtttttagg atattgccac   1620

aacaagaaat gccttgccct tgtgtacgat ttcatggcta gaggaaacct acaagaagtt   1680

ttaagaggag gactggagta tctgcatgaa tcatgcaccc cgccaatagt tcacagagat   1740

gtgaaaactg caaacattct cctggataag aatcttgtgg ccatgatatc tgactttggt   1800

ctttcacgat cttacactcc agcgcacaca cacatatcaa ctgttgctgc cggtactgtt   1860

ggctaccttg accctgagta ccatgctact ttccacctca ctgtgaaagc agatgtctac   1920

agcttcggca ttgtcctctt ggagatcatt actggccaac cttcagtgtt agtggactca   1980

gaaccagtgc acctaccaaa ctgggtgcgc caaaagattg ctgaagggag cattcatgat   2040

gctgtagaca gtagactaag gcatcagtat gatgccactt ccatacagag tgtcatagat   2100

cttgccatga gctgtgtgga aaacacatcc actgataggc caagcatgac tgacattgtt   2160

atcaagctca aagaatgcct accggcaggt acaggtgaaa tgcaactggt gtctaggtcc   2220

tataaacaga aggaagccat ggacgctgac atagcgaggc aattccagct gctgatttct   2280

ggagtttcaa tagaaagcat tgagggcaac tcaagtggga ccacagaatt aagatatcct   2340

tcgggaaggt ga                                                       2352
```

```
<210> SEQ ID NO 32
<211> LENGTH: 868
<212> TYPE: PRT
<213> ORGANISM: Oryza sativa

<400> SEQUENCE: 32

Met Val Asp Gly Arg Arg Gly Tyr Arg Gln Thr Ile Asn Arg Asn Thr
1               5                   10                  15

Asp Asp Leu Ser Glu Phe Asp Gly Tyr Leu Thr Lys Leu Leu Leu Thr
            20                  25                  30

Gly Lys Cys Val Cys Ala Gly Phe Leu Asn Ile Asp Cys Gly Leu Thr
        35                  40                  45

Asn Arg Ser Thr Tyr Asn Asp Thr Asp Thr Thr Leu Thr Tyr Val Ser
    50                  55                  60

Asp Arg Glu Phe Val Glu Gly Gly Asn Gly Lys Ser Tyr Asp Ile Met
65                  70                  75                  80

Ala Gln Tyr Ile Ala Asp Ala Thr Asn Glu Gln Glu Lys Thr Leu Arg
                85                  90                  95

Ser Phe Pro Asp Gly Gln Arg Asn Cys Tyr Thr Leu Pro Thr Asn Ser
            100                 105                 110

Ser Lys Lys Tyr Leu Ile Arg Ala Thr Phe Thr Tyr Gly Asn Tyr Asp
        115                 120                 125

Gly Leu Asn Ser Ser Glu Lys Gly Ser Leu Phe Leu Phe Gly Leu His
    130                 135                 140

Ile Gly Val Asn Phe Trp Ala Thr Val Asn Leu Thr Asn Trp Gly Ser
145                 150                 155                 160

Ser Asp Thr Met Tyr Lys Glu Val Ile Thr Val Ala Pro Asp Lys Phe
                165                 170                 175

Ile Ser Val Cys Leu Ile Asn Leu Gly Ser Gly Thr Pro Phe Val Ser
            180                 185                 190

Thr Leu Asp Leu Arg Glu Leu Asp Gly Ala Met Phe Pro Phe Leu Asn
        195                 200                 205

Leu Ser Val Ser Ile Ser His Leu Ala Arg Gln Arg Tyr Gly Ser Val
    210                 215                 220
```

```
Asp Asp Tyr Ile Thr Arg Tyr Pro Thr Asp Pro Phe Asp Arg Phe Trp
225                 230                 235                 240

Glu Ala Ala Leu Arg Tyr Lys Phe Pro Phe Leu Asn Met Thr Thr Asn
                245                 250                 255

Gln Asp Val Thr Lys Leu Pro Gly Asn Asp Asp Phe Gln Val Pro Met
            260                 265                 270

Pro Ile Leu Gln Lys Ala Ser Thr Ile Ser Ser Asn Phe Ser Glu Phe
        275                 280                 285

Asn Val Ser Val Ile Phe Pro Asp Asn Met Lys Asn Ile Asp Asn Ile
    290                 295                 300

Asn Asn Ile Asp Tyr Arg Ser Leu Glu Leu Leu Pro Ile Phe His Phe
305                 310                 315                 320

Ala Asp Ile Gly Gly Asn Asn Gln Asn Arg Thr Phe Asp Ile Tyr Asn
                325                 330                 335

Asp Gly Asn Leu Met Phe Pro Asn Tyr Ile Pro Pro Leu Phe Arg Ala
            340                 345                 350

Glu Ser Thr Tyr Gln Ser Gly Lys Phe Leu Arg Lys Arg Gly Leu Asn
        355                 360                 365

Phe Thr Leu Arg Lys Thr Pro Ser Ser Glu Leu Gln Pro Leu Ile Asn
    370                 375                 380

Ala Phe Glu Val Tyr Ser Leu Val His Thr Asp Asn Leu Thr Thr Ser
385                 390                 395                 400

Pro Asp Asp Val Asp Tyr Met Lys Glu Val Lys Lys Tyr Tyr Ser Tyr
                405                 410                 415

Thr Arg Asn Trp Asn Gly Asp Pro Cys Ser Pro Arg Glu Tyr Ser Trp
            420                 425                 430

Gln Gly Leu Ala Cys Asp Tyr Ala Asn Gly Asn Lys Asn Pro Arg Ile
        435                 440                 445

Thr Arg Met Asp Leu Ser His Asn Asn Leu Thr Gly Ala Ile Pro Asp
    450                 455                 460

Tyr Gln Leu Asn Ser Leu Arg Val Leu Asp Ser Ser Cys Gly Ile Pro
465                 470                 475                 480

Pro Thr Pro Cys Thr Gly Leu Tyr Pro Leu Glu Ala Val Leu Glu Arg
                485                 490                 495

Leu Glu Phe Ala Gly Lys Ser Ala Glu Gln Glu Asp Tyr Ser Ile Tyr
            500                 505                 510

Glu Glu Glu Ala Pro Leu His Ile Asp Ile Lys Arg Phe Thr Tyr Ala
        515                 520                 525

Glu Leu Lys Leu Ile Thr Asn Asn Phe Gln Ser Ile Ile Gly Lys Gly
    530                 535                 540

Gly Phe Gly Thr Val Tyr His Gly Ile Leu Glu Asn Asn Asp Glu Val
545                 550                 555                 560

Ala Val Lys Val Leu Val Glu Thr Ser Ile Ala Glu Ser Lys Asp Phe
                565                 570                 575

Leu Pro Glu Arg Lys Ser Ser Ala Val Met Val Gly Ile Thr Tyr Gln
            580                 585                 590

Arg Arg Ser Arg Thr Gly Leu Gln Asp Thr Ala Ser Gly Asp Ala Ala
        595                 600                 605

Gln Arg Thr Thr Asn Phe Ala His Phe Asp Ala Gly Tyr Asp Ser Ser
    610                 615                 620

Leu Asn Trp Glu Glu Arg Leu His Ile Ala Leu Asp Ala Ala Gln Gly
625                 630                 635                 640

Leu Glu Tyr Leu His Glu Ser Cys Ser Pro Ser Ile Val His Arg Asp
                645                 650                 655
```

```
Val Lys Thr Pro Asn Ile Leu Leu Asp Lys Asn Leu Val Ala Lys Ile
            660                 665                 670

Ser Asp Phe Gly Leu Ser Arg Ala Phe Asn Ala Ala His Thr His Ile
        675                 680                 685

Ser Thr Val Val Ala Gly Thr Leu Gly Tyr Leu Asp Pro Glu Tyr His
    690                 695                 700

Ala Thr Phe Gln Leu Thr Val Lys Thr Asp Val Tyr Ser Phe Gly Ile
705                 710                 715                 720

Val Leu Leu Glu Ile Val Thr Gly Gln Pro Pro Val Phe Met Asp Pro
                725                 730                 735

Gln Thr Val His Leu Pro Asn Trp Val Arg Gln Lys Ile Asp Lys Gly
            740                 745                 750

Ser Ile His Asp Val Val Asp Lys Lys Leu Leu Asp Gln Tyr Asp Ala
        755                 760                 765

Thr His Leu Gln Thr Val Ile Asp Leu Ala Met Asn Cys Leu Glu Asn
    770                 775                 780

Thr Ser Ile Asp Arg Pro Ser Met Thr Glu Val Val Ser Val Leu Lys
785                 790                 795                 800

Val Leu Phe Thr Val Ala Ile Ser Ser Glu Lys Arg Ser Val Thr Ser
                805                 810                 815

Thr Pro Gln Glu Lys Asn Val Met Asp Ala Asp Ile Pro Arg Gln Phe
            820                 825                 830

His Leu Met Ile Ser Gly Ala Thr Thr Thr Ser Tyr Asp Asn Glu Gly
        835                 840                 845

Ser Ser Ser Gln Ser Gly Pro Thr Gly Gly Met Ser Glu Ile Ser Tyr
    850                 855                 860

Ile Ser Gly Arg
865


<210> SEQ ID NO 33
<211> LENGTH: 12
<212> TYPE: PRT
<213> ORGANISM: Artificial sequence
<220> FEATURE:
<223> OTHER INFORMATION: consensus sequence
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be Asp or Glu
<220> FEATURE:
<221> NAME/KEY: MISC_FEATURE
<222> LOCATION: (8)..(8)
<223> OTHER INFORMATION: Xaa can be any amino acid
<220> FEATURE:
<221> NAME/KEY: MISC_FEATURE
<222> LOCATION: (12)..(12)
<223> OTHER INFORMATION: Xaa can be Tyr or Phe

<400> SEQUENCE: 33

Leu Arg Xaa Phe Pro Xaa Gly Xaa Arg Asn Cys Xaa
1               5                   10
```